(12) United States Patent
Benoit et al.

(10) Patent No.: US 10,195,284 B2
(45) Date of Patent: Feb. 5, 2019

(54) COMPOSITIONS AND METHODS FOR CONTROLLED LOCALIZED DELIVERY OF BONE FORMING THERAPEUTIC AGENTS

(71) Applicant: University of Rochester, Rochester, NY (US)

(72) Inventors: Danielle Benoit, Rochester, NY (US); J. Edward Puzas, Pittsford, NY (US); Maureen Newman, Rochester, NY (US); Tzong-Jen Sheu, Rochester, NY (US); Benjamin Frisch, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 15/276,382

(22) Filed: Sep. 26, 2016

(65) Prior Publication Data
US 2017/0072062 A1    Mar. 16, 2017

Related U.S. Application Data

(63) Continuation-in-part of application No. 14/853,772, filed on Sep. 14, 2015, which is a continuation-in-part of application No. PCT/US2014/027354, filed on Mar. 14, 2014.

(60) Provisional application No. 61/783,542, filed on Mar. 14, 2013.

(51) Int. Cl.
| | |
|---|---|
| *A61K 47/58* | (2017.01) |
| *A61K 31/497* | (2006.01) |
| *A61K 47/48* | (2006.01) |
| *A61K 31/404* | (2006.01) |
| *A61K 47/69* | (2017.01) |

(52) U.S. Cl.
CPC ...... *A61K 47/48176* (2013.01); *A61K 31/404* (2013.01); *A61K 31/497* (2013.01); *A61K 47/58* (2017.08); *A61K 47/6933* (2017.08)

(58) Field of Classification Search
CPC .............................. A61K 47/58; A61K 31/497
See application file for complete search history.

(56) References Cited

U.S. PATENT DOCUMENTS

| | | | |
|---|---|---|---|
| 7,241,732 B2 * | 7/2007 | Puzas .................... | A61L 27/227 514/15.4 |
| 2004/0254261 A1 | 12/2004 | Kojima et al. | |
| 2005/0112168 A1 | 5/2005 | Puzas | |
| 2005/0165136 A1 | 7/2005 | Mays et al. | |
| 2007/0087031 A1 | 4/2007 | Ashman et al. | |
| 2008/0292714 A1 | 11/2008 | Garlich et al. | |
| 2011/0142764 A1 * | 6/2011 | Satchi-Fainaro ..... | C07F 9/3873 424/9.1 |
| 2011/0171144 A1 * | 7/2011 | Wang ..................... | A61K 9/107 424/52 |
| 2011/0294998 A1 | 12/2011 | Davis et al. | |
| 2012/0009674 A1 * | 1/2012 | Mays .................... | C12N 5/0607 435/366 |
| 2012/0157539 A1 * | 6/2012 | Dalton ................. | A61K 31/138 514/619 |

OTHER PUBLICATIONS

Sisask et al., 2013, Rats treated with AZD2858, a GSK3 inhibitor, heal fractures rapidly without endochondral bone formation, Bone, 54: 126-132.*
Gilmour et al., 2013, Human stem cell osteoblastogenesis mediated by novel glycogen synthase kinase 3 inhibitors induces bone formation and a unique bone turnover biomarker profile in rats, Toxicology and Applied Pharmacology, 272: 399-407.*
Marsell et al., 2012, GSK-3 inhibition by an orally active small molecule increases bone mass in rats, Bone, 50: 619-627.*
Baranello et al., 2014, Poly(styrene-alt-maleic anhydride)-Based Diblock Copolymer Micelles Exhibit Versatile Hydrophobic Drug Loading, Drug-Dependent Release, and Internalization by Multidrug Resistant Ovarian Cancer Cells, Biomacromolecules, 15: 2629-2641.*
Baranello et al., 2015, Micelle Delivery of Parthenolide to Acute Myeloid Leukemia Cells, Cell Mol Bloeng, 8(3): 455-470.*
Oba et al., 2005, MIP-1a utilizes both CCR1 and CCR5 to induce osteoclast formation and increase adhesion of myeloma cells to marrow stromal cells, Experimental Hematology, 33: 272-278.*
Menu et al., 2006, Role of CCR1 and CCR5 in homing and growth of multiple myeloma and in the development of osteolytic lesions : a study in the 5TMM model, Clin Exp Metastasis, 23: 291-300.*
Sheu et al., 2002, "Use of a phage display technique to identify potential osteoblast binding sites within osteoclast lacunae", Journal of Bone and Mineral Research, 17(5): 915-922.
Garrett et al., 2002, "The role of statins as potential targets for bone formation", Arthritis Res. 4(4):237-240.
Vougogiannopoulou et al., 2008, "Soluble 3',6-Substituted Indirubins with Enhanced Selectivity toward Glycogen Synthase Kinase-3 Alter Circadian Period", Journal of Medicinal Chemistry, 51(20): 6421-6431.
Mundy, 2001, "Statins and their potential for osteoporosis", Bone 29(6):495-497.
Clevers, 2006, "Wnt/β-catenin signaling in development and disease", Cell 127(3):469-480.

(Continued)

*Primary Examiner* — Amber D Steele
(74) *Attorney, Agent, or Firm* — Riverside Law LLP

(57) ABSTRACT

The present invention provides compositions and methods for providing controllable local delivery of a therapeutic agent to promote bone formation. In certain embodiments, the invention is used as a treatment for a subject with osteoporosis, bone cancer or bone fracture. The invention provides a therapeutic agent that is tethered to a polymer to form a therapeutic-tethered macromer, where the therapeutic agent is controllably released from the conjugate by degradation of the tether. In certain embodiments, the therapeutic agent is an inhibitor of GSK3β. In certain embodiments, the composition of the invention is specifically targeted to a site in need of bone formation or treatment.

38 Claims, 60 Drawing Sheets
Specification includes a Sequence Listing.

(56) References Cited

OTHER PUBLICATIONS

Kansara et al., 2009, "Wnt inhibitory factor 1 is epigenetically silenced in human osteosarcoma, and targeted disruption accelerates osteosarcomagenesis in mice", J. Clin. Invest. 119(4):837-851.
Gong et al., 2001, "LDL receptor-related protein 5 (LRP5) affects bone accrual and eye development", Cell 107(4):513-523.
Little et al., 2002, "A mutation in the LDL receptor-related protein 5 gene results in the autosomal dominant high-bone-mass trait", Am. J. Hum. Genet. 70(1):11-19.
Loots et al., 2005, "Genomic deletion of a long-range bone enhancer misregulates sclerostin in Van Buchem disease", Genome Res. 15(7):928-935.
Zalipsky, 1995, "Chemistry of polyethylene glycol conjugates with biologically active molecules", Advanced Drug Delivery Reviews, 16(2-3):157-182.
Benoit et al., 2006, "Synthesis and characterization of a fluvastatin-releasing hydrogel delivery system to modulate hMSC differentiation and function for bone regeneration", Biomaterials, 27(36): 6102-6110.
Matsuo et al., 2008, "Osteoclast—osteoblast communication", Archives of Biochemistry and Biophysics, 473(2): 201-209.
Duncan et al., 2006, "Polymer therapeutics—polymers as drugs, drug and protein conjugates and gene delivery systems: Past, present and future opportunities", Journal of Drug Targeting, 14(6):337-341.
Vicent et al., 2008, "Polymer conjugates as therapeutics: future trends, challenges and opportunities", Expert Opinion Drug Delivery, 5(5):593-614.
Duncan, 2003, "The dawning era of polymer therapeutics", Nature Reviews/Drug Discovery 2(5):347-360.
Kiick, 2007, "Materials Science. Polymer therapeutics", Science 317(5842):(1182-1183), pp. 1-5.
Setton, 2008, "Peptide-functionalized polymer nanoparticles target and bind to articular cartilage tissue, making them promising drug-delivery vehicles", Nature Materials, 7(3):172-174.
Wang et al., 2006, "Pharmacokinetic and Biodistribution Studies of a Bone-Targeting Drug Delivery System Based on N-(2-Hydroxypropyl)methacrylamide Copolymers", Molecular Pharmaceuticals, 3(6):717-725.
Moad et al., 2005, "Advances in RAFT polymerization: the synthesis of polymers with defined end-groups", Polymer, 46(19): 8458-8468.
Convertine et al., 2009, Development of a novel endosomolytic diblock copolymer for siRNA delivery, Journal of Controlled Release, 133(3):(221-229), pp. 1-22.
Duvall et al., 2010, "Intracellular Delivery of a Proapoptotic Peptide via Conjugation to a RAFT Synthesized Endosomolytic Polymer", Molecular Pharmaceuticals, 7(2):(468-476), pp. 1-20.
Henry et al., 2009, "End-Functionalized Polymers and Junction-Functionalized Diblock Copolymers Via RAFT Chain Extension with Maleimido Monomers" Bioconjugate Chem 20(6):(1122-1128), pp. 1-18.
Nuttelman et al., 2006, "The effect of ethylene glycol methacrylate phosphate in PEG hydrogels on mineralization and viability of encapsulated hMSCs", Biomaterials 27(8):1377-1386.
Nuttelman et al., 2006, "Dexamethasone-functionalized gels induce osteogenic differentiation of encapsulated hMSCs", Journal of Biomedical Materials Research Part A, 76A(1):183-195.
Lipton et al., 2007, "Phase II, randomized, multicenter, comparative study of peginterferon-α-2a (40 kD) (Pegasys®) versus interferon α-2a (Roferon®-A) in patients with treatment-naïve, chronic-phase chronic myelogenous leukemia", Leukemia Lymphoma, 48(3):497-505.
Reddy et al., 2009, "Peginterferon alfa-2a (40kDa) and ribavirin: comparable rates of sustained virological response in sub-sets of older and younger HCV genotype 1 patients", Journal of Viral Hepatitis, 16(10):724-731.
Talpaz et al., 2005, "Phase I Evaluation of a 40-kDa Branched-Chain Long-Acting Pegylated IFN-A-2aWith andWithout Cytarabine in Patientswith ChronicMyelogenous Leukemia", Clinical Cancer Research, 11(17):6247-6255.
Zeuzem et al., 2008, "Telaprevir, peginterferon alfa-2a, and ribavirin for 28 days in chronic hepatitis C patients", Journal of Hepatology, 49(2):157-159.
Zeuzem et al., 2004, "Peginterferon Alfa-2a (40 Kilodaltons) and Ribavirin in Patients With Chronic Hepatitis C and Normal Aminotransferase Levels", Gastroenterology 127(6):1724-1732.
Johnson et al., 2010, "Synthesis of Statistical Copolymers Containing Multiple Functional Peptides for Nucleic Acid Delivery", Biomacromolecules, 11(11): (3007-3013), pp. 1-20.
ten Cate et al., 2007, "Synthesis of ABC-Triblock Peptide-Polymer Conjugates for the Positioning of Peptide Segments within Block Copolymer Aggregates", Macromol Chem Physic, 208(13): 1437-1446.
Segvich et al., 2009, "The adsorption of preferential binding peptides to apatite-based Materials", Biomaterials 30(7): (1287-1298), pp. 1-25.
Weiger et al., 2010, "Quantification of the binding affinity of a specific hydroxyapatite binding peptide", Biomaterials 31(11):2955-2963.
Benoit et al., 2011, "Synthesis of folate-functionalized RAFT polymers for targeted siRNA delivery", Biomacromolecules 12(7):(2708-2714), pp. 1-17.
Benoit et al., 2007, "Multifunctional hydrogels that promote osteogenic Hmsc differentiation through stimulation and sequestering of BMP2", Adv Funct Mater 17(13):(2085-2093), pp. 1-19.
Curry, 2004, "Phase I dose escalation trial of feverfew with standardized doses of parthenolide in patients with cancer", Investigational New Drugs 22(3):299-305.
Franc et al., 2009, "gem-Bisphosphonate-Ended Group Dendrimers: Design and Gadolinium Complexing Properties", Eur J Org Chem, 2009(25): 4290-4299.
Ross et al., 2011, "Binding affinity of surface functionalized gold nanoparticles to hydroxyapatite", Journal of Biomedical Materials Research Part A, 99A(1): 58-66.
Doschak et al., 2009, "Improved Bone Delivery of Osteoprotegerin by Bisphosphonate Conjugation in a Rat Model of Osteoarthritis", Molecular Pharmaceutics, 6(2):637-640.
Gittens et al., 2005, "Imparting Mineral Affinity to Fetuin by Bisphosphonate Conjugation: A Comparison of Three Bisphosphonate Conjugation Schemes", Molecular Pharmaceutics, 2(5):392-406.
Low et al., 2012, "Targeting Polymer Therapeutics to Bone", Advance Drug Delivery Reviews, 64(12):(1189-1204), pp. 1-38.
Ayres et al., 2005, "β-Sheet Side Chain Polymers Synthesized by Atom-Transfer Radical Polymerization", Biomacromolecules, 6(2): 825-831.
Maynard et al., 2001, "Inhibition of Cell Adhesion to Fibronectin by Oligopeptide-Substituted Polynorbornenes", J Am Chem Soc, 123(7): 1275-1279.
Marozas et al., "Development of a Novel Targeted Drug Delivery System for the Treatment of Osteoporosis", Univ. of Rochester Center for Musculoskeletal Research, Jul. 2012, pp. 6-14.
Wang et al. 2009, "Inhibition of glycogen synthase kinase-3β attenuates glucocorticoid-induced bone loss", Life Sciences, 85(19-20):685-692.
Grey, 2007, "Emerging pharmacologic therapies for osteoporosis", Expert Opinion on Emerging Drugs, 12(3):493-508.
Sekido et al., 2001, "Novel Drug Delivery System to Bone Using Acidic Oligopeptide: Pharmacokinetic Characteristics and Pharmacological Potential", Journal of Drug Targning, vol. 9(2): 111-121.
Ouyang et al., 2009, "Bone Targeting Prodrugs Based on Peptide Dendrimers, Synthesis and Hydroxyapatite Binding In Vitro", Letters in Organic Chemistry, 6(4): 272-277.
Ayres et al., 2003, "Elastin-Based Side-Chain Polymers Synthesized by ATRP", Macromolecules, 36(16): 5967-5973.
Fernandez-Trillo et al., 2007, "Elastin-Based Side-Chain Polymers: Improved Synthesis via RAFT and Stimulus Responsive Behavior", Macromolecules, 40(17): 6094-6099.

\* cited by examiner

R-group

Z-group

Peptide-

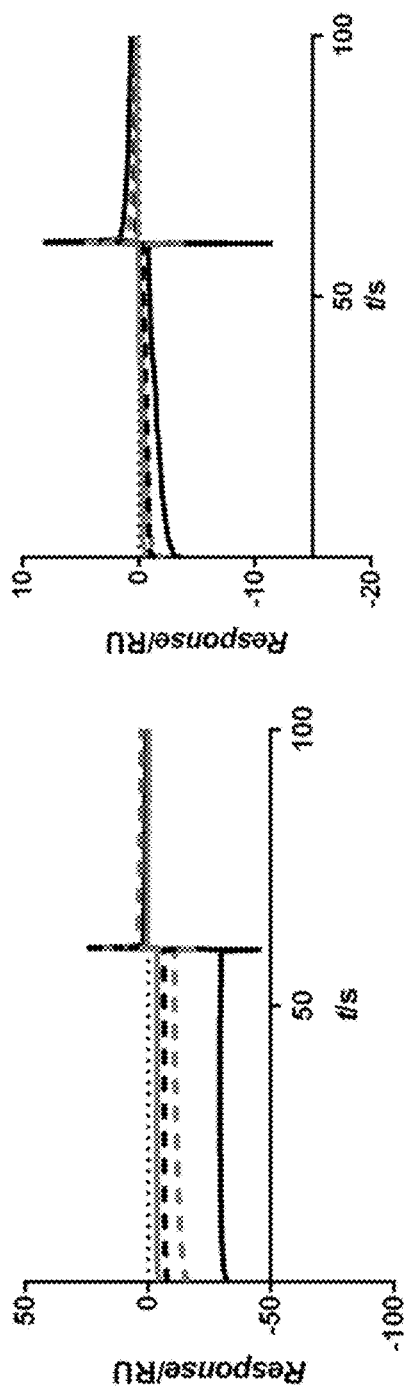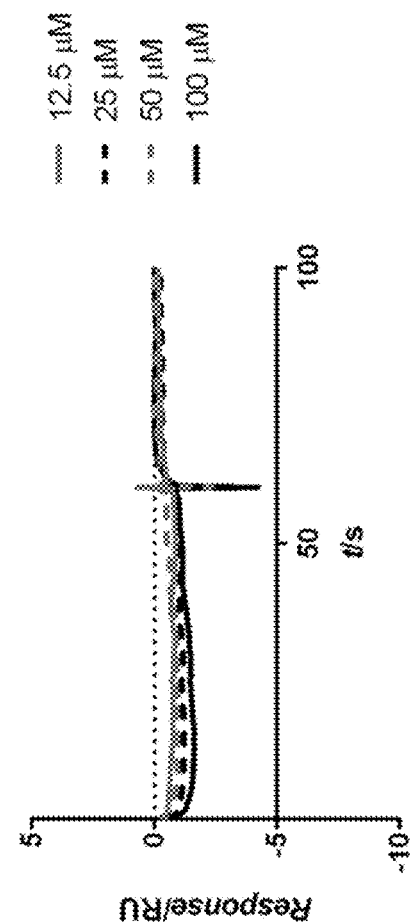
Figure 23A
Figure 23B
Figure 23C

| OCs | Dose | | | | | |
|---|---|---|---|---|---|---|
| Treatment | | 0.1 μM | 0.5 μM | 1.0 μM | 5.0 μM | 10.0 μM |
| | TBP | ns | ns | ns | ns | ns |
| | SCP | ns | ns | ns | ns | ns |
| | PEG | ns | ns | ns | ns | ns |
| | pTBP | ns | ns | ns | ns | ns |
| | pSCP | ns | ns | ns | ns | ns |

(Via TRAP-positive cell counts)

| MSCs | Dose | | | | | |
|---|---|---|---|---|---|---|
| Treatment | | 0.1 μM | 0.5 μM | 1.0 μM | 5.0 μM | 10.0 μM |
| | TBP | **** | **** | ns | *** | * |
| | SCP | **** | **** | **** | * | ns |
| | PEG | **** | * | ns | **** | ns |
| | pTBP | ns | ** | ** | *** | ns |
| | pSCP | **** | *** | ** | *** | ** |

(Via Alamar Blue assay)

Figure 25

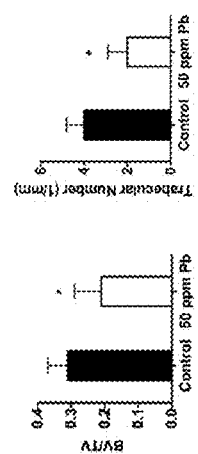
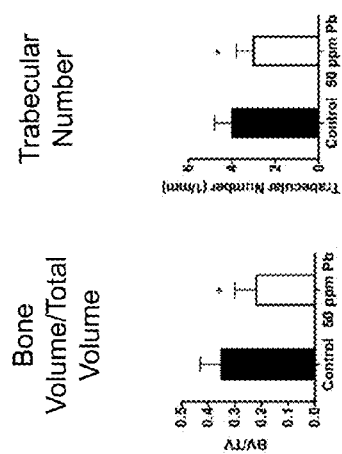
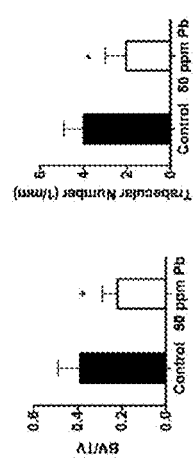
Figure 36A
Figure 36B
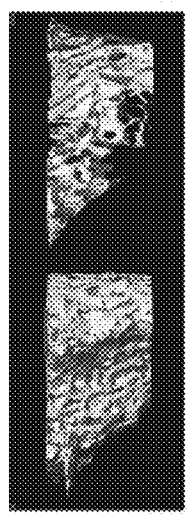
Figure 36C

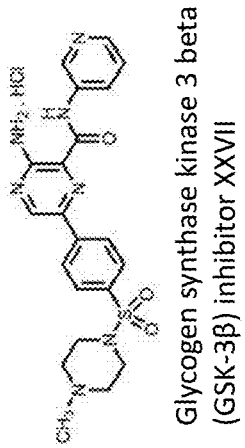
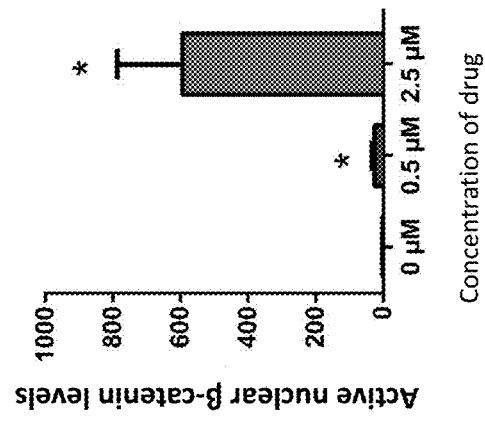
Figure 43B
Figure 43A

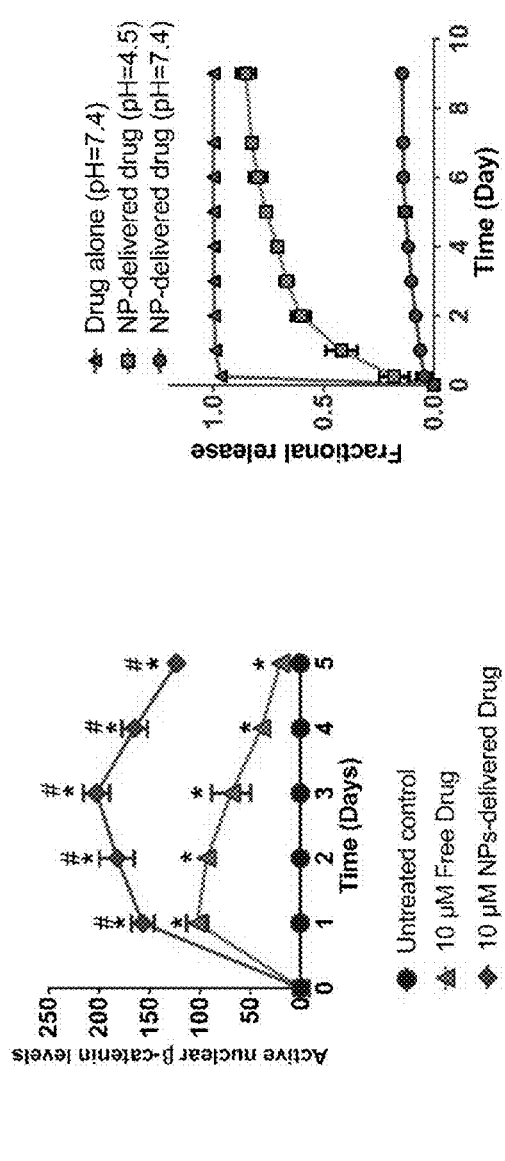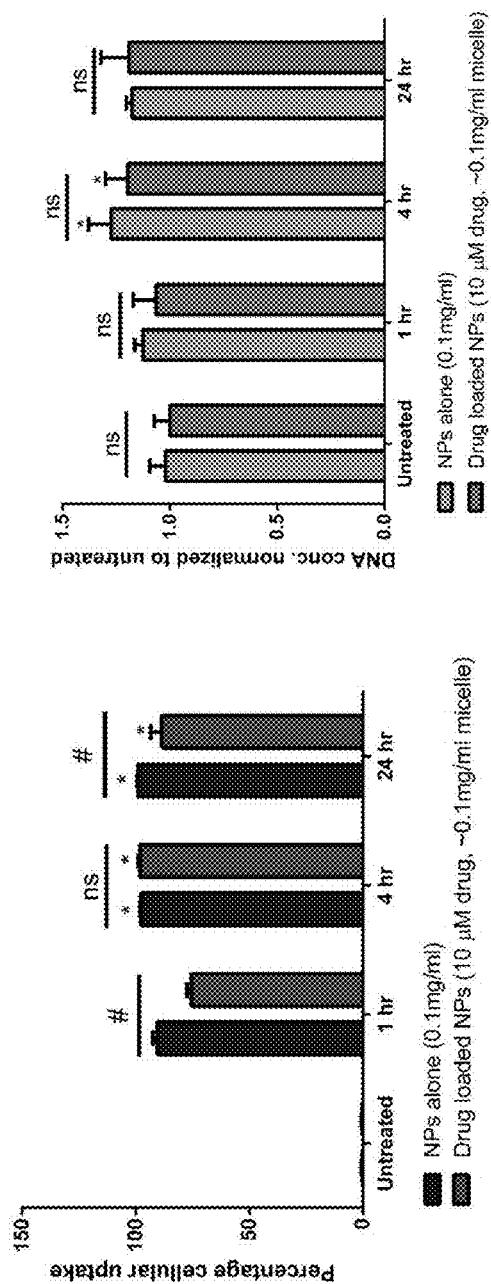
Figure 45

| NP characterization | TBP-NP | NP |
|---|---|---|
| Size (nm) | 30 ± 2 | 25 ± 3 |
| Zeta potential (mV) | -50 ± 1 | -49 ± 3 |
| Loading effiency ($mass_{loaded}/mass_{original}$) | 78% | 65% |
| Loading capacity ($mass_{drug}/mass_{NP}$) | 8.3% | 6.2% |

Figure 47

SEQUENCE LISTING

```
<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 1

Thr Pro Leu Ser Tyr Leu Lys Gly Leu Val Thr Val Gly
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 2

Val Pro Val Gly Thr Leu Ser Tyr Leu Lys Leu Thr Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Chemically Synthesized
```

```
<400> SEQUENCE: 3

Thr Pro Leu Ser Tyr Leu Lys Gly Leu Val Thr Val
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 4

Val Pro Val Gly Thr Leu Ser Tyr Leu Lys Leu Thr
1               5                   10
```

COMPOSITIONS AND METHODS FOR CONTROLLED LOCALIZED DELIVERY OF BONE FORMING THERAPEUTIC AGENTS

CROSS-REFERENCE TO RELATED APPLICATIONS

This application is a continuation-in-part application of U.S. patent application Ser. No. 14/853,772, filed on Sep. 14, 2015, which is in turn entitled to priority to International Patent Application No. PCT/US2014/027354, filed on Mar. 14, 2014, and to U.S. Provisional Patent Application No. 61/783,542, filed Mar. 14, 2013, each of which application is hereby incorporated herein by reference in its entirety.

STATEMENT REGARDING FEDERALLY SPONSORED RESEARCH OR DEVELOPMENT

This invention was made with government support under grant numbers P30 ES001247 and K12 ES019852, awarded by the National Institutes of Health (NIH), and CBET 1450987, awarded by the National Science Foundation (NSF). The government has certain rights in the invention.

BACKGROUND OF THE INVENTION

Bone disorders, including those associated with primary or secondary bone cancer, traumatic injury to bone (e.g., fracture), aberrant osteolytic activity (e.g., bone metastases and wear-induced osteolysis), and osteoporosis, are a major health threat. Bones are constantly being remodeled through osteoclast and osteoblast activity. When there is an uncoupling between the cells, an imbalance between resorption and formation, or a traumatic event, bone quality and strength suffers.

Specifically, osteoporosis affects 44 million Americans, costing an estimated $19 billion in health expenditures in 2005. Osteoporosis is the result of elevated osteoclast activity and/or decreased osteoblast activity, which causes more bone to be resorbed than rebuilt. Bones become weaker and are more prone to fractures which can be fatal in older patients (National Osteoporosis Foundation). Orthoporotic fractures are common, with the incidence increasing with age, and are associated with considerable morbidity, mortality, and deterioration of the quality of life.

The underlying cause of osteoporosis is an imbalance in the rate of bone formation and resorption during skeletal remodeling due to the inability of osteoblasts to match the activity of osteoclasts. Most current osteoporosis therapies target osteoclasts and not osteoblasts. Thus, although these therapies slow bone resorption, they do not target bone anabolism, which represents a critical means to regenerate lost bone density. While there are interventions that reduce the risk of orthoporotic fractures, there is a lack of therapies that restore osteoblast function and initiate the replacement of already lost bone to restore bone health.

The ability to modulate bone formation and resorption is dependent on providing sustained and local delivery of existing or potential therapeutic agents. However, effective delivery of small molecules locally and sustainably to bone remains a significant challenge. For example, bolus delivery results in rapid loss of drug, resulting in little or no therapeutic efficacy. Further, local delivery of small molecules has not been successfully demonstrated in bone. Therefore, there is a need in the art for compositions and methods to provide local sustained delivery of therapeutic agents to promote bone formation. The present invention satisfies this unmet need.

SUMMARY OF THE INVENTION

The present invention provides a composition for controlled local delivery of a therapeutic agent to bone, the composition comprising a therapeutic-tethered macromer comprising a targeting ligand and a therapeutic agent tethered to a polymer, wherein the therapeutic agent is 3-amino-6-{4-[(4-methyl-1-piperazinyl)sulfonyl]phenyl}-N-(3-pyridinyl)-2-pyrazinecarboxamide.

In one embodiment, the composition further comprises a C-C motif ligand 3 (CCL3) pathway inhibitor. In one embodiment, the CCL3 pathway inhibitor is selected from the group consisting of BX471 and Maraviroc. In one embodiment, the targeting ligand is tethered to polymer micelles encapsulating the therapeutic agent. In one embodiment, the therapeutic agent is tethered to the polymer via at least one degradable tether. In one embodiment, the polymer is selected from the group consisting of poly(ethylene glycol) (PEG) methacrylate and poly(styrene-alt-maleic anhydride)-b-poly(styrene) (PSMA-b-PS). In one embodiment, the therapeutic-tethered macromer is contained within a hydrogel.

In one embodiment, the composition comprises a bone-homed particle comprising the therapeutic-tethered macromer. In one embodiment, the bone-homed particle comprises at least one targeting domain that specifically binds to a target associated with a site in need of bone formation. In one embodiment, the at least one targeting domain comprises a targeting peptide that specifically binds to tartrate-resistant acid phosphatase (TRAP).

In one embodiment, the bone-homed particle comprises at least one monomer that targets the particle to bone, to a resorptive pit, to a bone fracture, to bone marrow, or any combination thereof. In one embodiment, the monomer is a phosphate-containing monomer. In one embodiment, the monomer is selected from the group consisting of 6-methacryloyloxyhexyl dihydrogen phosphate, methacrylated glutamic acid, and methacrylated aspartic acid.

In one embodiment, the particle comprises multivalent targeting. In one embodiment, the targeting peptide comprises the amino acid sequence of SEQ ID NO: 1. In one embodiment, the bone-homed particle is a micelle, a nanoparticle, or a polymer. In one embodiment, the polymer comprises one or more monomers that target the polymer to bone, to a resorptive pit, to a bone fracture, to bone marrow, or any combination thereof.

In another aspect, the present invention provides a composition for controlled local delivery of a therapeutic agent to bone, the composition comprising a therapeutic-tethered macromer comprising a targeting ligand and a therapeutic agent tethered to poly(styrene-alt-maleic anhydride)-b-poly(styrene) (PSMA-b-PS).

In one embodiment, the therapeutic agent is a C-C motif ligand 3 (CCL3) pathway inhibitor. In one embodiment, the CCL3 pathway inhibitor is BX471, Maraviroc, or both. In one embodiment, the targeting ligand is tethered to polymer micelles encapsulating the therapeutic agent. In one embodiment, the therapeutic agent is an inhibitor of GSK3β. In one embodiment, the therapeutic agent is selected from the group consisting of 6-bromoindirubin-3'-oxime (BIO) and 3-amino-6-{4-[(4-methyl-1-piperazinyl)sulfonyl]phenyl}-

N-(3-pyridinyl)-2-pyrazinecarboxamide. In one embodiment, the therapeutic agent is tethered to the polymer via at least one degradable tether.

In one embodiment, the composition comprises a bone-homed particle comprising the therapeutic-tethered macromer. In one embodiment, the bone-homed particle comprises at least one targeting domain that specifically binds to a target associated with a site in need of bone formation. In one embodiment, the at least one targeting domain is selected from the group consisting of a nucleic acid, peptide, antibody, antibody fragment, inorganic molecule, organic molecule, and combination thereof. In one embodiment, the at least one targeting domain comprises a targeting peptide that specifically binds to tartrate-resistant acid phosphatase (TRAP).

In one embodiment, the bone-homed particle comprises at least one monomer that targets the particle to bone. In one embodiment, the bone-homed particle comprises at least one monomer that targets the particle to a resorptive pit, a bone fracture, bone marrow, or any combination thereof. In one embodiment, the monomer is a phosphate-containing monomer. In one embodiment, the monomer is selected from the group consisting of 6-methacryloyloxyhexyl dihydrogen phosphate, methacrylated glutamic acid, and methacrylated aspartic acid. In one embodiment, the particle comprises multivalent targeting.

In one embodiment, the targeting peptide comprises the amino acid sequence of SEQ ID NO: 1. In one embodiment, the bone-homed particle is a micelle, a nanoparticle, or a polymer. In one embodiment, the polymer comprises one or more monomers that target the polymer to bone, to a resorptive pit, to a bone fracture, to bone marrow, or any combination thereof.

In another aspect, the present invention provides a method of promoting bone formation at a site in need of bone formation in a subject comprising administering to the subject the composition of claim 1, wherein the composition promotes bone formation.

In one embodiment, the subject has a disease or disorder selected from the group consisting of osteoporosis, osteonecrosis, osteomyelitis, osteoarthritis, Paget's disease, bone cancer, bone allograft rejection, bone autograft rejection, wear-debris induced osteolysis, and bone fracture.

In another aspect, the present invention provides a method of promoting bone formation at a site in need of bone formation in a subject comprising administering to the subject the composition of claim 18, wherein the composition promotes bone formation.

In one embodiment, the subject has a disease or disorder selected from the group consisting of osteoporosis, osteonecrosis, osteomyelitis, osteoarthritis, Paget's disease, bone cancer, bone allograft rejection, bone autograft rejection, wear-debris induced osteolysis, and bone fracture.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments that are presently preferred. It should be understood, however, that the invention is not limited to the precise arrangements and instrumentalities of the embodiments shown in the drawings.

FIG. 10A is the structure of the chain transfer agent (CTA) that is utilized to polymerize BIO-releasing polymers. FIG. 10B is the TRAP-targeting peptide-functionalized CTA. FIG. 10C is an exemplary therapeutic (BIO)-tethered macromere used to synthesize BIO-releasing polymers. BIO is attached to poly(ethylene glycol) methacrylate by hydrolytically degradable ester bonds residing within a lactide (lactic acid) tether. FIG. 10D is a design for brush architectures with releasable bone anabolic drug delivery capabilities. This particular design utilizes poly(ethylene glycol) monomethyl ether as the main component and poly(ethylene glycol) functionalized with degradable ester bonds tethering BIO for delivery.

Cumulative release (Mt/Moo) as a function of time and length of lactide tether from polymers (2 degradable bonds: triangles, 4 degradable bonds: squares, 6 degradable bonds: circles). *p<0.05 compared to all other tethers at the same time point, error bars are standard deviation (n=6).

Figure 12:
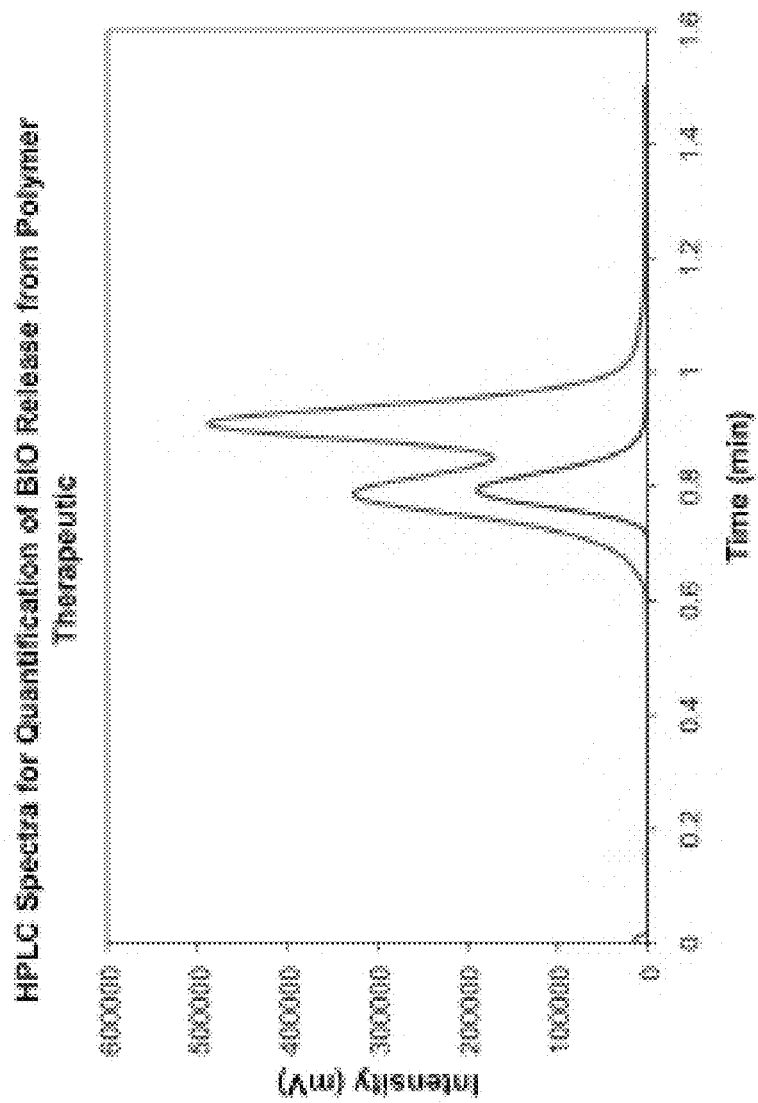

FIG. 12 is a graph depicting the HPLC UV-spectra of free BIO and BIO-functionalized RAFT polymers.

Figure 13:
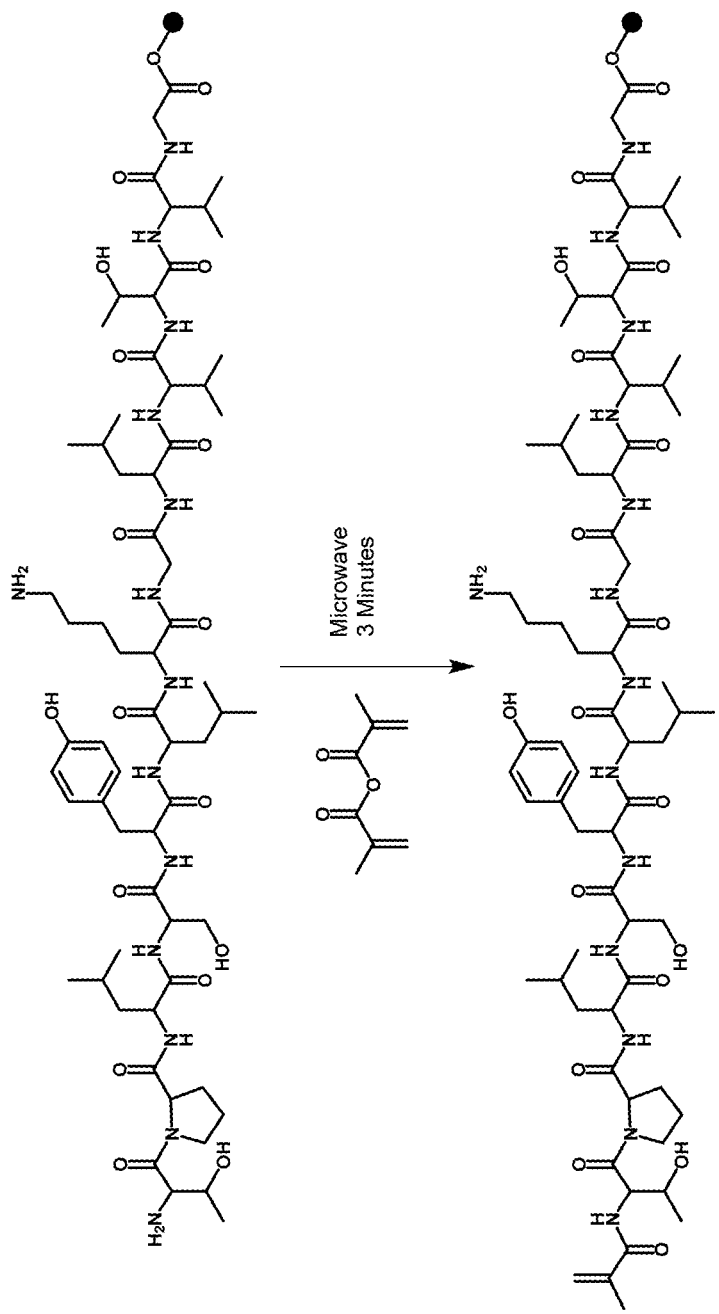

FIG. 13 depicts the microwave reaction for on-resin (black circles) functionalization of TBP (TPLSYLK-GLVTVG, SEQ ID NO: 1) with methacrylic anhydride. (VPVGTLSYLKLTG (SEQ ID NO: 2) was functionalized similarly)

Figure 14:
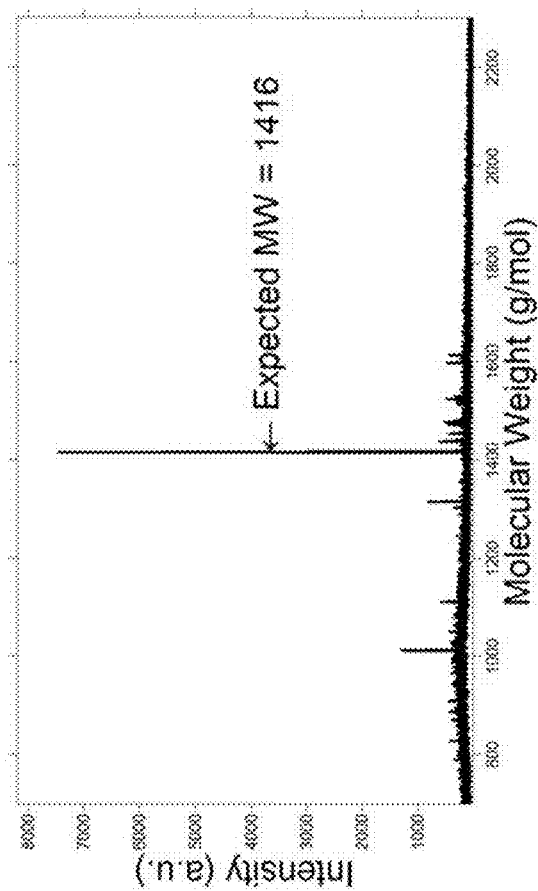

FIG. 14 depicts the MALDI-TOF spectra of complete modification of peptides with methacrylamide functionalities.

Figure 15:
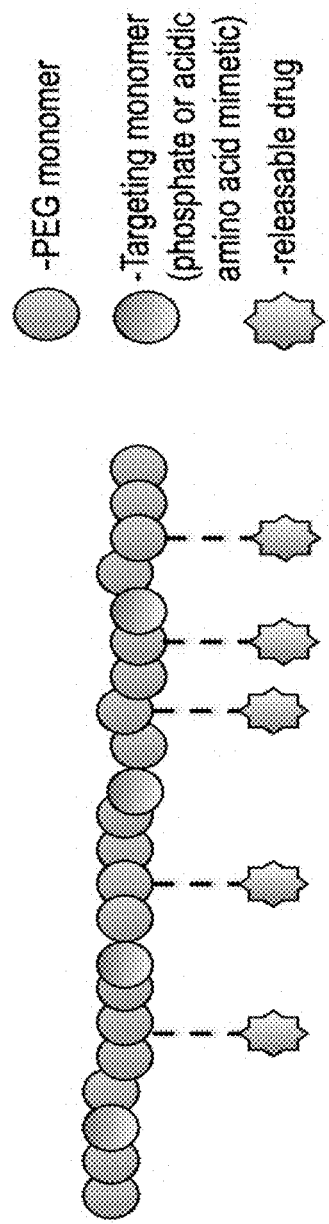

FIG. 15 is an illustration depicting a strategy to develop multivalent bone-targeted polymer therapeutics. Polymers are synthesized using RAFT polymerizations, a simple, reproducible, and scalable method to create highly controlled molecular weights and architectures. Targeting moieties separately presenting peptides will be incorporated for bone targeting in statistical copolymers with poly(ethylene glycol) (PEG) and drug (e.g., BIO)-releasing comonomers.

Figure 16:
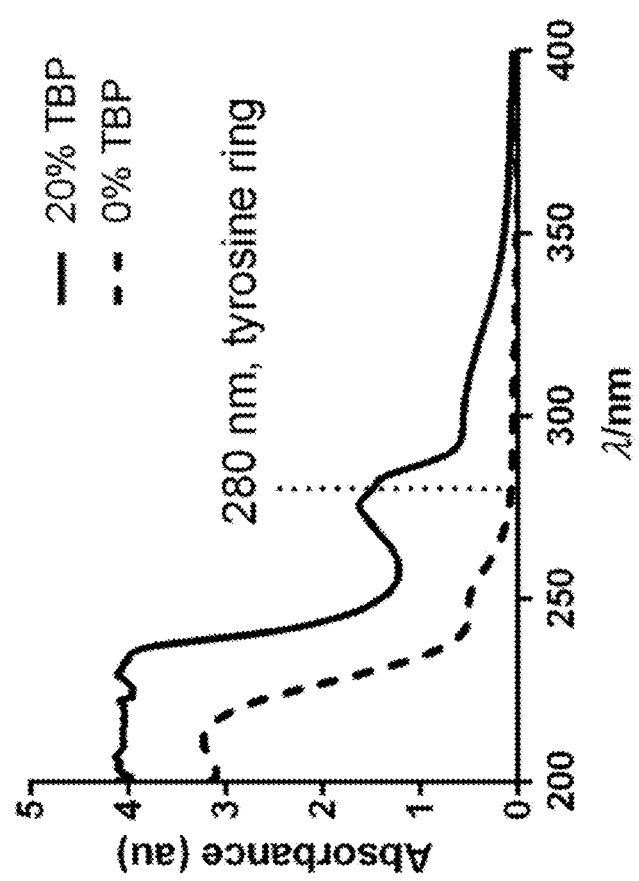

FIG. 16 depicts UV-vis spectrum of TBP-functionalized PEG polymers. The peak at 280 nm corresponds to the tyrosine ring in peptides.

Figure 17:
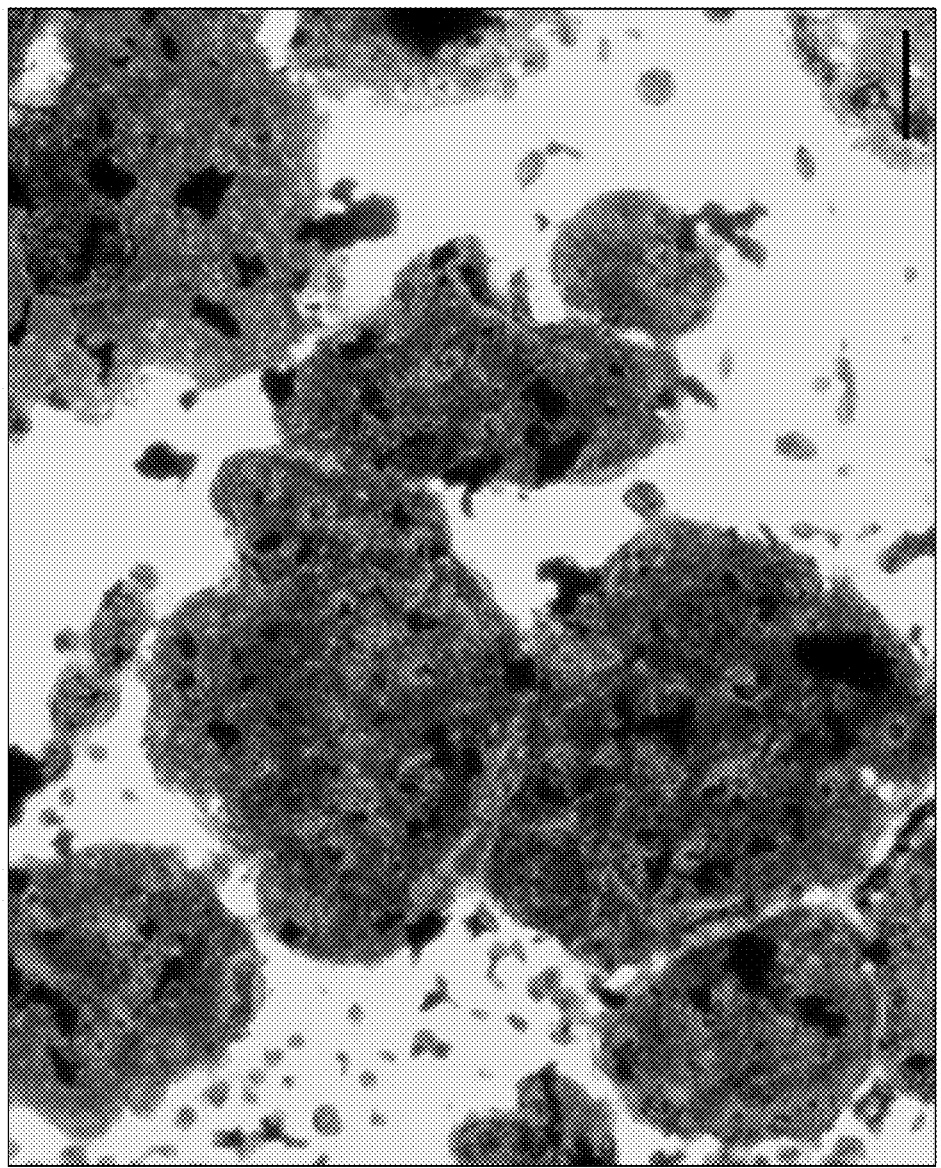

FIG. 17 is an image depicting spleen-derived monocytes grown on plastic stained positive for TRAP after 104 days of differentiation under the influence of M-CSF and RANKL. Magnification is 4×; scale bar is 100 μm. Image was acquired using an inverted Olympus CK40 microscope.

Figures 18A, 18B, 18C, 18D:
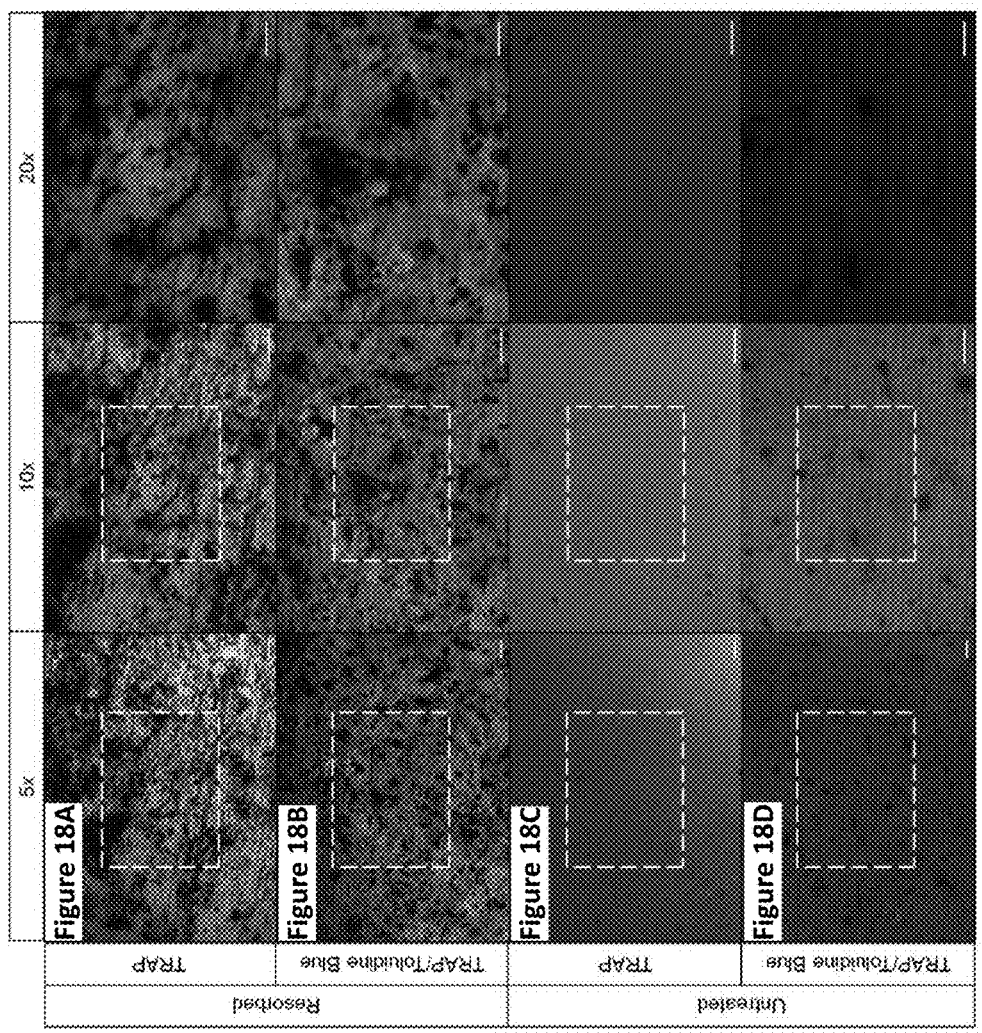

FIG. 18, comprising FIG. 18A through FIG. 18D, is a set of images depicting the result of experiments. Bone wafer resorption pits (FIG. 18A and FIG. 18B) were visualized with TRAP staining solution and toluidine blue and compared to similarly-stained untreated bone wafers (FIG. 18C and FIG. 18D). Approximately 50% of the surface of bone wafers exposed to osteoclast activity is covered with TRAP (FIG. 18A), and roughly 10% of the surface has developing resorption pits (FIG. 18B). Neither TRAP (FIG. 18C) nor resorption pits (FIG. 18D) exist on unexposed bone wafers. Successive images show 5×, 10×, and 20× magnification, and dashed boxes indicate area of next-greatest magnification; scale bars for 5× and 10× are 100 μm, and scale bar for 20× is 50 μm.

Figures 19A, 19B, 19C, 19D:
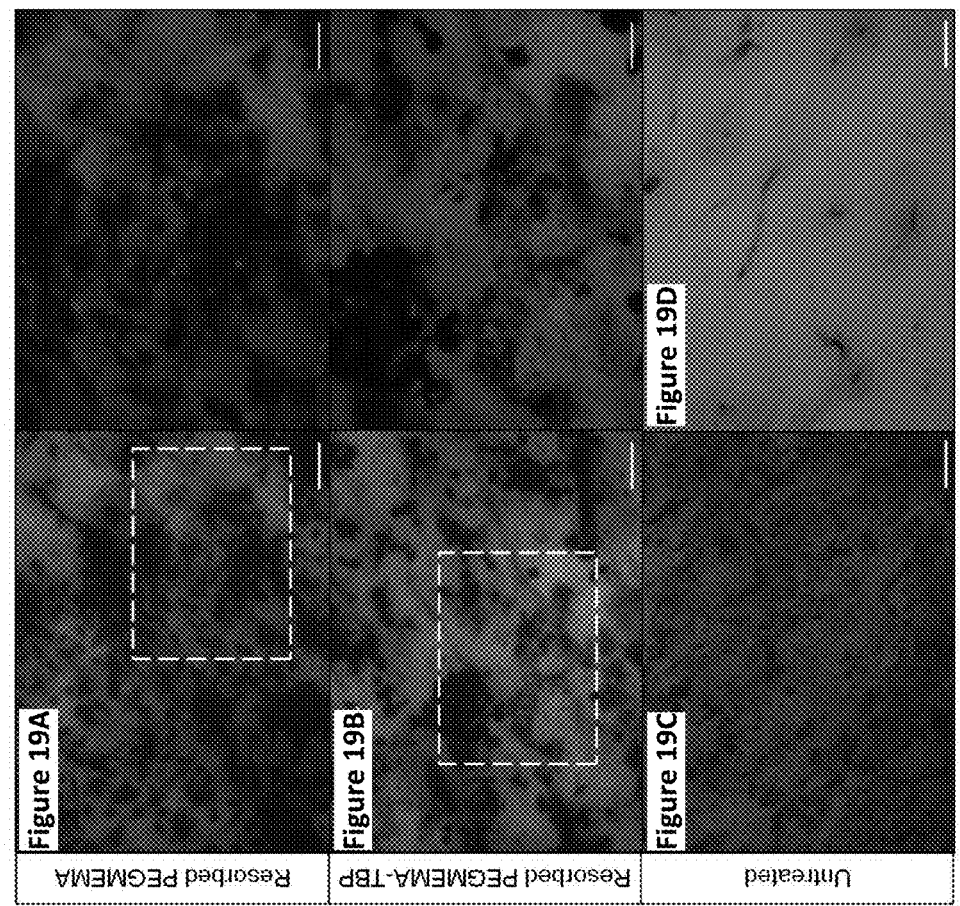

FIG. 19, comprising FIG. 19A through FIG. 19D, is a set of images depicting the results of experiments. Fluorescently-labeled PEG (FIG. 19A and FIG. 19C) and TBP-functionalized polymer therapeutics (FIG. 19B and FIG. 19D) were applied to TRAP/toluidine blue-stained resorbed (FIG. 19A and FIG. 19B) and untreated (FIG. 19C and FIG. 19D) bone wafers. Alone, PEG did not localize to resorption pits (FIG. 19A), but TBP-functionalized polymer therapeutics localized to areas of the bone corresponding to resorption pits (FIG. 19B). Localization was specific to the incorporation of TBP and resorption pits; neither PEG alone (FIG. 19C) nor TBP-functionalized polymer therapeutics (FIG. 19D) showed affinity to untreated bone. Images are 10× magnification, and dashed boxes indicate the area of 20× magnification seen to the right of (FIG. 19A) and (FIG. 19B). Scale bar for 10× is 100 μm, and scale bar for 20× is 50 μm.

Figure 20:
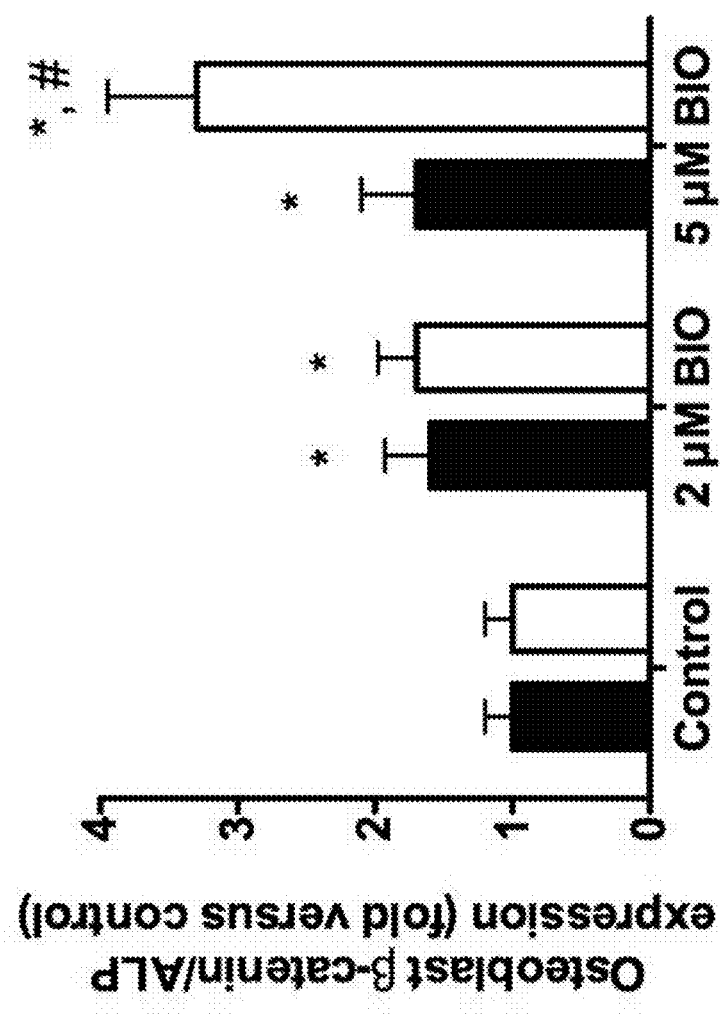

FIG. 20 is a graph demonstrating that BIO treatment of osteoblasts for 24 hours increased both β-catenin (black) levels just after treatment and ALP production (white), analyzed 7-days after treatment. Data represents mean±standard deviation for 3 trials. *p<0.05 versus control, #p<0.05 versus 2 μM BIO (n=5).

Figure 21:
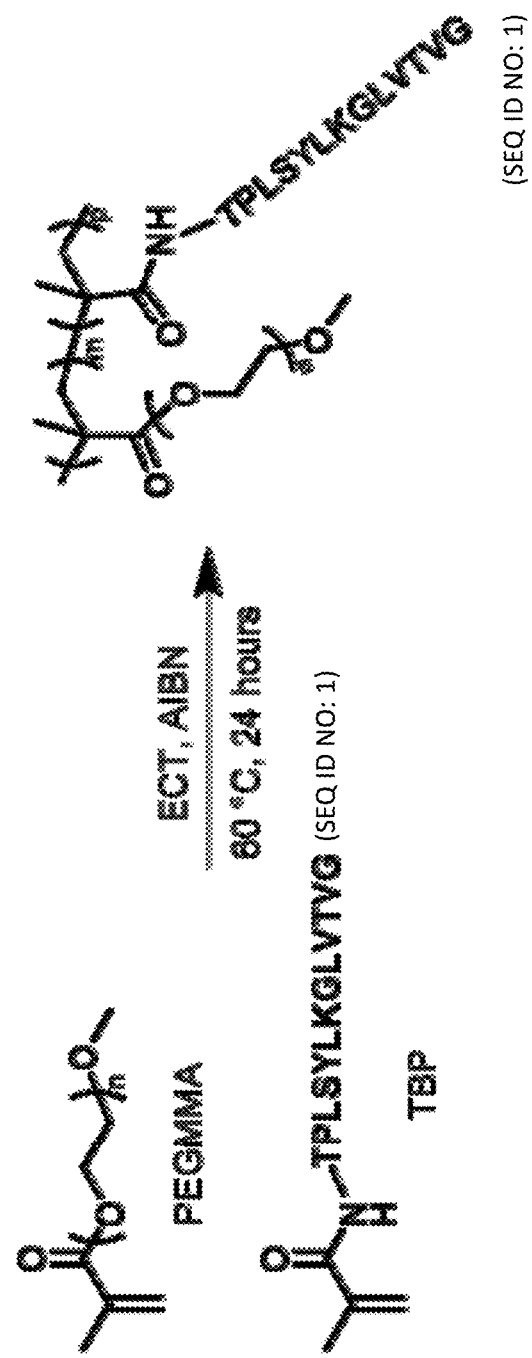

FIG. 21 depicts a polymerization scheme for synthesizing random peptide-functionalized PEG polymers. PEG monomethyl ether methacrylate (PEGMMA) and methacrylamide-functionalized TBP dissolved in 0.5 M dimethylformamide (DMF) were copolymerized using 1, 4-cyano-4-(ethylsulfanylthiocarbonyl) sulfanyl pentanoic acid (ECT) and azobisisobutyronitrile (AIBN) as the RAFT chain transfer agent (CTA) and initiator, respectively, forming random copolymers. n=4.5, m=40-275, p=0-12.

Figure 22:
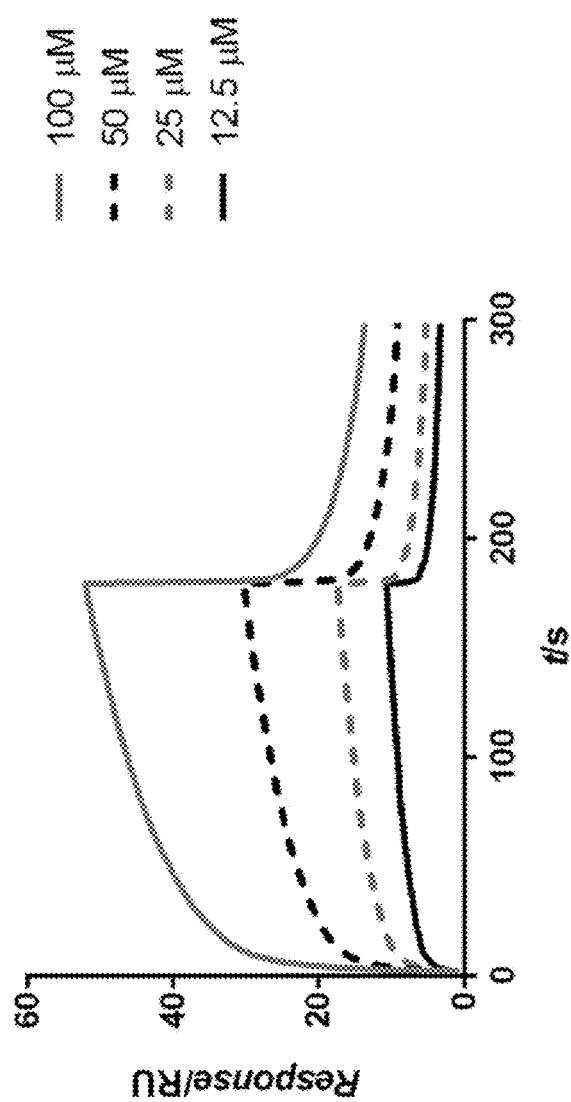

FIG. 22 depicts the results of surface plasmon resonance sensorgram for 10% TBP-functionalized polymer. A positive response indicates affinity for TRAP.

FIG. 23A, FIG. 23B, and FIG. 23C depict the results of surface plasmon resonance sensorgrams for control polymers. None of (FIG. 23A) PEG, (FIG. 23B) 10% SCP-functionalized polymer, or (FIG. 23C) 20% SCP-functionalized polymer show affinity to TRAP, indicated by negative responses.

Figure 24:

FIG. 24 depicts the results of experiments demonstrating the in vitro biocompatibility assessment of peptide-functionalized PEG polymers. Peptides and peptide-functionalized PEG polymers were cytocompatible with osteoclasts and MSCs.

FIG. 25 depicts a series of statistical tables for cell viability experiments. Two-way ANOVA with α=0.05 and Dunnett's post-hoc testing for each treatment vs. control. ns=not significant (p>0.05), *=p≤0.05, =p≤0.01, *=p≤0.001, ****=p≤0.0001.

Figure 26:
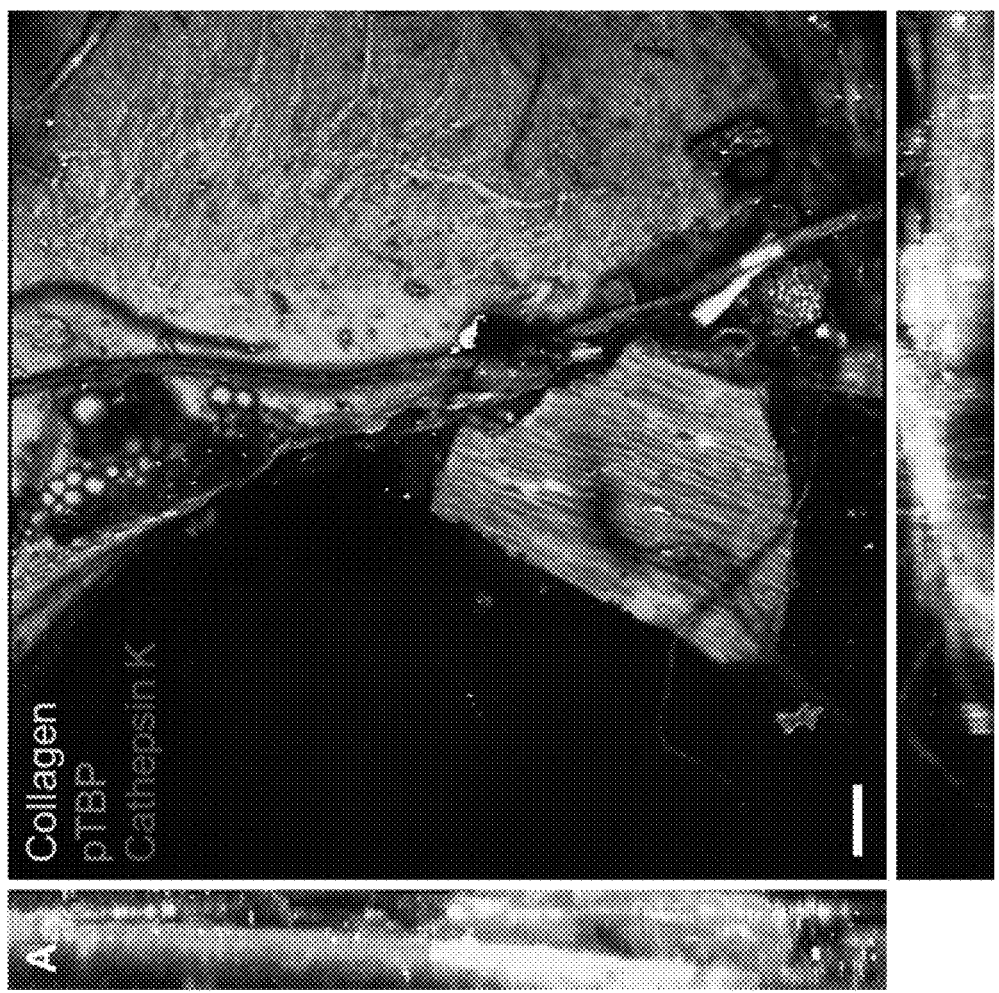

FIG. 26 is an image depicting in vivo assessment of TRAP targeting of peptide-functionalized PEG polymers. Two-photon microscopy shows co-localization of pTBP (green) and cathepsin K (red) along the boney edge (grey) of the defect. Scale bar is 100 μm.

Figure 27:
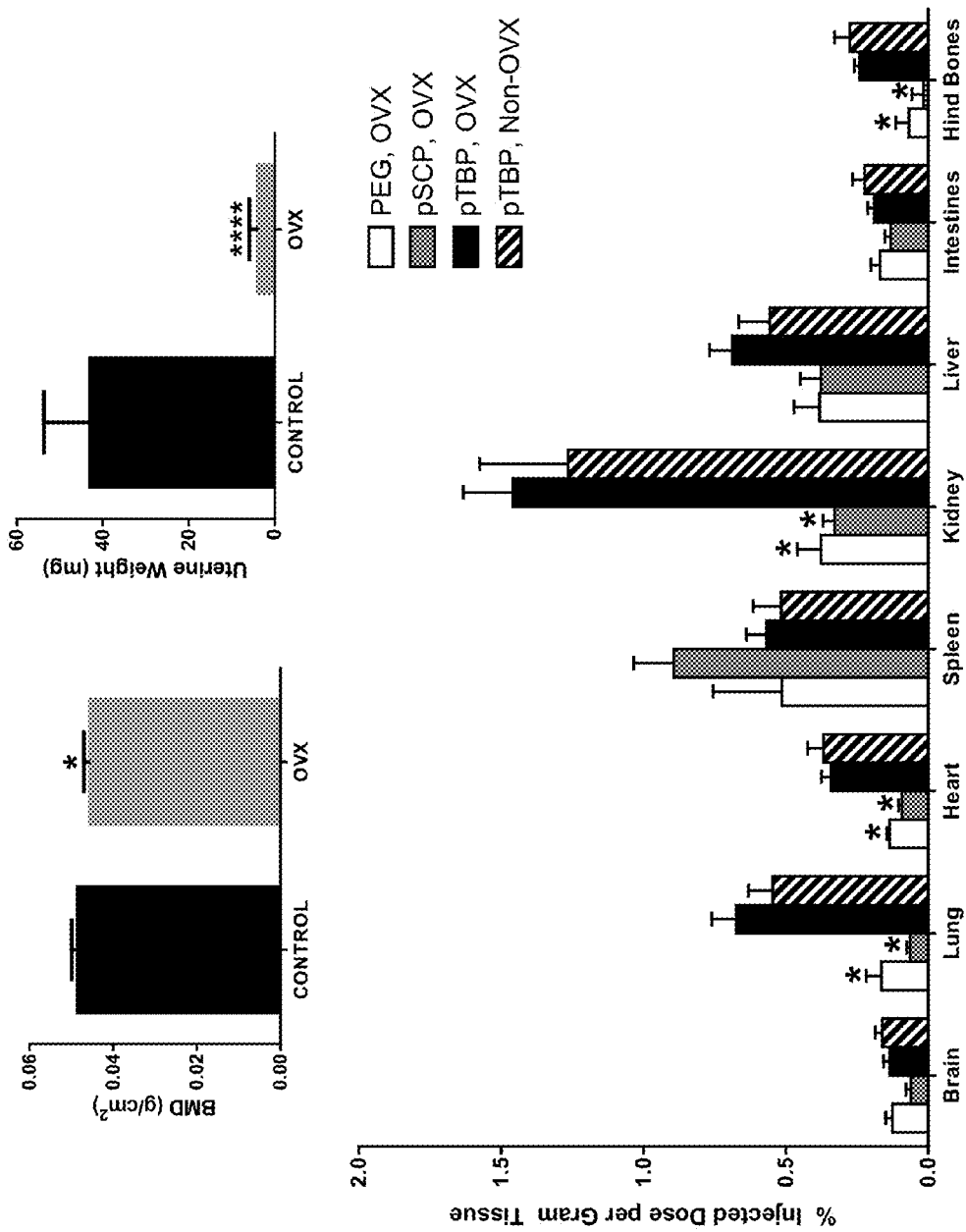

FIG. 27 is a graph showing the results of twenty-four hour biodistribution of peptide-functionalized polymers. *=p<0.05 vs. pTBP, OVX using one-way ANOVA within organ groups.

Figures 28A, 28B:
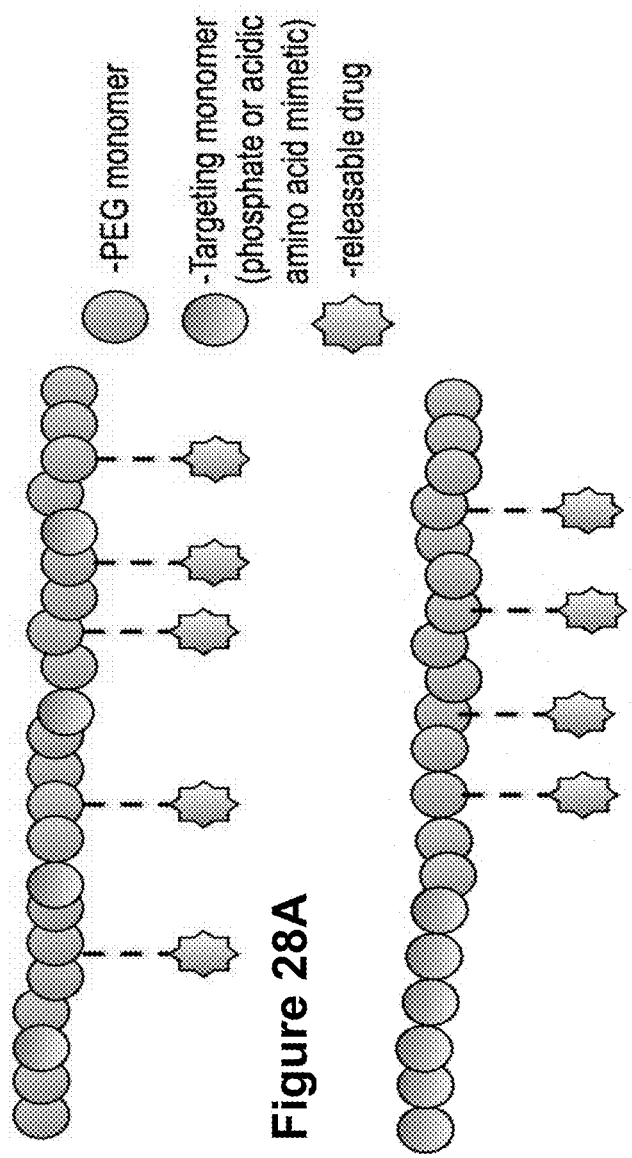
Figures 29A, 29B, 29C, 29D:
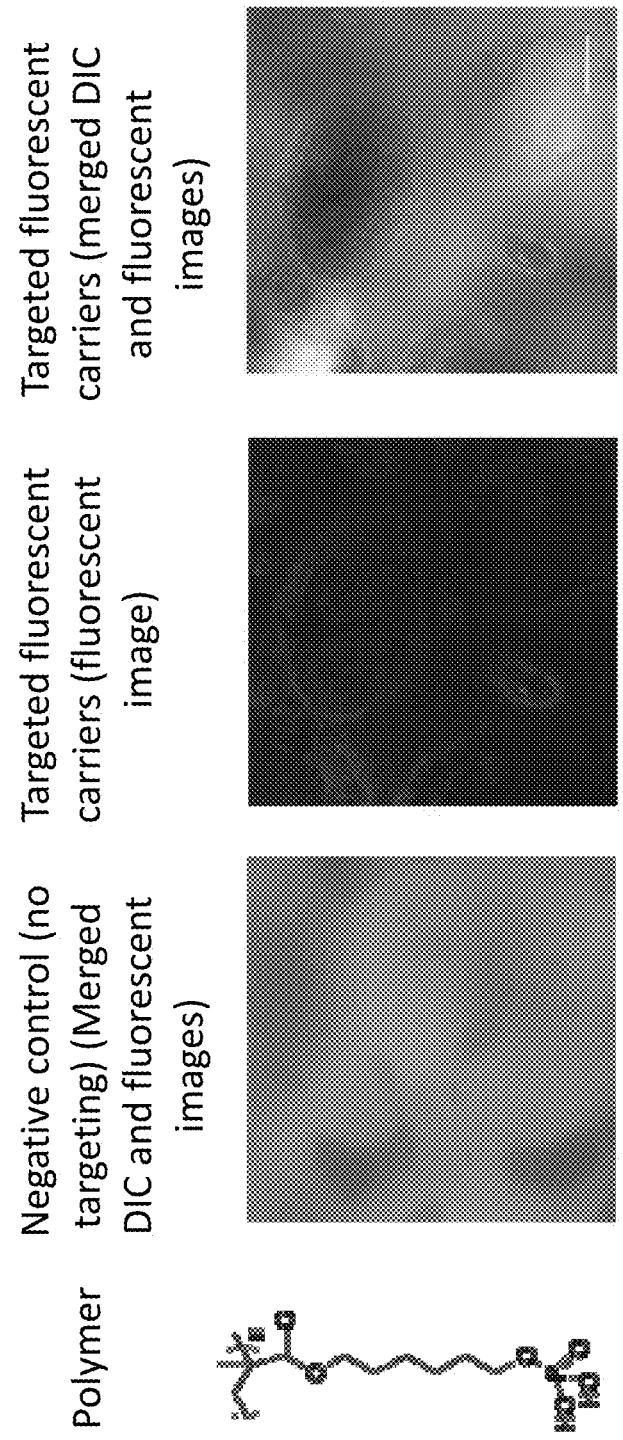

FIG. 28A and FIG. 28B depict illustrations depicting a strategy to develop multivalent bone-targeted polymer therapeutics. Polymers are synthesized using RAFT polymerizations, a simple, reproducible, and scalable method to create highly controlled molecular weights and architectures. Targeting moieties separately presenting phosphates or acidic amino acid mimetics will be incorporated for bone targeting in statistical (FIG. 28A) or block (FIG. 28B) copolymers with poly(ethylene glycol) (PEG) comonomers.

FIG. 29A, FIG. 29B, FIG. 29C, and FIG. 29D depict images demonstrating that RAFT oligomers formulated with synthesized 6-methacryloyloxyhexyl dihydrogen phosphate and copolymerized with fluorescein methacrylate (FIG. 29A, n=10) were recently demonstrated to exhibit general bone homing capabilities (FIG. 29C and FIG. 29D) but control oligomers (RAFT polymers of poly(ethylene glycol) monomethyl ether with copolymerized fluorescein methacrylate) show no accumulation (FIG. 29B). bar=200 μm. Note that punctate fluorescence on the images highlights where polymer is accumulated within 3D bone resorption pits. As these are 3D stacks of images rendered into a 2D image, these areas appear to have greater accumulated polymer.

Figure 30:
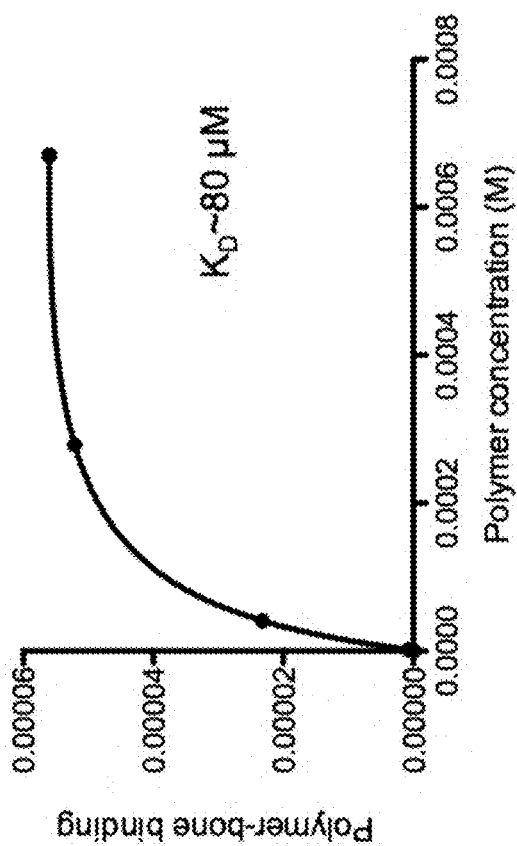

FIG. 30 is a graph demonstrating that Poly(phosphate) oligomers (n=10) mediate binding to bone with high affinity (KD~80 μM).

Figure 31B:
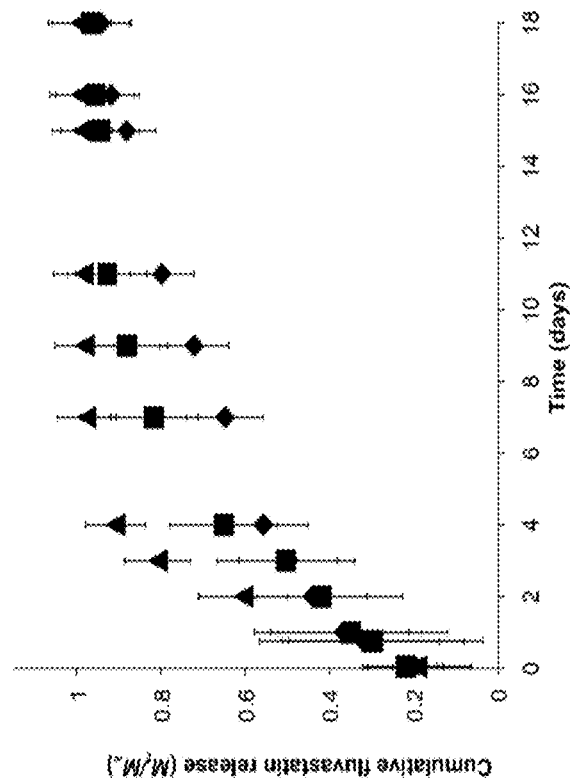
Figure 31A:
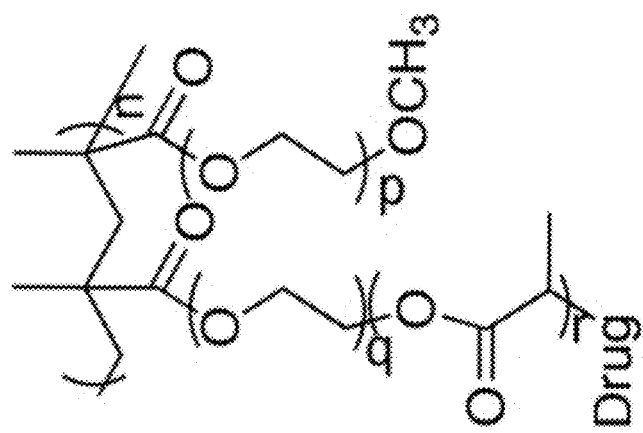

FIG. 31A and FIG. 31B depict the results of experiments demonstrating (FIG. 31A) RAFT architectures with releasable bone drug delivery capabilities. This particular design utilizes poly(ethylene glycol) monomethyl ether as the main component and poly(ethylene glycol) functionalized with degradable ester bonds tethering drugs for delivery. Targeting comonomers are incorporated either in a statistical or block fashion, see FIG. 28A and FIG. 28B. (FIG. 31B) the controlled release of bone-acting drug, fluvastatin, which promotes bone production through upregulation of BMP2, was demonstrated in the context of polymers described in FIG. 31A (Benoit et al., 2007; Benoit et al., 2006). Cumulative release (Mt/M∞) as a function of time and length of lactide tether from polymers (fluvastatin: 2 degradable bonds: diamonds, 4 degradable bonds: squares, 6 degradable bonds: triangles).

Figure 32:
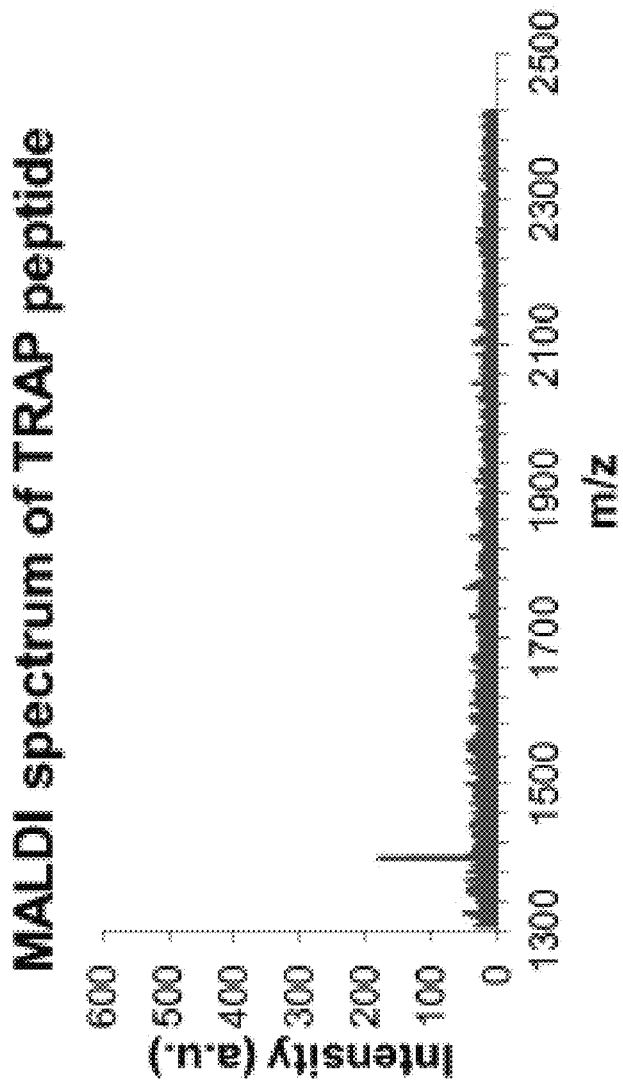

FIG. 32 is a graph depicting the MALDI spectrum of the TRAP peptide, indicating a main peak at 1387 g/mol, which is the molecular weight of the TRAP peptide +K (potassium).

Figure 33:
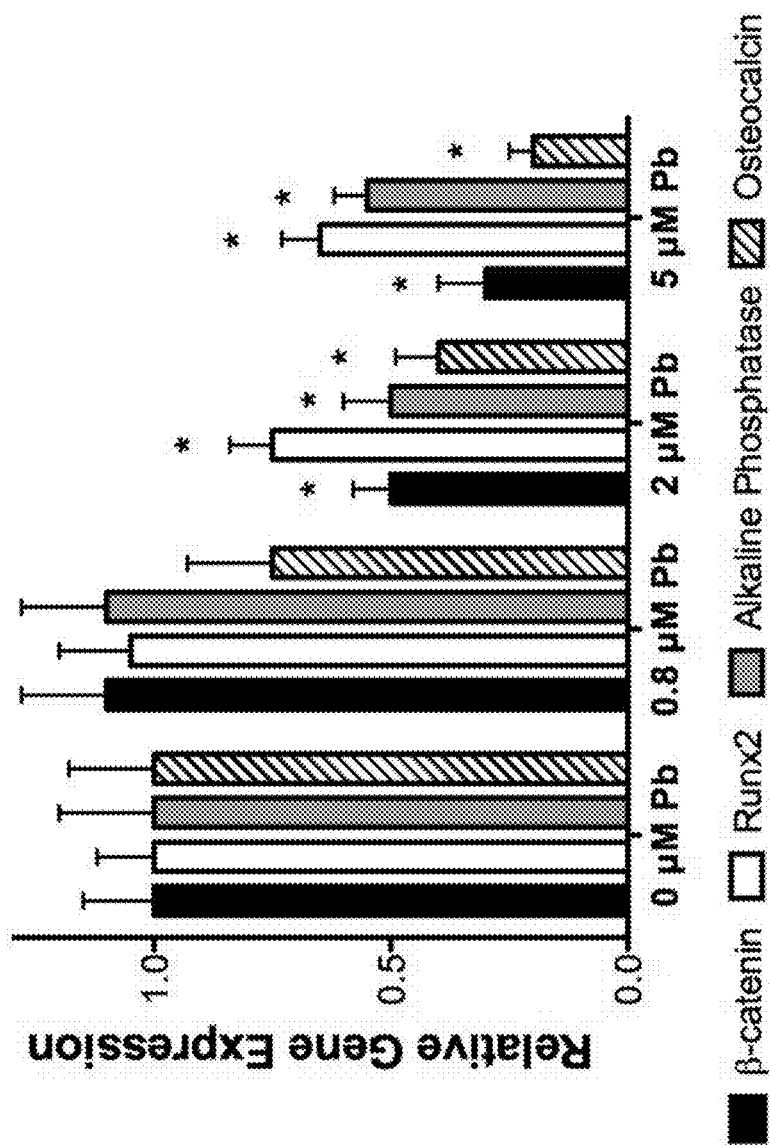

FIG. 33 is a graph demonstrating that Pb suppresses osteoblast β-catenin and osteogenic gene expression after 10 days of lead treatment. Data represent mean±standard deviation, *p<0.05 (n=5).

Figure 34:
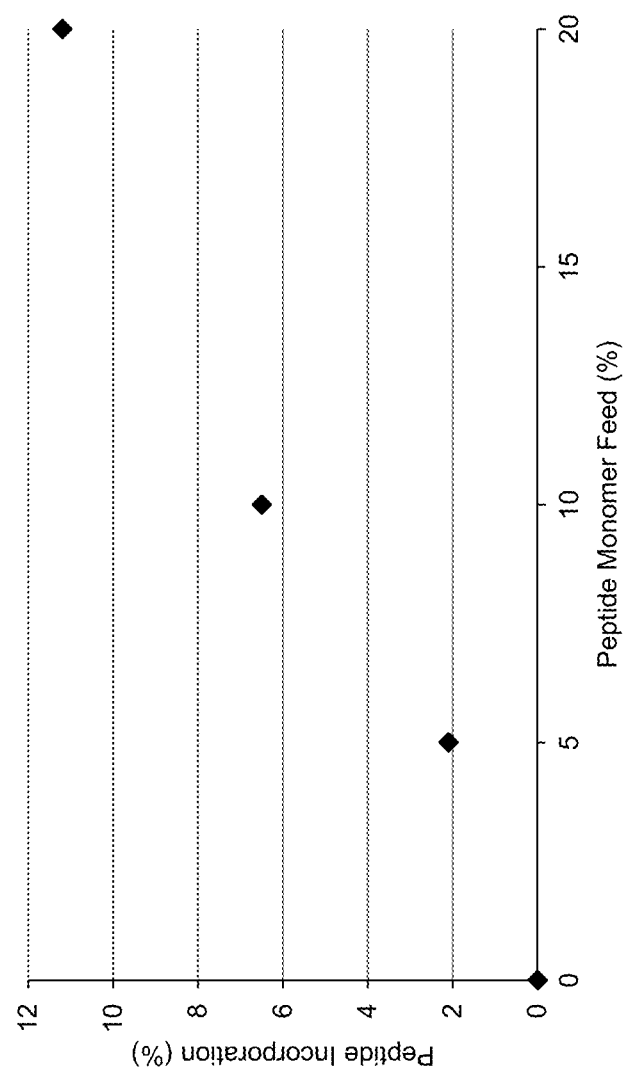

FIG. 34 is a graph demonstrating that polymers were synthesized with different ratios of peptide to PEG monomers. After polymerization and purification the incorporation of peptide was determine through the absorption of the polymers at 280 nm, due to the tyrosine in the peptide sequence.

Figure 35:
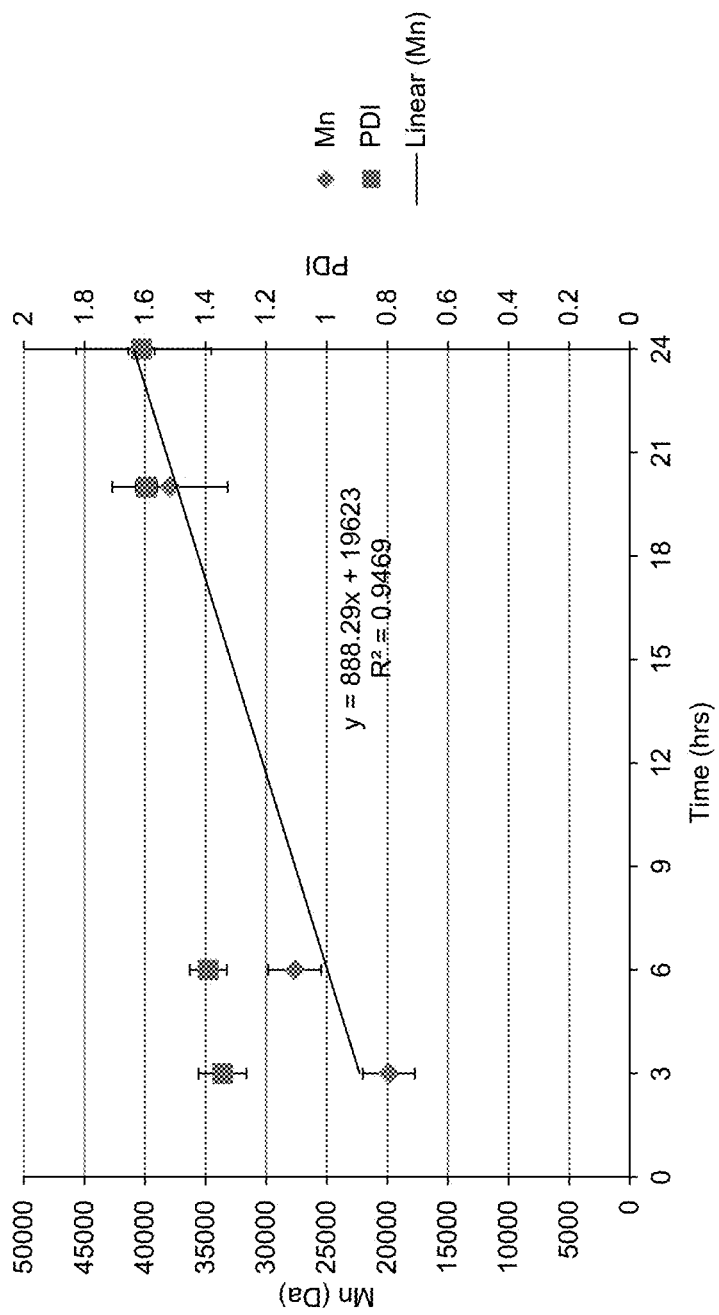

FIG. 35 is a graph demonstrating that PEG300MMA and TRAP binding peptide were combined in a molar ratio of 95:5 and dissolved in an equal weight of DMF. ECT was added at a molar ratio of 150:1, monomers:CTA. AIBN was added at a molar ratio of 10:1, CTA:initiator. Vessels were purged with $N_2$ and reacted at 60° C. Samples were taken at various time points and analyzed via gel permeation chromatography (GPC). (n=3, error bars are standard deviation)

FIG. 36A, FIG. 36B, and FIG. 36C depict the results of experiments demonstrating that exposure to 50 ppm Pb results in a systemic decrease in trabecular bone volume and quality. The middle trabecular region of the third lumbar vertebrae (FIG. 36A), the distal Tb femur region (FIG. 36B) and proximal Tb tibia region (FIG. 36C) were analyzed for bone properties. Representative 3D images are transverse section from water and Pb-exposed groups and were selected based on the median trabecular bone volume (BV/TV) of each group. Graphs show significant reductions in bone volume compared to total volume (BV/TV) and trabecular number (1/mm). Trabecular spacing and connective density were also analyzed (data not shown) but showed statistically significant increases and decreases, respectively, in spacing and density in Pb-treatment groups. Data represent mean±standard deviation for 9 rats/group, *p<0.05 compared to controls.

Figure 37A:
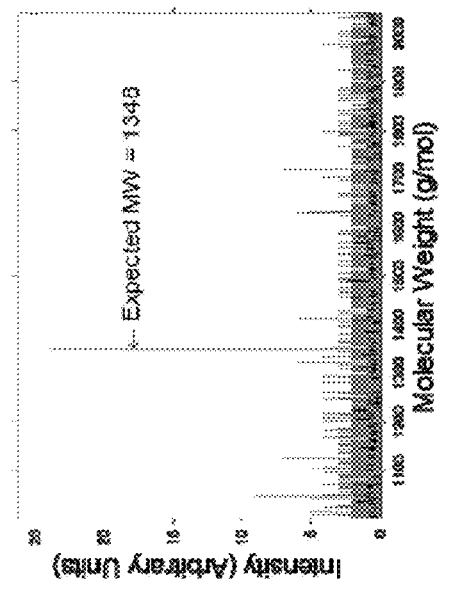
Figure 37B:
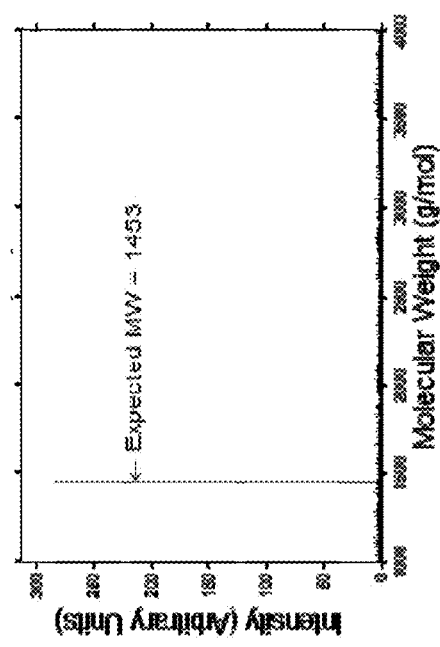

FIG. 37A and FIG. 37B depict the MALDI-ToF spectra of tartrate resistant acid phosphatase (TRAP) binding peptide (TBP) (FIG. 37A) and TBP methacrylamide (TBPM) (FIG. 37B). Peptides were produced using solid phase synthesis and were analyzed after cleavage from resin.

Figure 38A:
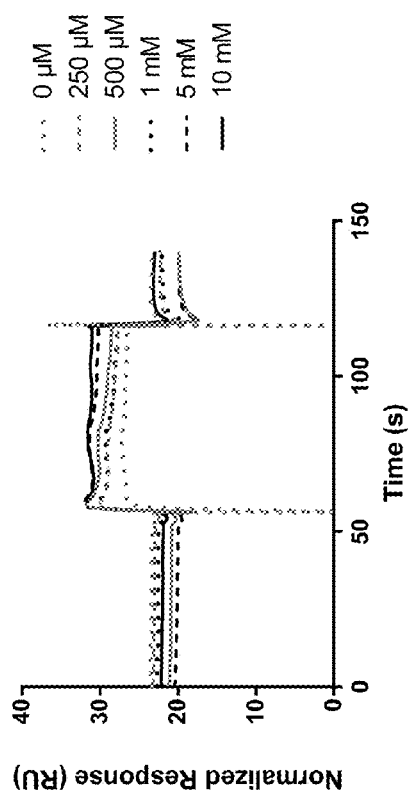
Figure 38B:
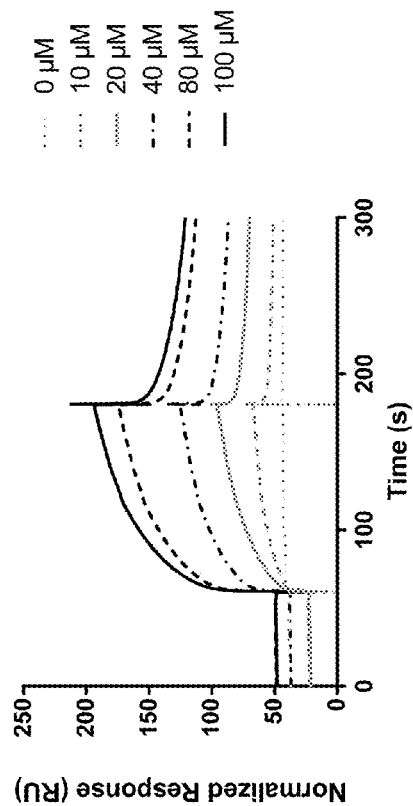

FIG. 38A and FIG. 38B depict representative binding and dissociation curves for 0% (FIG. 38A) and 5% (FIG. 38B) TBP-functionalized polymers. Sharp spikes mark the transition from running buffer to sample and vice versa. The association of the sample during injection is followed by a disassociation period, which is more pronounced and prolonged in the polymer samples. A positive relationship is observed between the response and concentration.

Figure 39B:
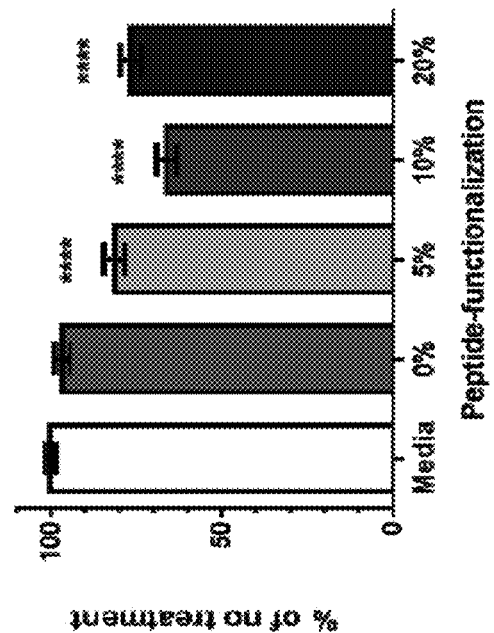
Figure 39A:
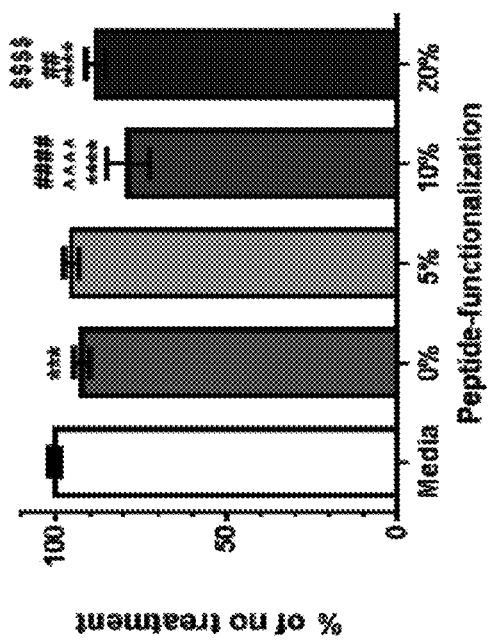

FIG. 39A and FIG. 39B depict the results of experiments demonstrating the cytocompatability of 0.1 mM (FIG. 39A) and 10 mM (FIG. 39B) of peptide-functionalized polymers and control polymers. Data were collected after 7 days of continuous treatment and normalized to the control group. (*p<0.001, **p<0.0001 vs media, ~~~p<0.0001 vs 0%, ##p<0.01, ####p<0.0001 vs 5%, $$$$ p<0.0001 vs 10% by one-way ANOVA with Tukey's multiple comparison test, n=6, error bars are standard deviation).

Figure 40:
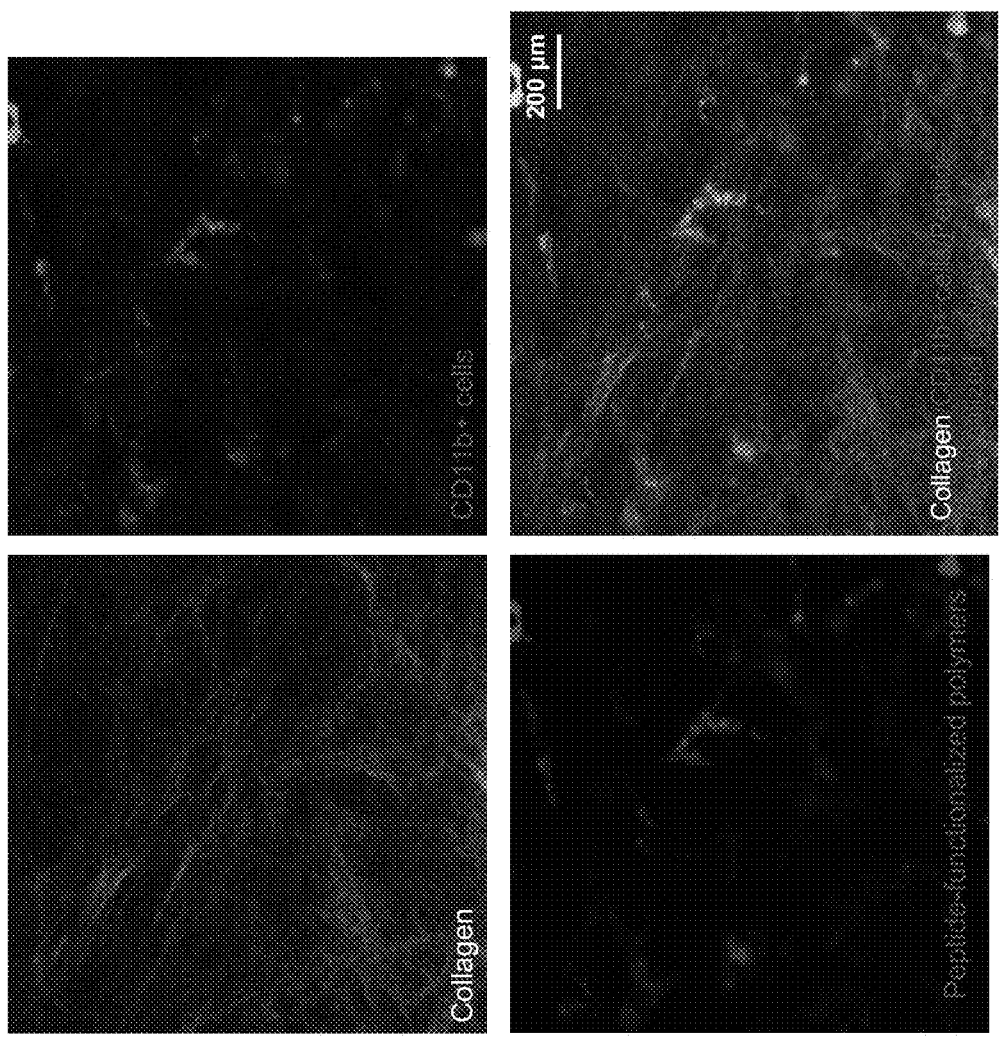

FIG. 40 depicts the results of experiments studying colocalization of peptide-functionalized polymers with osteoclasts and remodeling bone. A 0.5 mm hole was drilled into the calvaria of a 3-month-old mouse, and a glass window was sutured in place on the skull. Three days post-procedure, the mouse was given an intraperitoneal injection of 100 µL of 26.5-nM PEGMEMA-TBP dissolved in sterile saline (0.11 mg total, approximately 5.5 mg/kg) and returned to its cage. After 30 min, the mouse was anesthetized, and the edges of the defect were imaged through the calvarial window using an Olympus Fluoview multiphoton microscope with second harmonic generation at 25× magnification. Images were captured with and without the use of a Kalman filter to reduce the noise from breathing.

Figure 41:
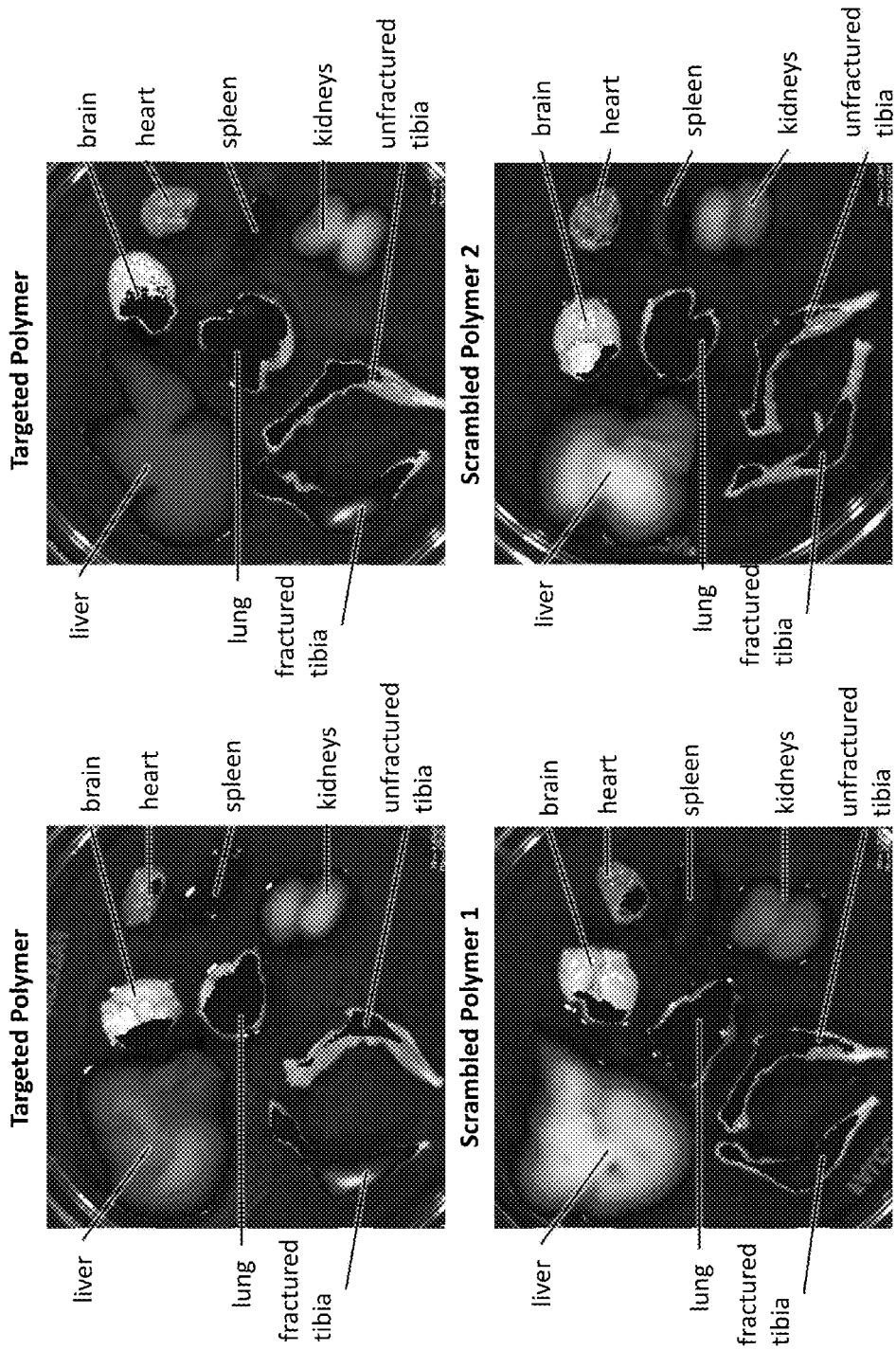

FIG. 41 depicts the results of experiments demonstrating the biodistribution of p(PEG-co-TBP) in organs and bone. The injection was made 5 days following fracture, and biodistribution was investigated 24 hours post injection.

Figure 42:
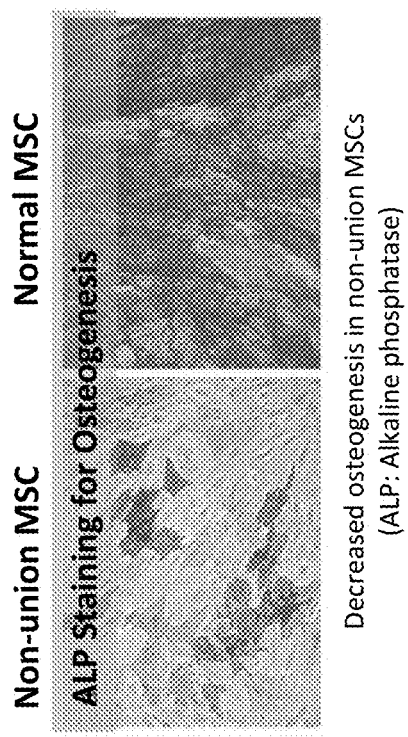

FIG. 42 depicts decreased osteogenesis in non-union fracture mesenchymal stem cells (MSCs) as shown by alkaline phosphatase staining.

FIG. 43A depicts the decreased level of β-catenin activity in non-union fracture MSCs.

FIG. 43B depicts the GSK3β inhibitor XXVII and its effect on active nuclear β-catenin levels in MSCs.

Figure 44A:
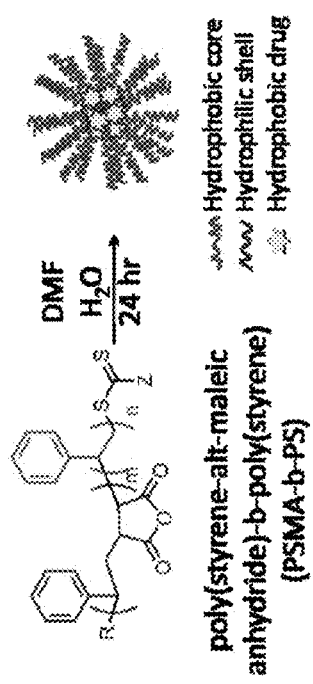

FIG. 44A depicts the loading of a hydrophobic drug into the core of an amphiphilic nanoparticle (NP).

Figure 44B:
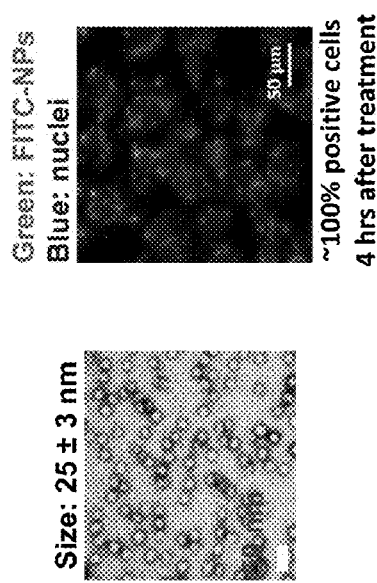

FIG. 44B depicts the results of experiments demonstrating the intracellular accessibility of NPs labeled with fluorescein isothiocyanate (FITC) fluorophore and incubated with MSCs.

FIG. 45 depicts the results of experiments demonstrating potent cellular uptake of NPs and validating β-catenin agonism of NP delivered GSK3β inhibitor XXVII in cells were treated with free GSK3β inhibitor XXVII and NP delivered GSK3β inhibitor XXVII.

Figure 46:
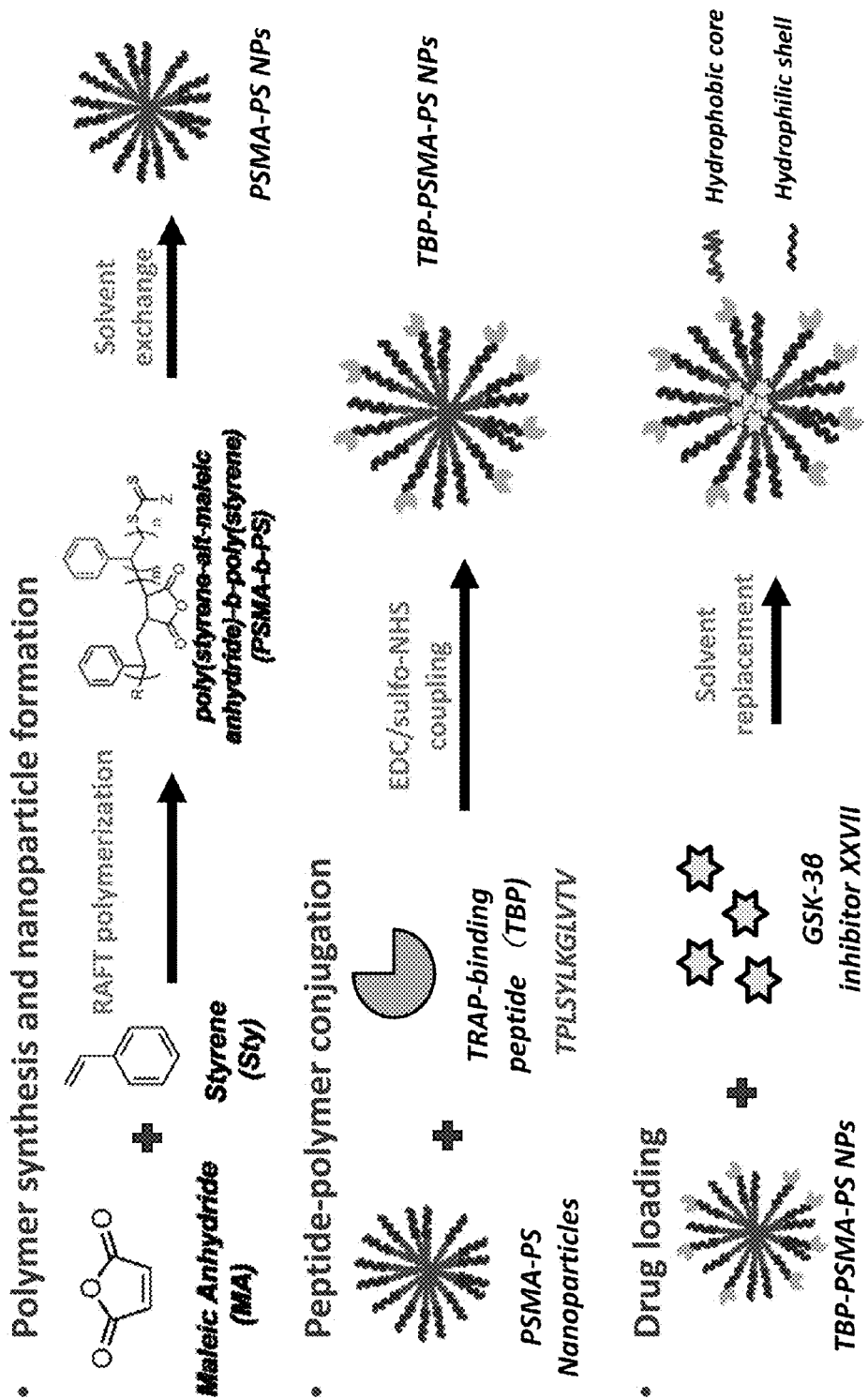

FIG. 46 depicts the process of polymer synthesis, NP formation, peptide-polymer conjugation, and loading of GSK3β inhibitor XXVII.

FIG. 47 depicts the characterization of exemplary NP.

Figure 48:
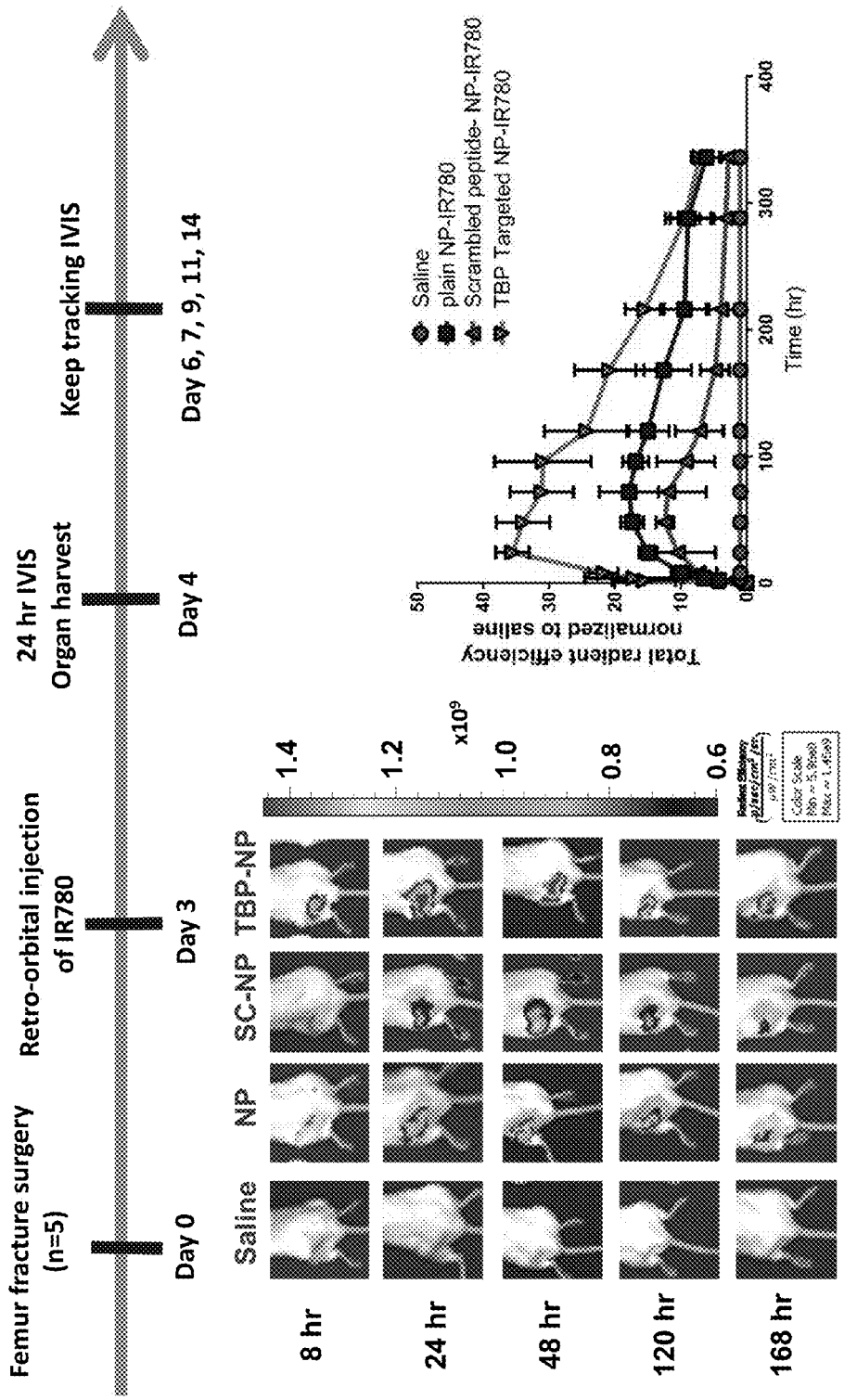

FIG. 48 depicts the results of experiments demonstrating the in vivo accumulation of systemically administered NPs, wherein IVIS imaging was used to visually investigate the fracture-targeting effect of peptide-conjugated NPs.

Figure 49:
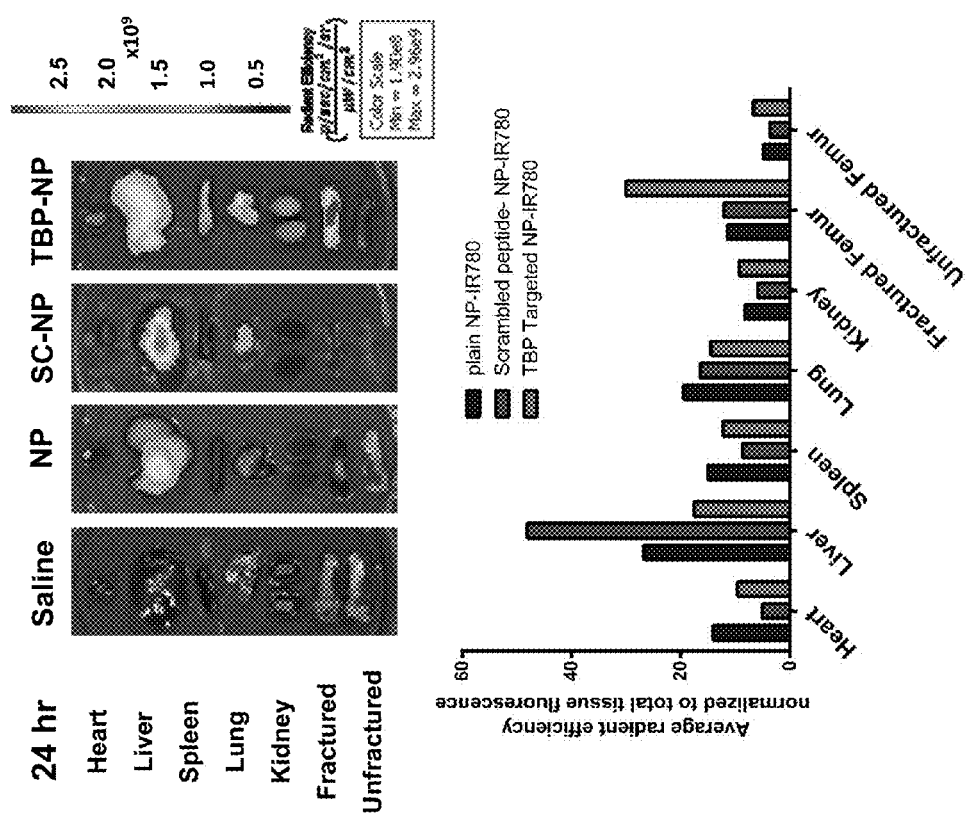

FIG. 49 depicts the results of experiments demonstrating the tissue distribution of TBP-NP using the fluorescence intensity of TBP-NP delivered IR780.

Figure 50:
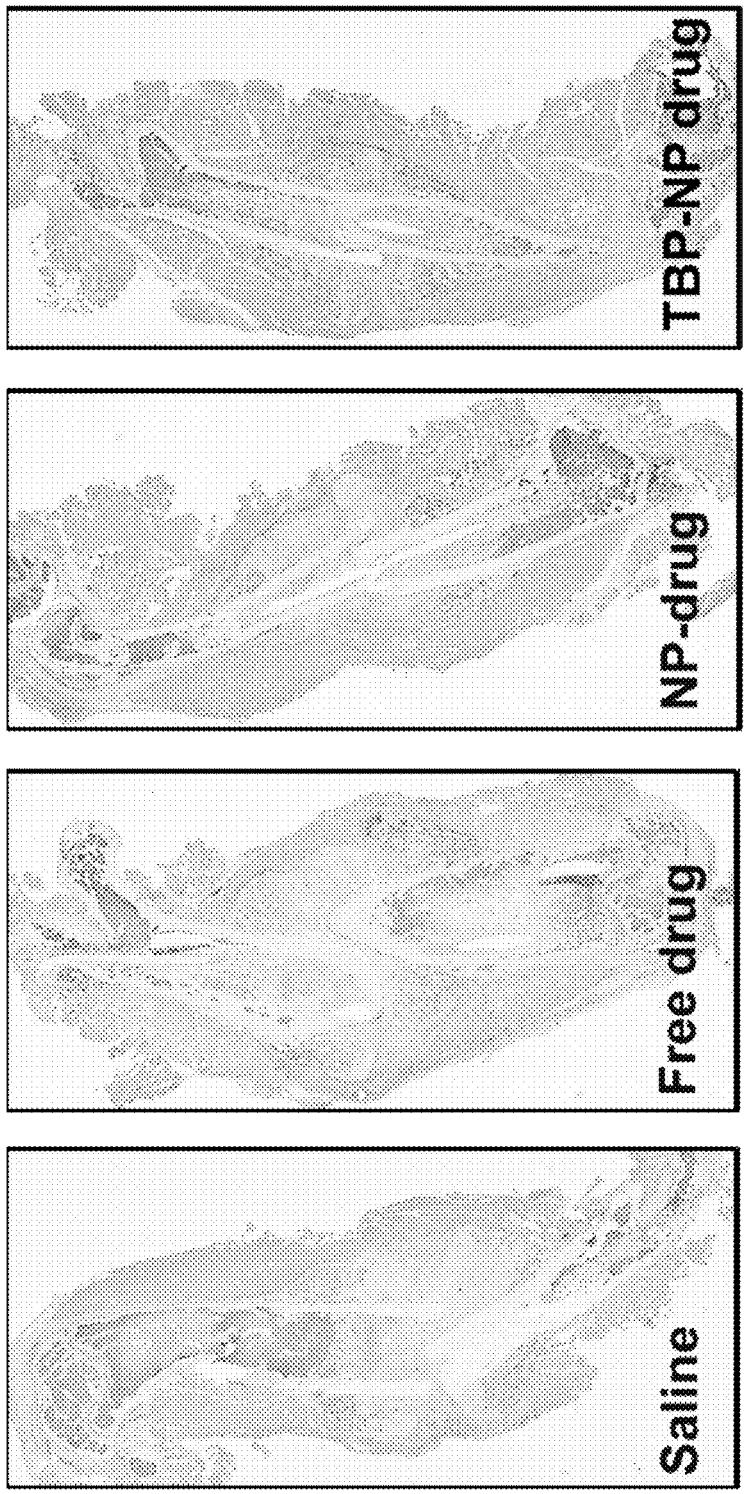

FIG. 50 depicts histological sections of fracture callus from LacZ reporter mice 14 days after injection with GSK3β inhibitor XXVII.

Figure 51:
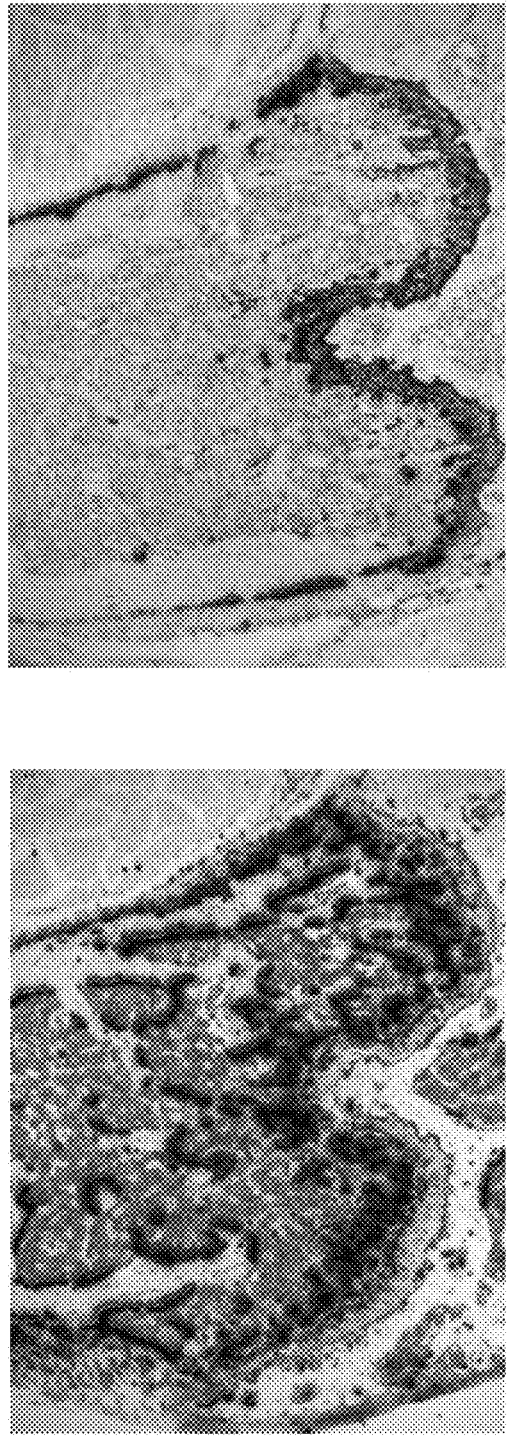

FIG. 51 depicts the loss of Collagen 1 expression in bone, indicating inhibition of functional osteoblastic cells in a murine model of blast-crisis chronic myelogenous leukemia.

Figure 52A:
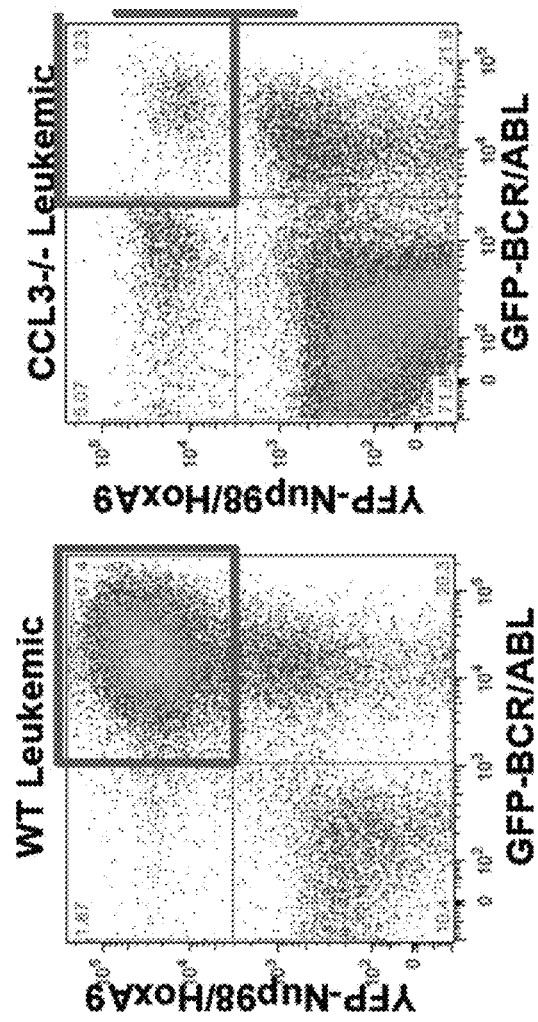

FIG. 52A depicts flow cytometric plots from the bone marrow of WT and CCL3−/− primary leukemic cells indicated by boxes.

Figure 52B:
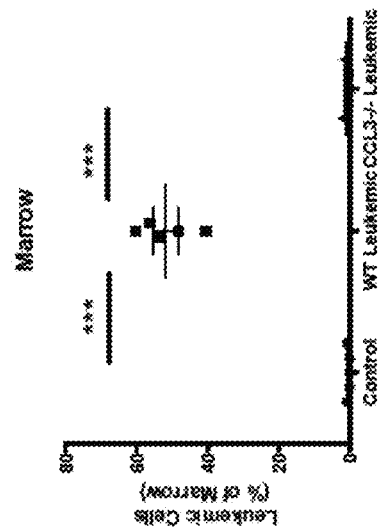

FIG. 52B depicts the percent of leukemic cells in the bone marrow of secondary recipients of WT or CCL3−/− leukemic cells.

Figure 53:
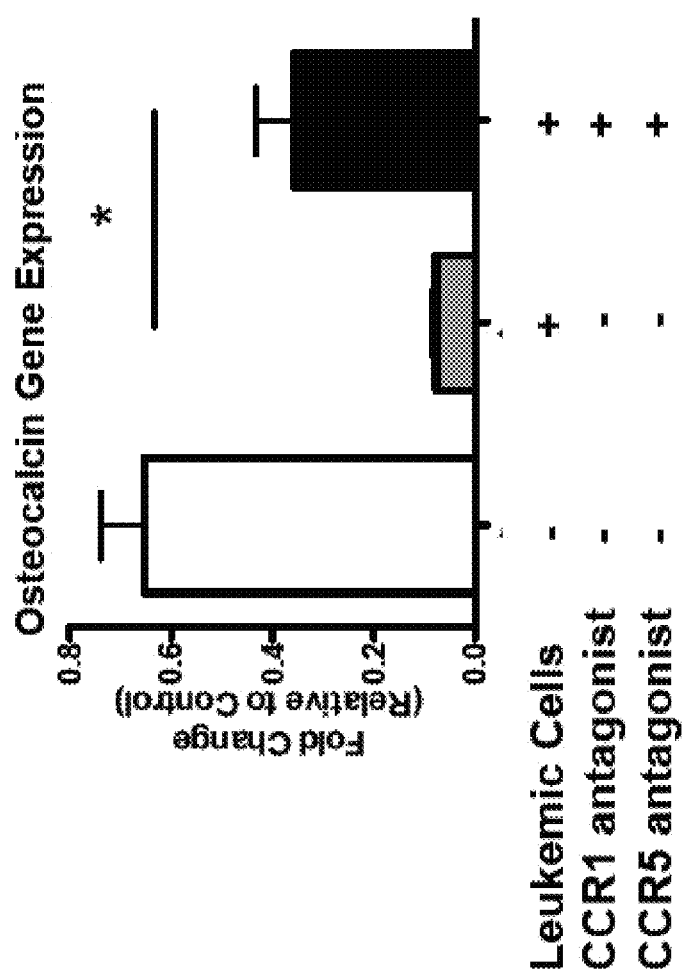

FIG. 53 depicts the results of experiments demonstrating that inhibition of CCR1 and CCR5 rescues leukemia mediated loss of the osteoblastic marker Osteocalcin in vitro. *p≤0.05 by student's t-test.

Figure 54:
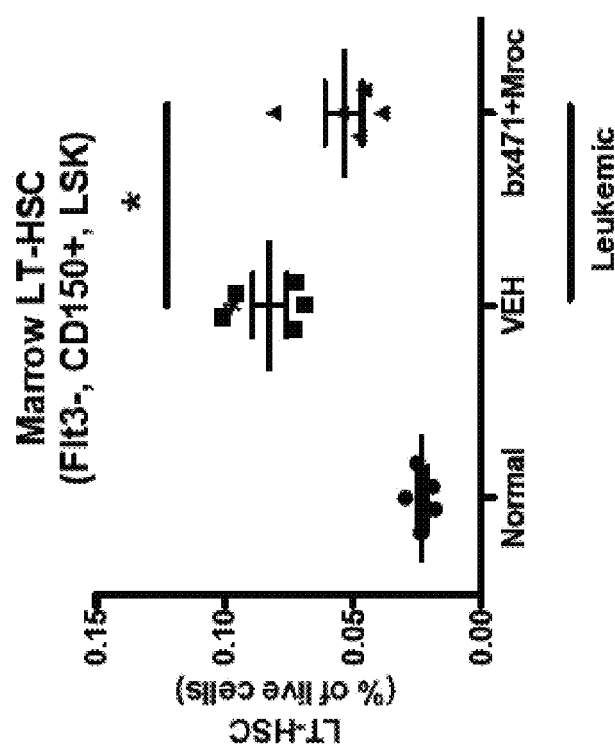

FIG. 54 depicts the results of experiments demonstrating that inhibition of CCR1 and CCR5 partially rescues increased numbers of HSCs in the marrow of leukemic mice. *p≤0.05 by student's t-test.

Figure 55:
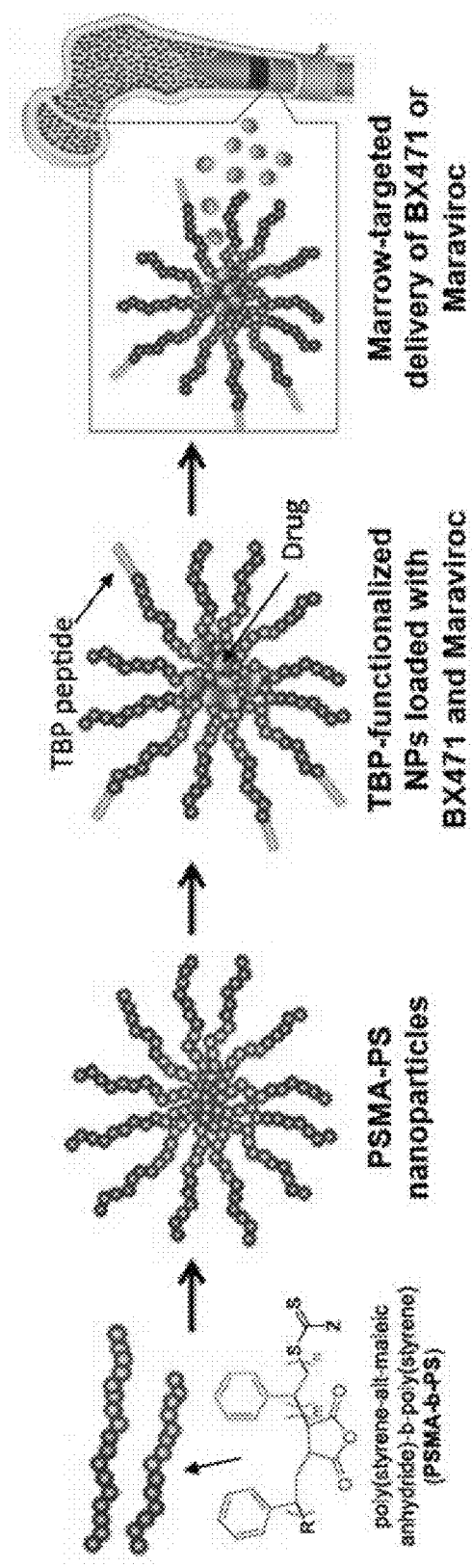

FIG. 55 is an illustration depicting the loading of BX471 and Maraviroc into TBP-functionalized NPs allowing for marrow-targeted drug delivery.

Figure 56:
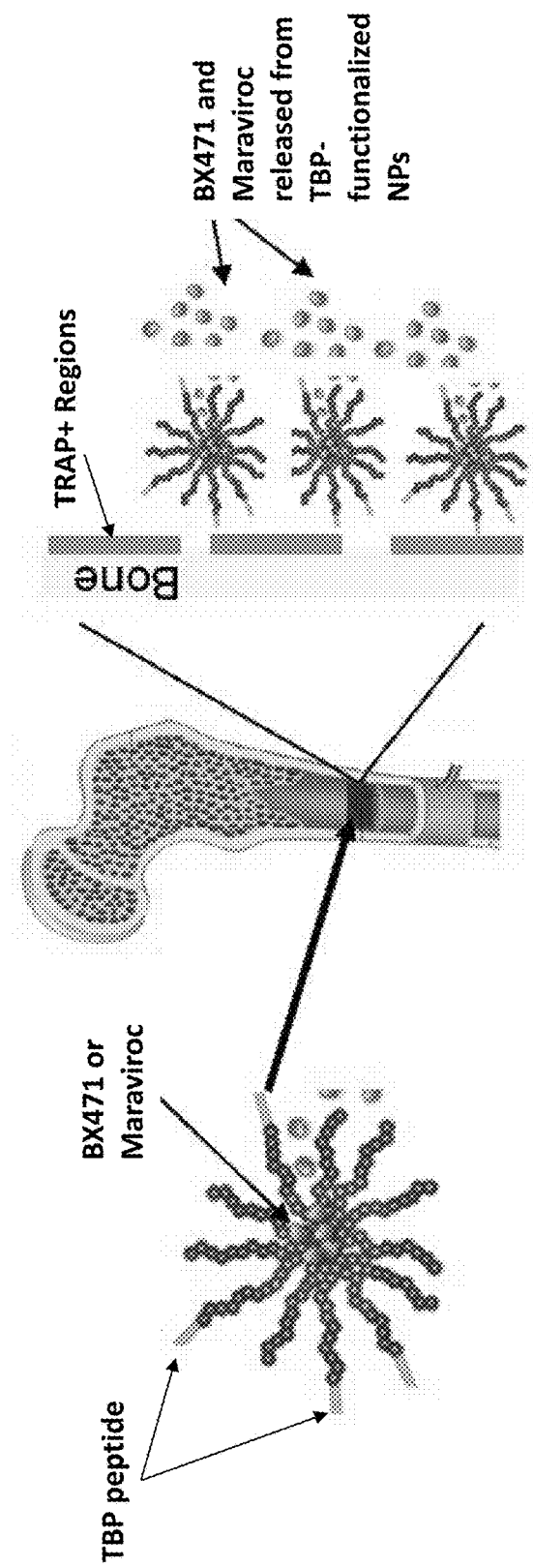

FIG. 56 is an illustration depicting TBP-functionalized nanoparticles (NPs) loaded separately with BX471 (CCR1 inhibitor) and Maraviroc (CCR5 inhibitor) will accumulate at TRAP+ regions of bone within the bone marrow. There they will release BX471 and Maraviroc into the bone marrow over the course of several (10+) days increasing the local drug concentrations above what would be achievable with free drug delivery. Delivery of these drugs to the bone marrow in a targeted manner increases support for normal hematopoiesis while decreasing support for leukemia stem cells.

Figure 57:
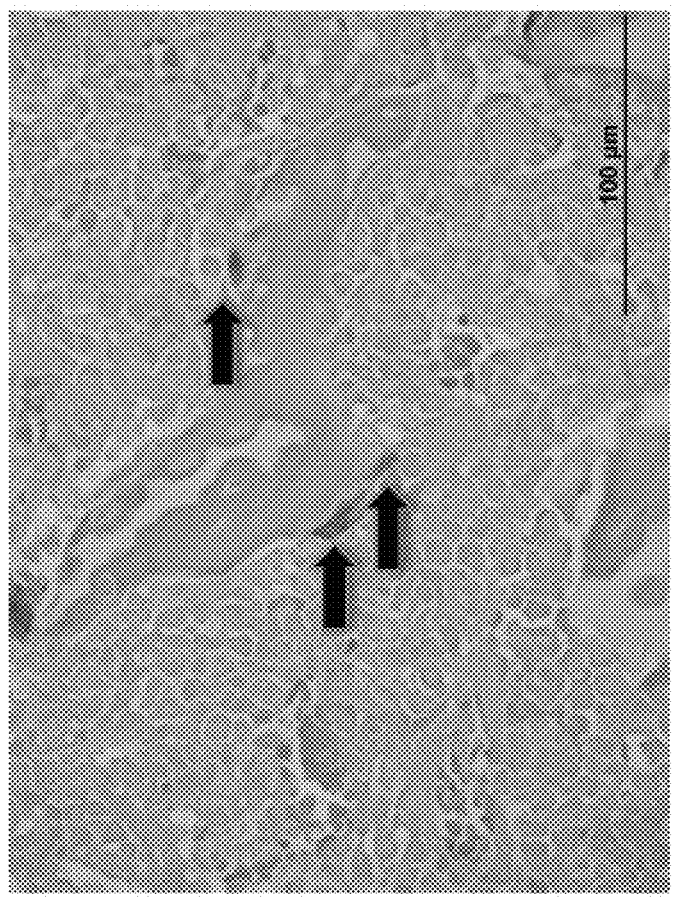

FIG. 57 depicts the histochemical analysis of the bone marrow from leukemic mice. TRAP activity results in pink stain, indicated by black arrows.

Figure 58:
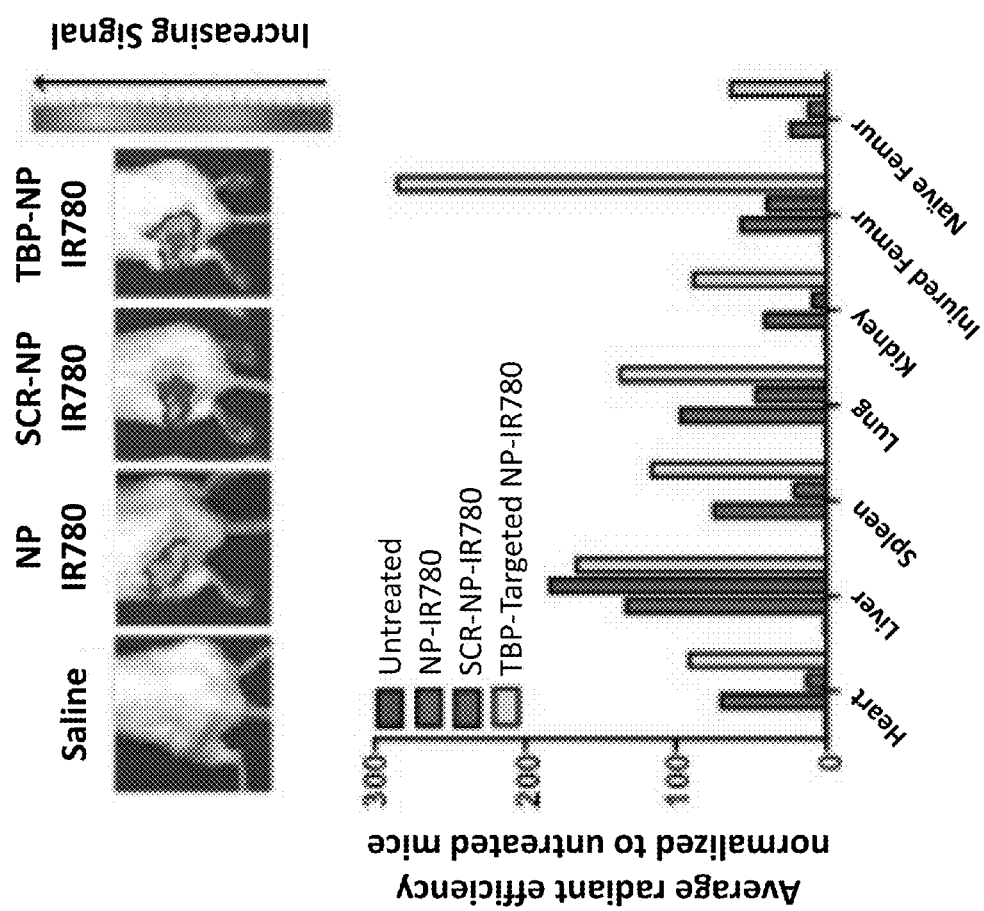

FIG. 58 depicts the results of experiments demonstrating that TBP-functionalized NPs accumulate in the TRAP-rich fracture sites versus other tissues. Data are for 24 hours post-injection (4 mg/kg; 0.35 mg/kg IR780).

Figure 59:
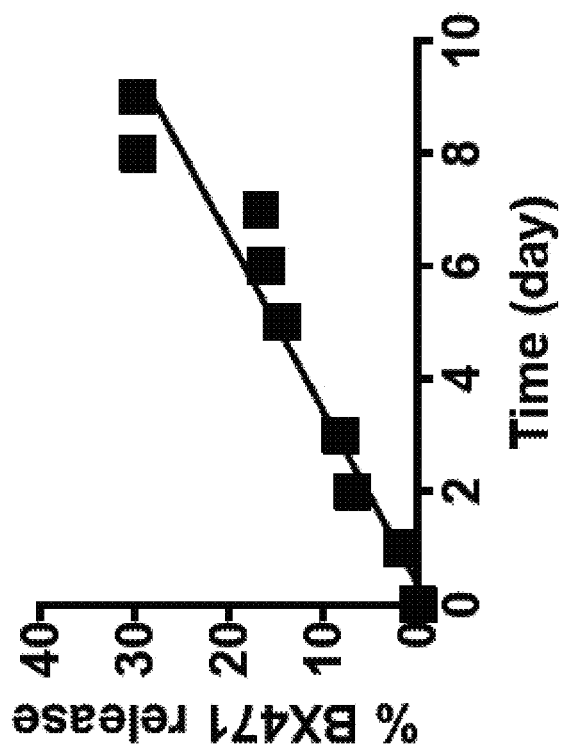

FIG. 59 depicts the results of experiments demonstrating that micelle-mediated BX471 release is zero-order and sustained for over 10 days (n=1 independent experiment; incomplete release is observed as time course of release was unknown).

Figure 60:
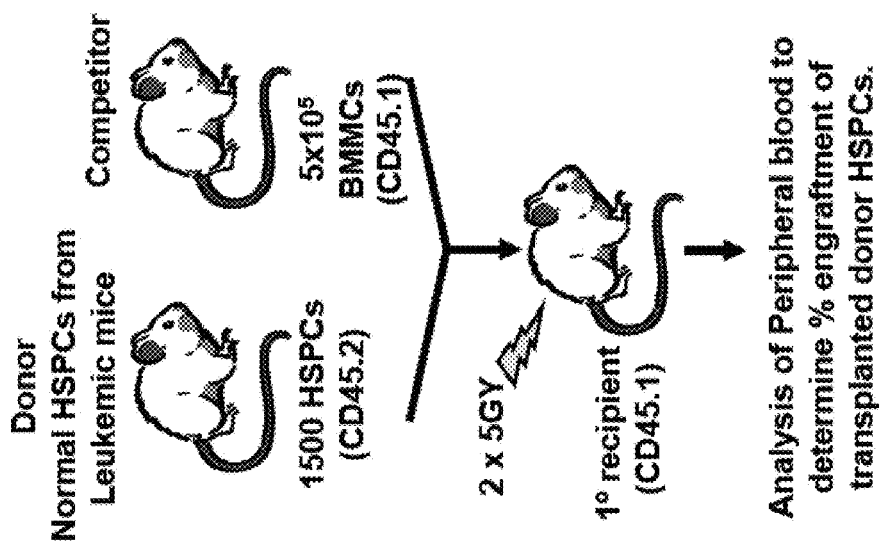

FIG. 60 is an illustration depicting CD45.2+ donor cells being mixed with CD45.1+ competitor cells and transplanted into a CD45.1+ recipient mouse. Peripheral blood is analyzed at 4, 8, 12, and 16 weeks to determine % engraftment of donor cells.

DETAILED DESCRIPTION

The present invention relates generally to compositions and methods for increasing bone formation. The invention can be used, for example, to restore bone, increase bone formation, promote bone regeneration in conditions including, but not limited to osteoporosis, osteonecrosis, osteomyelitis, osteoarthritis, Paget's disease, bone fracture, bone allograft rejection, bone autograft rejection, wear-debris induced osteolysis, and cancer of the bone. In certain embodiments, the invention provides controlled and local delivery of a therapeutic agent to a site in need of bone formation. In certain embodiments, the invention provides controlled and local delivery of a therapeutic agent to a site in need of bone-targeted treatment.

In one embodiment, the invention provides a composition comprising a therapeutic-tethered macromer to induce bone formation. In certain embodiments, the therapeutic-tethered macromer comprises a therapeutic agent comprising at least one of a nucleic acid, protein, peptide, small molecule, aptamer, antagonist, or peptidomimetic that promotes bone formation. In a particular embodiment, the therapeutic agent comprises an inhibitor of glycogen synthase kinase 3 beta (GSK3β). In one embodiment, the therapeutic-tethered macromer comprises one or more degradable tethers that provide controlled release of the therapeutic agent. Non-limiting examples of the degradable tether include, but are not limited to: an ester, a thioester, an orthoester, an amide, an anhydride, a disulfide bond, or a peptide sequence. For example, in one embodiment, the degradable tether comprises lactide bonds.

In one embodiment, the composition comprises a hydrogel comprising the therapeutic-tethered macromer. For example, in one embodiment, the therapeutic-tethered macromer is incorporated within a hydrogel. In certain embodiments, the degradation of the tethers of the therapeutic-tethered macromer releases the therapeutic agent from the hydrogel.

In one embodiment, the composition comprises a bone-homed particle comprising the therapeutic-tethered macromer. For example, in certain embodiments, the bone-homed particle comprises a targeting domain that directs the particle to a site in need of bone formation or bone treatment. In one embodiment, the targeting domain comprises a peptide sequence that targets the particle to a site in need of bone formation or bone treatment (e.g. bone resorption pit, bone marrow). In one embodiment, the particle is a polymer comprised of monomers, some of which are modified to target to bone and/or to resorption pits. In certain embodiments, degradation of the tethers of the therapeutic-tethered macromer releases the therapeutic agent from the bone-homed particle.

In one embodiment, the invention provides a method for treating osteoporosis, osteonecrosis, osteomyelitis, osteoarthritis, Paget's disease, bone allograft rejection, bone autograft rejection, wear-debris induced osteolysis, bone fracture, bone cancer, and other diseases of the bone. The method comprises administering an effective amount of the therapeutic-tethered macromer at a site in need of bone formation or bone treatment. The method provides controlled local delivery of the therapeutic agent at a site in need of bone formation or bone treatment.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type, might be abnormal for a different cell or tissue type.

As used here, "biocompatible" refers to any material that, when implanted in a mammal, does not provoke an adverse response in the mammal. A biocompatible material, when introduced into an individual, is not toxic or injurious to that individual, nor does it induce immunological rejection of the material in the mammal. "Biocompatible" also refers to a property of a composition characterized by its degradation products or its in vivo degradation products being not, or at least is minimally and/or reparably, injurious to living tissue; and/or not, or at least minimally and controllably, causing an immunological reaction in living tissue.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "effective amount" or "therapeutically effective amount" of a compound is that amount of compound that is sufficient to provide a beneficial effect to the subject to which the compound is administered. An "effective amount" of a delivery vehicle is that amount sufficient to effectively bind or deliver a compound.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "gel" refers to a three-dimensional polymeric structure that itself is insoluble in a particular liquid but which is capable of absorbing and retaining large quantities of the liquid to form a stable, often soft and pliable, but always to one degree or another shape-retentive, structure. When the liquid is water, the gel is referred to as a hydrogel. Unless expressly stated otherwise, the term "gel" will be used throughout this application to refer both to polymeric structures that have absorbed a liquid other than water and to polymeric structures that have absorbed water, it being readily apparent to those skilled in the art from the context whether the polymeric structure is simply a "gel" or a "hydrogel."

In the context of the present invention, the following abbreviations for the commonly occurring nucleic acid bases are used: "A" refers to adenosine; "C" refers to cytosine; "G" refers to guanosine; "T" refers to thymidine; "U" refers to uridine.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared and multiplied by 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of a composition includes, e.g., subcutaneous (s.c.), intravenous (i.v.), intramuscular (i.m.), or intrasternal injection, or infusion techniques. "Enteral" administration of a composition generally refers to delivery involving any part of gastrointestinal tract including oral delivery and rectal delivery. Parenteral and enteral administration have systemic effects.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences that are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

In the context of the present invention, the following abbreviations for the commonly occurring amino acids are used: "A" refers to alanine; "C" refers to cysteine; "D" refers to aspartic acid; "E" refers to glutamic acid; "F" refers to phenylalanine; "G" refers to glycine; "H" refers to histidine; "I" refers to isoleucine; "K" refers to lysine; "L" refers to leucine; "M" refers to methionine; "N" refers to asparagine; "P" refers to proline; "Q" refers to glutamine; "R" refers to arginine; "S" refers to serine; "T" refers to threonine; "V" refers to valine; "W" refers to tryptophan; "Y" refers to tyrosine. These abbreviations are not to be confused with the abbreviations for nucleic acid bases, it being readily apparent to those skilled in the art from the context whether the letter indicates an amino acid or nucleic acid base.

As used herein, the term "polymer" refers to a molecule composed of repeating structural units typically connected by covalent chemical bonds. The term "polymer" is also meant to include the terms copolymer and oligomers.

As used herein, the term "polymerization" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combination thereof. A polymerization reaction may consume between about 0% and about 100% of the at least one functional group available in the system. In one embodiment, polymerization of at least one functional group results in about 100% consumption of the at least one functional group. In another embodiment, polymerization of at least one functional group results in less than about 100% consumption of the at least one functional group.

The term "graft polymer," as used herein, means and includes a polymer that includes a main polymer block and at least one side polymer segment as a branch in a side chain of the main polymer block. The at least one side polymer segment may be structurally distinct from the main polymer block.

As used herein, the term "polymer segment" means and includes a grouping of multiple monomer units of a single type (i.e., a homopolymer segment) or multiple types (i.e., a copolymer segment) of constitutional units into a continuous region of a polymer block that are of a length that is insufficient for microphase separation to inherently occur with other segments in the same block type.

As used herein, the term "block copolymer" means and includes a polymer composed of chains where each chain contains two or more polymer blocks as defined above and at least two of the blocks are of sufficient segregation strength (e.g., $\chi N > 10$) for those blocks to phase separate. A wide variety of block polymers are contemplated herein including diblock copolymers (i.e., polymers including two polymer blocks), triblock copolymers (i.e., polymers including three polymer blocks), multiblock copolymers (i.e., polymers including more than three polymer blocks), and combinations thereof.

The term "brush polymer" as used herein refers to a polymer architecture in which oligomer or polymer chains are terminally tethered to a polymer bone at a high density. In certain instances, overcrowding of the chains results in the chains stretching away from the polymer backbone thereby forming a brush-like architecture. In some embodiments, the polymer backbone and/or oligomer/polymer chains are reversible addition-fragmentation chain transfer (RAFT) polymers.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence that is required for expression of a gene product operably linked to the promoter/regulatory sequence. In some instances, this sequence may be the core promoter sequence and in other instances, this sequence may also include an enhancer sequence and other regulatory elements that are required for expression of the gene product. The promoter/regulatory sequence may, for example, be one that expresses the gene product in a tissue specific manner.

As used herein, the term "patient," "subject," "individual," and the like are used interchangeably herein, and refer to any animal, or cells thereof, whether in vitro or in situ, amenable to the methods described herein. In certain non-limiting embodiments, the patient, subject or individual is a mammal, non-limiting examples of which include a primate, dog, cat, goat, horse, pig, mouse, rat, rabbit, and the like, that is in need of bone formation or bone treatment. In some embodiments of the present invention, the subject is a human being. In such embodiments, the subject is often referred to as an "individual" or a "patient." The terms "individual" and "patient" do not denote any particular age.

As used herein, the phrase "a site in need of bone formation," "a site in need of bone treatment," and "a site in need of bone formation or bone treatment" refers to any site or region within a subject that, for any reason, is in need of bone formation or bone treatment. For example, in certain embodiments, the site is a region that has experienced bone loss or bone disease. In certain embodiments, a site in need of bone formation or bone treatment is a "resorptive pit" which is a cavity within bone formed by osteoclasts. In certain embodiments, "a site in need of bone formation or bone treatment" refers to a site that has received an acute injury.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

A "vector" is a composition of matter that comprises an isolated nucleic acid and that can be used to deliver the isolated nucleic acid to the interior of a cell. Numerous vectors are known in the art, including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds that facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates generally to compositions and methods for increasing bone formation in a subject. The invention can be used, for example, to restore bone, increase bone formation, promote bone regeneration in conditions including, but not limited to osteoporosis, osteonecrosis, osteomyelitis, osteoarthritis, Paget's disease, bone allograft rejection, bone autograft rejection, wear-debris induced osteolysis, bone cancer, bone fractures, and the like.

In one embodiment, the invention provides a composition comprising a therapeutic-tethered macromer to induce bone formation. In certain embodiments, the therapeutic-tethered macromer comprises a therapeutic agent comprises at least one of a nucleic acid, protein, peptide, small molecule, aptamer, antagonist, or peptidomimetic that promotes bone formation. In a particular embodiment, the therapeutic agent comprises an inhibitor of glycogen synthase kinase 3 beta (GSK3β). In one embodiment, the therapeutic-tethered macromer comprises one or more degradable tethers that provide controlled release of the therapeutic agent. The present invention is partly based on the development of a controlled release therapeutic-tethered macromer comprising a GSK3β inhibitor tethered to a polymer. In one embodiment, the GSK3β inhibitor is the small molecule, 6-bromoindirubin-3'oxime (BIO). In one embodiment, the GSK3β inhibitor is the small molecule, 3-amino-6-{4-[(4-methyl-1-piperazinyl)sulfonyl]phenyl}-N-(3-pyridinyl)-2-pyrazinecarboxamide (hereinafter, "GSK3β inhibitor XXVII"). The therapeutic-tethered macromer comprising the degradable tethers are used to controllably deliver active therapeutic agent at local sites in the subject. For example, degradation of ester bonds allows for release of BIO or GSK3β inhibitor XXVII from the polymer to a site in need of bone formation or bone treatment. The tethered therapeutic-tethered macromers described herein can be incorporated into a variety of drug delivery compositions to provide local delivery.

In one embodiment, the composition comprises a hydrogel comprising the therapeutic-tethered macromer. For example, in one embodiment, the therapeutic-tethered macromer is polymerized, or copolymerized with one or more polymers, to form a hydrogel. In certain embodiments, the degradation of the tethers of the therapeutic-tethered macromer releases the therapeutic agent from the hydrogel. The hydrogel may comprise any known biopolymers and/or synthetic polymers known in the art. In a particular embodiment, the therapeutic-tethered macromer is covalently attached to hydrogel components such that the therapeutic-tethered macromer is incorporated within the hydrogel.

In one embodiment, the composition comprises a bone-homed particle comprising the therapeutic-tethered macromer. The bone-homed particle may comprise a liposome, microparticle, nanoparticle, micelle, polymer, brush polymer, copolymer, and the like. For example, in certain embodiments, the bone-homed particle comprises a targeting domain that directs the particle to a site in need of bone formation or bone treatment. In certain embodiments, a site in need of bone formation or bone treatment is a site of bone resorption (i.e. a resorption pit) or a site of bone disease. The bone targeting domain may comprise a nucleic acid, peptide, antibody, small molecule, organic molecule, inorganic molecule, and the like that targets the particle to a site in particular need of the therapeutic agent. In one embodiment, the targeting domain specifically binds to tartrate-resistant acid phosphatase (TRAP). For example, in one embodiment a monomer of the particle comprise a phosphate (e.g. 6-methacryloyloxyhexyl dihydrogen phosphate), which targets the particle to bone. In one embodiment, a monomer of the peptide comprises an acidic amino acid mimetic, which targets the particle to resorptive pits (i.e. a site in need of bone formation or bone treatment). In certain embodiments, the particle comprises multivalent targeting, wherein the particle comprises multiple targeting mechanisms described herein. In one embodiment, the bone-homed particle is a brush polymer. In one embodiment, the bone-homed particle is a polymeric composition comprising the therapeutic-tethered macromer and a bone targeting domain. In certain embodiments, degradation of the tethers of the therapeutic-tethered macromer releases the therapeutic agent from the bone-homed particle, thereby allowing the therapeutic agent to act at the site in need of bone formation or bone treatment. In one embodiment, the bone-homed particle comprises a copolymer in the form of a micelle or nanoparticle. In another embodiment, the bone-homed particle comprises a brush polymer. In another embodiment, the bone-homed particle comprises a nanoparticle encapsulating a therapeutic.

In certain embodiments, the compositions described herein are synthesized using reversible addition-fragmentation chain transfer (RAFT) polymerization. RAFT polymerization is a controlled living polymerization strategy for developing polymers with well-controlled molecular weights and polydispersities, polymer chain ends with different end functionalities, and a variety of architectures. In certain embodiments, these characteristics are beneficial for the development of effective and easy to manufacture polymer-based therapeutics.

In one embodiment, the invention provides a method for treating osteoporosis, osteonecrosis, osteomyelitis, osteoarthritis, Paget's disease, bone allograft rejection, bone autograft rejection, wear-debris induced osteolysis, bone cancer, bone fractures, and the like. The method comprises administering an effective amount of the therapeutic-tethered macromer at a site in need of bone formation or bone treatment. The method provides controlled local delivery of the therapeutic agent at a site in need of bone formation or bone treatment.

In one embodiment, the method comprises administering a hydrogel comprising the therapeutic-tethered macromer to a site in need of bone formation or bone treatment in a subject. In certain embodiments, degradation of tethers within the therapeutic-tethered macromer releases the therapeutic agent from the hydrogel to a treatment site.

In one embodiment, the method comprises administering a hydrogel comprising a bone-homed particle comprising the therapeutic-tethered macromere to a site in need of bone formation or bone treatment in a subject. In certain embodiments, degradation of tethers within the therapeutic-tethered macromere releases the therapeutic agent from the hydrogel, and the bone-homed monomer prevents diffusion away from the local treatment site.

In one embodiment, the method comprises administering a hydrogel comprising a bone-homed particle comprising the therapeutic-tethered macromer to a subject. In certain embodiments, degradation of tethers within the therapeutic-tethered macromer releases the therapeutic agent from the hydrogel to a site in need of bone formation or bone treatment.

In another embodiment, the method comprises administering an effective amount of a bone-homed particle comprising the therapeutic-tethered macromer to a subject. In certain embodiments, the bone-homed particle is administered systemically to the subject, including for example by enteral or parenteral administration. In certain embodiments, degradation of tethers within the therapeutic-tethered macromer releases the therapeutic agent from the bone-homed particle to a treatment site.

Therapeutic-tethered Macromer

The composition of the invention comprises a therapeutic-tethered macromer that induces bone formation. In one embodiment, therapeutic-tethered macromer comprises a therapeutic agent tethered to a polymer. The therapeutic agent may be a nucleic acid, protein, peptide, small molecule, aptamer, antagonist, peptidomimetic, or combination thereof that promotes bone formation. For example, in certain embodiments, the therapeutic agent may enhance the expression or activity of a biomolecule known to play a role in bone formation. In one embodiment, the therapeutic agent enhances Wnt/β-catenin activity. In another embodiment, the therapeutic agent inhibits the expression or activity of a biomolecule known to be an inhibitor of bone formation. In certain embodiments, the therapeutic agent is an inhibitor of GSK3β. As such, the therapeutic agent may be any a nucleic acid, protein, peptide, small molecule, aptamer, antagonist, peptidomimetic, or combination thereof that inhibits the expression and/or activity of GSK3β. In one embodiment, the therapeutic agent comprises 6-bromoindirubin-3'oxime (BIO), a small molecule inhibitor of GSK3β. In one embodiment, the therapeutic agent comprises GSK3β inhibitor XXVII.

The present invention is not limited to any particular therapeutic agent, but rather encompasses a macromer as described herein comprising one or more therapeutic agents known in the art, or discovered in the future, which aid in bone formation. For example, in certain embodiments, the macromer comprises one or more nutrients, vitamins, supplements, hormones, proteins, bisphosphonates, growth factors, selective estrogen receptor modulators (SERMs), and the like. Exemplary therapeutic agents include, but are not limited to, fluvastatin, zoledronic acid, alendronic acid, pamidronic acid, ibandronic acid, risedronic acid, etidronic acid, tiludronic acid, clodronic acid, teriparatide, strontium ranelate, and raloxifene.

In certain embodiments, the macromer of the invention comprises one or more imaging agents. For example, the macromer may comprise a contrast agent, tag, label, or the like, that allows for imaging and localization of the macromer.

In certain embodiments, the therapeutic-tethered macromer of the invention comprises one or more degradable tethers that link the therapeutic agent with a polymer. In a particular embodiment, the therapeutic-tethered macromer comprises BIO tethered to poly(ethylene glycol) (PEG) methacrylate through hydrolytically degradable bonds. In a particular embodiment, the therapeutic-tethered macromer comprises BIO tethered to poly(styrene-alt-maleic anhydride)-b-poly(styrene) (PSMA-b-PS) methacrylate through hydrolytically degradable bonds. In a particular embodiment, the therapeutic-tethered macromer comprises GSK3β inhibitor XXVII tethered to PEG methacrylate through hydrolytically degradable bonds. In a particular embodiment, the therapeutic-tethered macromer comprises GSK3β inhibitor XXVII tethered to PSMA-b-PS methacrylate through hydrolytically degradable bonds. In various embodiments, the therapeutic-tethered macromere comprises PEG methacrylate or PSMA-b-PS methacrylate tethered to other inhibitors, such as CC chemokine receptor (CCR) inhibitors.

Small Molecule

When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like. In one embodiment, the small molecule inhibitor of the invention is BIO, a small molecule inhibitor of GSK3β. In one embodiment, the small molecule inhibitor of the invention is GSK3β inhibitor XXVII.

Combinatorial libraries of molecularly diverse chemical compounds potentially useful in treating a variety of diseases and conditions are well known in the art, as are methods of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted, and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

As used herein, the term "analog," "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to increase bone formation.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization, new analogs are designed considering issues of drug delivery, metabolism, novelty, and safety.

In some instances, small molecule inhibitors described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

In one embodiment, the small molecule inhibitors described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Nucleic Acids

In other related aspects, the invention includes an isolated nucleic acid, including for example an isolated nucleic encoding an inhibitor. In some instances the inhibitor is a small interfering RNA (siRNA) or antisense molecule, that inhibits GSK3β. In one embodiment, the nucleic acid comprises a promoter/regulatory sequence such that the nucleic acid is preferably capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein. In another aspect of the invention, a target of the inhibitor (e.g. GSK3β), can be inhibited by way of inactivating and/or sequestering the target. As such, inhibiting the activity of the target can be accomplished by using a transdominant negative mutant.

In one embodiment, siRNA is used to decrease the level of a protein inhibitory of bone formation (e.g., GSK3β). RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide siRNAs by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of GSK3β using RNAi technology.

In another aspect, the invention includes a vector comprising an siRNA or antisense polynucleotide. Preferably, the siRNA or antisense polynucleotide is capable of inhibiting the expression of a target polypeptide. In certain embodiments, the target polypeptide is GSK3β. The incorporation of a desired polynucleotide into a vector and the choice of vectors is well-known in the art as described in, for example, Sambrook et al., supra, and Ausubel et al., supra, and elsewhere herein.

The siRNA or antisense polynucleotide can be cloned into a number of types of vectors as described elsewhere herein.

For expression of the siRNA or antisense polynucleotide, at least one module in each promoter functions to position the start site for RNA synthesis.

In order to assess the expression of the siRNA or antisense polynucleotide, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl- methyl-, thio- and other modified forms of adenine, cytidine, guanine, thymine, and uridine.

In one embodiment of the invention, an antisense nucleic acid sequence which is expressed by a plasmid vector is used to inhibit GSK3β. The antisense expressing vector is used to transfect a mammalian cell or the mammal itself, thereby causing reduced endogenous expression of GSK3β.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Compositions and methods for the synthesis and expression of antisense nucleic acids are as described elsewhere herein.

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In one embodiment of the invention, a ribozyme is used to inhibit GSK3β expression. Ribozymes useful for inhibiting the expression of a target molecule may be designed by incorporating target sequences into the basic ribozyme structure that are complementary, for example, to the mRNA sequence of GSK3β. Ribozymes targeting GSK3β may be synthesized using commercially available reagents (Applied Biosystems, Inc., Foster City, Calif.) or they may be genetically expressed from DNA encoding them.

Peptides

In other related aspects, the invention includes an isolated peptide. In one embodiment, the invention comprises an isolated peptide inhibitor that inhibits the activity of GSK3β. For example, in one embodiment, the peptide inhibitor of the invention inhibits the activity of GSK3β directly by binding to GSK3β, thereby preventing the normal functional activity of GSK3β. In another embodiment, the peptide inhibitor of the invention inhibits the activity of GSK3β by competing with endogenous GSK3β. In yet another embodiment, the peptide inhibitor of the invention inhibits the activity of GSK3β by acting as a transdominant negative mutant.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the amino-acylated tRNA. These reactions are referred to as post-aminoacylation modifications. For example, the epsilon-amino group of the lysine linked to its cognate tRNA ($tRNA_{LYS}$), could be modified with an amine-specific photoaffinity label.

A peptide inhibitor of the invention may be conjugated with other molecules, such as proteins, to prepare fusion proteins. This may be accomplished, for example, by the synthesis of N-terminal or C-terminal fusion proteins, provided that the resulting fusion protein retains the functionality of the peptide inhibitor.

Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide that is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

In other embodiments, the subject peptide inhibitor therapeutic agents are peptidomimetics of the peptide inhibitors. Peptidomimetics are compounds based on, or derived from, peptides and proteins. The peptidomimetics of the present invention typically can be obtained by structural modification of a known peptide inhibitor sequence using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptide inhibitors.

Moreover, as is apparent from the present disclosure, mimetopes of the subject peptide inhibitor can be provided. Such peptidomimetics can have such attributes as being non-hydrolyzable (e.g., increased stability against proteases or other physiological conditions that degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), β-aminoalcohols (Gordon et al. (1985) Biochem Biophys Res Commun 126:419; and Dann et al. (1986) Biochem Biophys Res Commun 134:71), diaminoketones (Natarajan et al. (1984) Biochem Biophys Res Commun 124:141), and methyleneamino-modified (Roark et al. in Peptides: Chemistry and Biology, G. R. Marshall ed., ESCOM Publisher: Leiden, Netherlands, 1988, p 134). Also, see generally, Session III: Analytic and synthetic methods, in Peptides: Chemistry and Biology, G. R. Marshall ed., ESCOM Publisher: Leiden, Netherlands, 1988)

In addition to a variety of side chain replacements that can be carried out to generate the peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of binding to the peptide inhibitor. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

A peptide inhibitor, or chimeric protein, of the invention may be synthesized by conventional techniques. For example, the peptide inhibitors or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis).

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Antibodies

The invention also contemplates an inhibitor of GSK3β comprising an antibody, or antibody fragment, that specifically binds to GSK3β. The antibodies may be intact monoclonal or polyclonal antibodies, and immunologically active fragments (e.g. a Fab or (Fab)$_2$ fragment), an antibody heavy chain, an antibody light chain, humanized antibodies, a genetically engineered single chain Fv molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments, and chimeras may be prepared using methods known to those skilled in the art.

Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin, thyroglobulin, and keyhole limpet hemocyanin. The coupled polypeptide may then be used to immunize the animal (e.g., a mouse, a rat, or a rabbit).

Prior to its use as an inhibitor, a peptide is purified to remove contaminants. In this regard, it will be appreciated that the peptide will be purified so as to meet the standards set out by the appropriate regulatory agencies. Any one of a number of conventional purification procedures may be used to attain the required level of purity, including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate polypeptides based on their charge. Affinity chromatography is also useful in purification procedures.

Antibodies and peptides may be modified using ordinary molecular biological techniques to improve their resistance to proteolytic degradation, or to optimize solubility properties, or to render them more suitable as a therapeutic agent. Analogs of such polypeptides include those containing residues other than naturally occurring L-amino acids, e.g., D-amino acids or non-naturally occurring synthetic amino acids. The polypeptides useful in the invention may further be conjugated to non-amino acid moieties that are useful in their application. In particular, moieties that improve the stability, biological half-life, water solubility, and immunologic characteristics of the peptide are useful. A non-limiting example of such a moiety is polyethylene glycol (PEG).

Therapeutic Agent Tethering

As described herein, in certain embodiments, the therapeutic agent of the invention is tethered to a polymer to form a therapeutic-tethered macromer. Thus, in certain embodiments, the therapeutic-tethered macromer comprises a tether or linker. The tether or linker is a chemical bond or a multifunctional (e.g., bifunctional) residue that is used to link the therapeutic agent, as described elsewhere herein, to the polymer. The therapeutic-tethered macromer may comprise any suitable polymer, including biopolymers and synthetic polymers, tethered to the therapeutic agent. Exemplary polymers include, but are not limited to PEG, PEG methacrylate, poly(2-hydroxypropyl methacrylate), PSMA-b-PS, and poly(hydroxyethyl methacrylate).

Linkers comprise any of a variety of compounds that can form an amide, ester, ether, thioether, carbamate, urea, amine or other linkage, e.g., linkages that are commonly used for immobilization of biomolecules in affinity chromatography. In some embodiments, the linker comprises a cleavable bond, e.g. a bond that is unstable and/or is cleaved upon changes in certain intracellular parameters (e.g., pH or redox potential). In some embodiments, the linker is non-cleavable. In certain embodiments, the linker is attached to the therapeutic agent by one or more covalent bonds. In some embodiments, the linker is attached to the polymer through one or more covalent bonds. In some embodiments, the linking moiety comprises an affinity binder pair. In certain embodiments, the therapeutic agent and/or one of the ends of the polymer is modified with chemical moieties that afford the modified therapeutic agent and modified polymer to have an affinity for one another, such as arylboronic acid-salicylhydroxamic acid, leucine zipper or other peptide motifs, or other types of chemical affinity linkages.

In some embodiments, a therapeutic agent is chemically tethered to the polymer of the therapeutic-tethered macromer by any suitable chemical conjugation technique. In some embodiments, the therapeutic-tethered macromer is formed by conjugation of the therapeutic agent with the conjugatable moiety at the alpha end of the polymer. In some embodiments, the therapeutic-tethered macromer is formed by conjugation of the therapeutic agent with the conjugatable moiety at the omega end of the polymer. The linker (e.g., a covalent bond) between a polymer and therapeutic agent of a therapeutic-tethered macromer described herein is, optionally, non-cleavable, or cleavable. In some embodiments, a therapeutic agent is attached through a cleavable linker or cleavable tether. In some instances, the linker between the therapeutic agent and the polymer of the therapeutic-tethered macromer provided herein comprises a cleavable bond. In other instances, the linker between the therapeutic agent and the polymer of the therapeutic-tethered macromer provided herein is non-cleavable. In certain embodiments, the cleavable bonds utilized in the therapeutic-tethered macromer described herein include, by way of non-limiting example, disulfide bonds (e.g., disulfide bonds that dissociate in certain reducing environments). In some embodiments, the linker comprises ester bonds (e.g., lactide). In some embodiments, the linker is cleavable and/or comprises a bond that is cleavable in acidic pH (e.g., endosomal conditions or within resorption pits). In some embodiments, the linker is cleavable and/or comprises a bond that is cleavable by a specific enzyme (e.g., a phosphatase, or a protease). In some embodiments, the linker is cleavable and/or comprises a bond that is cleavable upon a change in an intracellular or extracellular parameter (e.g., pH, redox potential). In some embodiments, covalent association between a polymer (e.g., the alpha or omega end conjugatable group of the polymer) and a therapeutic agent is achieved through any suitable chemical conjugation method, including but not limited to amine-carboxyl linkers, amine-aldehyde linkers, amine-ketone linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In some embodiments, a bifunctional cross-linking reagent is employed to achieve the covalent conjugation between suitable conjugatable groups of the therapeutic agent and the polymer. In some embodiments, conjugation is also performed with pH-sensitive bonds and linkers, including, but not limited to, hydrazone and acetal linkages. Any other suitable conjugation method is optionally utilized as well, for example a large variety of conjugation chemistries are available (see, for example, Bioconjugation, Aslam and Dent, Eds, Macmillan, 1998 and chapters therein).

In some embodiments, the linker between the therapeutic agent and the polymer is degradable. For example, in certain embodiments, the linker or tether between the therapeutic agent and polymer comprise hydrolytically degradable ester bonds, for example ester bonds comprised within a lactide tether. In certain embodiments, the length of the lactide tether controls the rate of release of the therapeutic agent. In some embodiments, the rate of release is increased as the length of the tether is increased. In other embodiments, the rate of release is decreased as the length of the tether in the therapeutic-tethered macromer is increased.

In certain embodiments, a therapeutic-tethered macromer provided herein is prepared according to a process comprising the following two steps: (1) activating a modifiable end group of the therapeutic agent using any suitable activation reagents, such as but not limited tol-ethyl-3,3-dimethylaminopropyl carbodiimide (EDAC), imidazole, N-hydrosuccinimide (NHS) and dicyclohexylcarbodiimide (DCC), HOBt (1-hydroxybenzotriazole), p-nitrophenylchloroformate, carbonyldiimidazole (CDI), and N,N'-disuccinimidyl carbonate (DSC); and (2) covalently linking the polymer (e.g., the alpha or omega end of the polymer) to the end of the therapeutic agent. In some embodiments, the modifiable group of the therapeutic agent is substituted by other functional groups prior to conjugation with the polymer. For example, hydroxyl group (—OH) is optionally substituted with a linker carrying sulfhydryl group (—SH), carboxyl group (—COOH), or amine group (—NH$_2$).

In yet another embodiment, a therapeutic agent comprising a functional group (for example, a 5-aminoalkylpyrimidine), is conjugated the polymer provided herein using a an activating agent or a reactive bifunctional linker according to any suitable procedure. A variety of such activating agents and bifunctional linkers is available commercially from such suppliers as Sigma, Pierce, Invitrogen, and others.

In certain embodiments, the therapeutic-tethered macromer of the invention is synthesized as performed previously, for example as described in Benoit et al. 2006, Biomaterials, 27(36): 6102-6110 and Nuttelman et al., 2006, J Biomed Res A, 76(1): 183-195, each of which are incorporated by reference herein, in their entireties.

Hydrogels

In one embodiment, the present invention provides a hydrogel comprising the therapeutic-tethered macromer described herein. Hydrogels can generally absorb a great deal of fluid and, at equilibrium, typically are composed of 60-90% fluid and only 10-30% polymer. In a preferred embodiment, the water content of hydrogel is about 70-80%. Hydrogels are particularly useful due to the inherent biocompatibility of the polymeric network (Hill-West, et al., 1994, Proc. Natl. Acad. Sci. USA 91:5967-5971). Hydrogel biocompatibility can be attributed to hydrophilicity and ability to imbibe large amounts of biological fluids (Brannon-Peppas. Preparation and Characterization of Cross-linked Hydrophilic Networks in Absorbent Polymer Technology, Brannon-Peppas and Harland, Eds. 1990, Elsevier: Amsterdam, pp 45-66; Peppas and Mikos. Preparation Methods and Structure of Hydrogels in Hydrogels in Medicine and Pharmacy, Peppas, Ed. 1986, CRC Press: Boca Raton, Fla., pp 1-27). In certain embodiments, the hydrogels can be prepared by crosslinking hydrophilic biopolymers or synthetic polymers. In certain embodiments, construction of hydrogels comprises the polymerization and/or copolymerization of monomers, macromers, polymers, and the like. For example, in one embodiment hydrogel formation comprises copolymerization of two or more types of biopolymers and/or synthetic polymers.

Examples of the hydrogels formed from physical or chemical crosslinking of hydrophilic biopolymers, include but are not limited to, hyaluronans, chitosans, alginates, collagen, dextran, pectin, carrageenan, polylysine, gelatin or agarose. (see: W. E. Hennink and C. F. van Nostrum, 2002, Adv. Drug Del. Rev. 54, 13-36 and A. S. Hoffman, 2002, Adv. Drug Del. Rev. 43, 3-12). These materials consist of high-molecular weight backbone chains made of linear or branched polysaccharides or polypeptides. Examples of hydrogels based on chemical or physical crosslinking synthetic polymers include but are not limited to (meth)acrylate-oligolactide-PEO-oligolactide-(meth)acrylate, poly (ethylene glycol) (PEO; PEG), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), PEG monoethylether methacrylate, etc. (see A. S Hoffman, 2002 Adv. Drug Del. Rev, 43, 3-12). In some embodiments, the hydrogel comprises poly(ethylene glycol) methacrylate. In some embodiments, the hydrogel comprises poly(styrene-alt-maleic anhydride)-b-poly(styrene) methacrylate.

In one embodiment, the hydrogel comprises at least one biopolymer. In other embodiments, the hydrogel scaffold further comprises at least two biopolymers. In yet other embodiments, the hydrogel scaffold further comprises at least one biopolymer and at least one synthetic polymer.

Hydrogels closely resemble the natural living extracellular matrix (Ratner and Hoffman. Synthetic Hydrogels for Biomedical Applications in Hydrogels for Medical and Related Applications, Andrade, Ed. 1976, American Chemical Society: Washington, D.C., pp 1-36). Hydrogels can also be made degradable in vivo by incorporating PLA, PLGA or PGA polymers. Moreover, hydrogels can be modified with fibronectin, laminin, vitronectin, or, for example, RGD for surface modification, which can promote cell adhesion and proliferation (Heungsoo Shin, 2003, Biomaterials 24:4353-4364; Hwang et al., 2006 Tissue Eng. 12:2695-706). Indeed, altering molecular weights, block structures, degradable linkages, and cross-linking modes can influence strength, elasticity, and degradation properties of the instant hydrogels (Nguyen and West, 2002, Biomaterials 23(22):4307-14; Ifkovits and Burkick, 2007, Tissue Eng. 13(10):2369-85).

Hydrogels can also be modified with functional groups for covalently attaching a variety of proteins (e.g., collagen) or compounds such as therapeutic agents. Therapeutic agents that can be linked to the matrix include, but are not limited to, analgesics, anesthetics, antifungals, antibiotics, anti-inflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, colored or fluorescent imaging agents, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, radioisotopes, sedatives, sulfonamides, stimulants, sympathomimetics, tranquilizers, urinary anti-infectives, vasoconstrictors, vasodilators, vitamins, xanthine derivatives, and the like. The therapeutic agent can also be other small organic molecules, naturally isolated entities or their analogs, organometallic agents, chelated metals or metal salts, peptide-based drugs, or peptidic or non-peptidic receptor targeting or binding agents. It is contemplated that linkage of the therapeutic agent to the matrix can be via a protease sensitive linker or other biodegradable linkage. Molecules that can be incorporated into the hydrogel matrix include, but are not limited to, vitamins and other nutritional supplements, glycoproteins (e.g., collagen), fibronectin, peptides and proteins, carbohydrates (both simple and/or complex), proteoglycans, antigens, oligonucleotides (sense and/or antisense DNA and/or RNA), antibodies (for example, to infectious agents, tumors, drugs or hormones), and gene therapy reagents.

In certain embodiments, the hydrogel comprises the therapeutic-tethered macromer described elsewhere herein. The therapeutic-tethered macromer may be covalently or non-covalently attached to the hydrogel matrix. In one embodiment, the linkage between the hydrogel matrix and the therapeutic-tethered macromer is degradable. In another embodiment, the linkage between the hydrogel matrix and therapeutic-tethered macromer is non-degradable. In certain embodiments, the therapeutic-tethered macromer of the invention is copolymerized with one or more biopolymers or synthetic polymers to produce hydrogels with incorporated therapeutic-tethered macromer. For example, in one embodiment, the therapeutic-tethered macromer of the invention is copolymerized with PEG to form PEG-based hydrogels comprising the therapeutic-tethered macromer. In one embodiment, the hydrogel comprises a therapeutic-tethered macromer comprising BIO tethered to PEG methacrylate. In one embodiment, the hydrogel comprises a therapeutic-tethered macromer comprising BIO tethered to PSMA-b-PS methacrylate. In one embodiment, the hydrogel comprises a therapeutic-tethered macromere comprising GSK3β inhibitor XXVII tethered to PEG methacrylate. In one embodiment, the hydrogel comprises a therapeutic-tethered macromere comprising GSK3β inhibitor XXVII tethered to PSMA-b-PS methacrylate. As described elsewhere herein, in certain embodiments, the therapeutic-tethered macromer comprises a degradable tether. Thus, in certain embodiments, the hydrogel comprises a therapeutic agent (e.g., BIO, GSK3β inhibitor XXVII) that can be controllably released from the hydrogel.

In certain embodiments, one or more multifunctional cross-linking agents may be utilized as reactive moieties that covalently link biopolymers or synthetic polymers. Such bifunctional cross-linking agents may include glutaraldehyde, epoxides (e.g., bis-oxiranes), oxidized dextran, p-azidobenzoyl hydrazide, N-[α.-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS), and other bifunctional cross-linking reagents known to those skilled in the art. It should be appreciated by those skilled in the art that the mechanical properties of the hydrogel are greatly influenced by the cross-linking time and the amount of cross-linking agents.

In another embodiment utilizing a cross-linking agent, polyacrylated materials, such as ethoxylated (20) trimethylpropane triacrylate, may be used as a non-specific photoactivated cross-linking agent. Components of an exemplary reaction mixture would include a thermoreversible hydrogel held at 39° C., polyacrylate monomers, such as ethoxylated (20) trimethylpropane triacrylate, a photo-initiator, such as eosin Y, catalytic agents, such as 1-vinyl-2-pyrrolidinone, and triethanolamine. Continuous exposure of this reactive mixture to long-wavelength light (>498 nm) would produce a cross-linked hydrogel network.

In one embodiment, the hydrogel comprises a UV sensitive curing agent that initiates hydrogel polymerization. For example, in one embodiment, a hydrogel comprises the photoinitiator 4-(2-hydroxyethoxy)phenyl-(2-hydroxy-2-propyl)ketone. In one embodiment, polymerization is induced by 4-(2-hydroxyethoxy)phenyl-(2-hydroxy-2-propyl)ketone upon application of UV light. Other examples of UV sensitive curing agents include 2-hydroxy-2-methyl-1-phenylpropan-2-one, 4-(2-hydroxyethoxy)phenyl (2-hydroxy-2-phenyl-2-hydroxy-2-propyl)ketone, 2,2-dimethoxy-2-phenyl-acetophenone 1-[4-(2-Hydroxyethoxy)-phenyl]-2-hydroxy-2-methyl-1-propane-1-one, 1-hydroxycyclohexylphenyl ketone, trimethyl benzoyl diphenyl phosphine oxide, and mixtures thereof.

The stabilized cross-linked hydrogel matrix of the present invention may be further stabilized and enhanced through the addition of one or more enhancing agents. The terms "enhancing agent" or "stabilizing agent" are intended to refer to any compound added to the hydrogel matrix, in addition to the high molecular weight components, that enhances the hydrogel matrix by providing further stability or functional advantages. Suitable enhancing agents, which are admixed with the high molecular weight components and dispersed within the hydrogel matrix, include many of the additives described earlier in connection with the thermoreversible matrix discussed above. The enhancing agent can include any compound, especially polar compounds, that, when incorporated into the cross-linked hydrogel matrix, enhance the hydrogel matrix by providing further stability or functional advantages.

Preferred enhancing agents for use with the stabilized cross-linked hydrogel matrix include polar amino acids, amino acid analogues, amino acid derivatives, intact collagen, and divalent cation chelators, such as ethylenediaminetetraacetic acid (EDTA) or salts thereof. Polar amino acids are intended to include tyrosine, cysteine, serine, threonine, asparagine, glutamine, aspartic acid, glutamic acid, arginine, lysine, and histidine. The preferred polar amino acids are L-cysteine, L-glutamic acid, L-lysine, and L-arginine. Suitable concentrations of each particular preferred enhancing agent are the same as noted above in connection with the thermoreversible hydrogel matrix. Polar amino acids, EDTA, and mixtures thereof, are preferred enhancing agents. The enhancing agents can be added to the matrix composition before or during the crosslinking of the high molecular weight components.

The enhancing agents are particularly important in the stabilized cross-linked bioactive hydrogel matrix because of the inherent properties they promote within the matrix. The hydrogel matrix exhibits an intrinsic bioactivity that will become more evident through the additional embodiments described hereinafter. It is believed the intrinsic bioactivity is a function of the unique stereochemistry of the cross-linked macromolecules in the presence of the enhancing and strengthening polar amino acids, as well as other enhancing agents.

In one embodiment, the method comprises manufacture of a hydrogel comprising the therapeutic-tethered macromer described herein. Manufacture of a hydrogel may comprise any known methods or techniques known in the art. For example, in certain embodiments, the method comprises forming a solution comprising the therapeutic-tethered macromer of the invention and optionally, one or more suitable biopolymers or synthetic polymers. In certain embodiments, the manufacture of the hydrogel comprises administering of a crosslinker to a hydrogel solution. In some embodiments, the hydrogel is fabricated by emulsification, photolithography, microfluidic synthesis, micromolding, or micro-electrospinning, or a combination thereof. The hydrogel can have a structure, e.g., including one or more of a film, pad, cylinder, tube, micro thin film, a micro pad, a micro thin fiber, a nanosphere or a microsphere. The hydrogel of the invention may be formed to be of any size or geometry as needed by its application. For example, the hydrogel may be formed with a pre-determined size and geometry, or alternatively may be cut into a desired size and geometry after formation. The hydrogel may be formed to comprise any suitable amount of the therapeutic agent. For example, the concentration of the therapeutic agent within the hydrogel may be altered by increasing or decreasing the amount of therapeutic agent added to a hydrogel solution. The desired amount of the therapeutic agent comprised in the hydrogel depends on the activity of the agent, the disease state of the patient, and the drug delivery characteristics of the agent. In certain embodiments, the hydrogel is formulated to provide sustained release of the embedded therapeutic agent. For example, in certain embodiments, the hydrogel provides sustained release of the therapeutic agent for at least 1 hour, 1 day, 3 days, 1 week, 2 weeks, 1 month, 3 months, 6 months, 1 year, 5 years, 10 years, or more. In one embodiment, the release rate of the therapeutic agent is dependent on the type of degradable tether and/or length of degradable tether used in formulation of the therapeutic-tethered macromer, as described elsewhere herein.

In certain embodiments, the hydrogel is modified to improve its functionality. For example, the hydrogel may be coated with any number of compounds in order enhance biocompatibility, reduce immunogenicity, enhance stability, enhance degradation, and/or enhance drug delivery.

Bone-Homed Particle

In one embodiment, the composition of the invention comprises a bone-homed particle comprising the therapeutic-tethered macromer described herein. For example, in certain embodiments, the bone-homed particle comprises a liposome, micelle, nanoparticle, microparticle, nanosphere, microsphere, polymer, brush polymer, copolymer, and the like, or any combination thereof.

In one embodiment, the bone-homed particle comprises a targeting domain that targets the particle to a site in need of bone formation or bone treatment. The targeting domain may comprise a nucleic acid, peptide, antibody, antibody fragment, small molecule, inorganic molecule, organic molecule, and the like.

In certain embodiments, the targeting domain of the particle specifically binds to a target associated with a site in need of bone formation or bone treatment. For example, the targeting domain may be chosen to recognize a ligand that acts as a cell surface marker on target cells associated with a particular disease state (i.e. osteoporosis, osteonecrosis, osteomyelitis, osteoarthritis, Paget's disease, bone allograft rejection, bone autograft rejection, wear-debris induced osteolysis, bone cancer, bone fracture). Such a target can be a protein, protein fragment, antigen, or other biomolecule that is associated with a site in need of bone formation or bone treatment. In certain embodiments, the target (e.g. antigen) associated with a site in need of bone formation or bone treatment is tartrate-resistant acid phosphatase (TRAP). TRAP is a molecule left behind by osteoclasts in resorption sites, and thus is associated with a region of bone that is need of bone formation.

In one embodiment, the targeting domain comprises an antibody, or antibody fragment, that specifically binds to an antigen associated with a site in need of bone formation or bone treatment (e.g. TRAP). In one embodiment, the targeting domain may consist of an immunoglobulin (Ig) heavy chain which may in turn be covalently associated with an Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed, or all or part of the hinge region may be removed.

In one embodiment, the targeting domain comprises a peptide, or peptide fragment, that specifically binds to target associated with a site in need of bone formation or bone treatment (e.g., TRAP). Peptide and peptide fragments can be manufactured using biological or synthetic techniques, as described elsewhere herein. Further, the targeting domain encompasses chimeric peptides, peptidomimetics, and peptide variants, as discussed elsewhere herein. In a particular embodiment, the peptide comprises the amino acid sequence TPLSYLKGLVTVG (SEQ ID NO: 1), a peptide known to home to TRAP with subnanomolar affinity. In a particular embodiment, the peptide comprises the amino acid sequence TPLSYLKGLVTV (SEQ ID NO: 3). In one embodiment, the peptide comprises a methacrylamide group. Functionalization with a polymerizable methacrylamide groups allow for the incorporation of the peptide into polymers.

In one embodiment, the targeting domain of the particle comprises one or more monomers having bone-homing capability. For example, in one embodiment a monomer of the particle comprise a phosphate that targets the particle to bone. For example, the particle may comprise bisphosphonate, phosphonate mimetics that home to bone. In another embodiment, the particle comprises 6-methacryloyloxy-hexyl dihydrogen phosphate. As described elsewhere herein, 6-methacryloyloxyhexyl dihydrogen phosphate is a phosphate containing monomer that displays homing to bone. In one embodiment, a monomer of the peptide comprises an acidic amino acid mimetic, which targets the particle to resorptive pits (i.e., a site in need of bone formation or bone treatment). For example, in certain embodiments, the particle comprises methacrylated acid amino acid monomers. In certain embodiments, the particle comprises methacrylated glutamic acid or methacrylated aspartic acid monomers. These acidic amino acid mimetic monomers can be synthesized, for example, by conjugating the amine group of the amino acid to methacryloyl chloride or reacting the amine group with methacrylic anhydride. In certain embodiments, the particle comprises multivalent targeting, wherein the particle comprises multiple targeting mechanisms described herein. For example, polymerization of the phosphate-containing monomers or the acid amino acid mimetic monomers provides for multivalent polymeric particles that, in some instances, are more likely to correctly home to bone or resorptive pits. In some embodiments, the particle comprises more than one of a targeting peptide, phosphate-containing monomer, and amino acid mimetic-containing monomer described herein.

In one embodiment, the bone-homed particle comprises a micelle or nanoparticle having a hydrophobic core region and a hydrophilic shell region. For example, in one embodiment, the micelle or nanoparticle comprises block copolymers, comprising at least one hydrophobic block and at least one hydrophilic block. In certain embodiments, the therapeutic-tethered macromer described herein is covalently or noncovalently attached to the micelle or nanoparticle. For example, in certain embodiments, the hydrophobic block and/or hydrophilic block comprise the therapeutic-tethered macromer. In one embodiment, the therapeutic-tethered macromer is polymerized within the hydrophobic core. In one embodiment, the therapeutic-tethered macromer is polymerized within the hydrophilic shell. Attaching the therapeutic-tethered macromer to the micelle or nanoparticle may be done using any method known in the art.

In certain embodiments, the "block copolymers" described herein comprise a core section and a shell section. As discussed herein, the core section optionally is or comprises a core block and the shell section optionally comprises or is a shell block. In some embodiments, at least one of such blocks is a gradient polymer block. In further embodiments, the block copolymer utilized herein is optionally substituted with a gradient polymer (i.e., the polymer utilized in the micelle or nanoparticle is a gradient polymer having a core section and a shell section).

In certain embodiments, the micelle or nanoparticle has a size of approximately 10 nm to about 200 nm, about 10 nm to about 100 nm, or about 30-80 nm. Particle size can be determined in any manner, including, but not limited to, by gel permeation chromatography (GPC), dynamic light scattering (DLS), electron microscopy techniques (e.g., TEM), and other methods.

In certain embodiments, the shell and/or shell block is hydrophilic and/or charged (e.g., non-charged, cationic, polycationic, anionic, polyanionic, or zwitterionic). In certain embodiments, the shell and/or shell block is hydrophilic and neutral (non-charged). In specific embodiments, the shell and/or shell block comprises a net positive charge. In specific embodiments, the shell and/or shell block comprises a net negative charge. In specific embodiments, the shell and/or shell block comprises a net neutral charge. In some embodiments, the core and/or core block is hydrophobic and/or comprises hydrophobic groups, moieties, monomeric units, species, or the like. In specific embodiments, the hydrophobic core and/or core block comprise a plurality of hydrophobic groups, moieties, monomeric units, species, or the like and a plurality of chargeable species or monomeric units. In more specific embodiments, the plurality of chargeable monomeric units or species comprises a plurality of anionic chargeable monomeric units or species. In more specific embodiments, the plurality of chargeable monomeric units or species comprises a plurality of cationic chargeable monomeric units or species. In still more specific embodiments, the plurality of chargeable monomeric units or species comprises a plurality of cationic and a plurality of anionic chargeable monomeric units or species. In some embodiments, the block copolymers each have (1) a hydrophilic, charged block (e.g., anionic or polyanionic; or cationic or polycationic; or zwitterionic; or non-charged) forming the shell of the micelle or nanoparticle, (2) a hydrophobic block, and (3) a plurality of anionic chargeable species. In some embodiments, the plurality of anionic chargeable species is present in the hydrophobic block. In certain embodiments, the hydrophobic core and/or core block optionally comprise spacer monomeric units which may or may not comprise hydrophobic groups, chargeable groups, or a combination thereof. In some embodiments, a polymer block forming or present in the core of the micelle or nanoparticle (e.g., one or more core block of the copolymer) is chargeable (e.g., contains cationic and/or anionic species at a physiological pH). In some instances, the micelles or nanoparticles provided herein are formed from a plurality of block copolymers that self-associate. In certain instances, the self-association occurs through the interactions of the hydrophobic blocks of the block copolymers, and the resulting micelles or nanoparticles are stabilized through hydrophobic interactions of the hydrophobic blocks present in the core of the micelle or nanoparticle.

In some embodiments, provided herein is a micelle or nanoparticle comprising a plurality of block copolymers comprising a core section (e.g., core block) and a shell section (e.g., shell block) wherein the ratio of the number average molecular weight of the core section (e.g., core block) to the number average molecular weight of the shell section (e.g., shell block) is present in any suitable ratio. In specific embodiments, block copolymers wherein the ratio of the number average molecular weight of the core section (e.g., core block) to the number average molecular weight of the shell section (e.g., shell block) is present in a ratio of about 1:10 to about 5:1, about 1:1 to about 5:1, about 5:4 to about 5:1, about 1:2 to about 2:1, about 2:1, about 1.5:1, about 1.1:1, about 1.2:1, about 1.3:1, about 1.4:1, about 1.6:1, about 1.7:1, about 1.8:1, about 1.9:1, or about 2.1:1. In some embodiments, block copolymers wherein the ratio of the number average molecular weight of the core section (e.g., core block) to the number average molecular weight of the shell section (e.g., shell block) is present in a ratio of about 2 (or more) to 1; about 1.5 (or more) to 1; about 1.1 (or more) to 1; about 1.2 (or more) to 1; about 1.3 (or more) to 1; about 1.4 (or more) to 1; about 1.6 (or more) to 1; about 1.7 (or more) to 1; about 1.8 (or more) to 1; about 1.9 (or more) to 1; or about 2.1 (or more) to 1. In specific embodiments, the ratio of the number average molecular weight of the core block to the number average molecular weight of the shell block is about 2:1.

In some embodiments, the micelles or nanoparticles provided herein retain activity (e.g., the activity of the micelle or nanoparticle to deliver a therapeutic agent) in mammalian tissue (e.g. serum, plasma, saliva, soft tissue, etc) for at least 2 hours, at least 4 hours, at least 6 hours, at least 8 hours, at least 12 hours, or at least 24 hours.

In various embodiments, block copolymers utilized in the micelles or nanoparticles described herein have or are selected to have an influence on a certain aspect or functionality of the micelles or nanoparticles provided herein, including but not limited to: (1) the biophysical properties of the micelle or nanoparticle such as, by way of non-limiting example, solubility, aqueous solubility, stability, stability in an aqueous medium, hydrophilicity, lipophilicity, hydrophobicity, or the like; (2) the facilitation of the formulation of the micelle or nanoparticle into an administrable form, or other purposes; (3) the ability of the micelle or nanoparticle to target a specific or selected type of cell or biostructure (e.g., by carrying a targeting moiety); and/or (4) the ability to increase biocompatibility of the micelle or nanoparticle. In some embodiments, a micelle or nanoparticle provided herein is characterized by one or more of the following: (1) the micelle or nanoparticle is formed by spontaneous self-association of block copolymers to form organized assemblies (e.g., micelles or nanoparticles) upon dilution from a water-miscible solvent (such as but not limited to ethanol) to aqueous solvents (for example phosphate-buffered saline, pH 7.4); (2) the micelle or nanoparticle is stable to dilution (e.g., down to a polymer concentration of 100 µg/ml, 50 µg/ml, 10 µg/ml, 5 µg/ml or 1 µg/ml, which constitutes the critical stability concentration or the critical micelle concentration (CMC) or critical nanoparticle concentration (CNC)); (3) the micelle or nanoparticle is stable to high ionic strength of the surrounding media (e.g. 0.5M NaCl); and/or (4) the micelle or nanoparticle has an increasing instability as the concentration of organic solvent increases, such organic solvents including, but not limited to dimethylformamide (DMF), dimethylsulfoxide (DMSO), and dioxane. In some embodiments, a micelle or nanoparticle provided herein is characterized by having at least two of the aforementioned properties. In some embodiments, a micelle or nanoparticle provided herein is characterized by having at least three of the aforementioned properties. In some embodiments, a micelle or nanoparticle provided herein is characterized by having all of the aforementioned properties.

In certain embodiments, micelles or nanoparticles provided herein are further or alternatively characterized by other criteria: (1) the molecular weight of the individual blocks and their relative length ratios is decreased or increased in order to govern the size of the micelle or nanoparticle formed and its relative stability and (2) the size of the polymer cationic block that forms the shell is varied in order to provide effective complex formation with and/or charge neutralization of an anionic therapeutic agent.

Moreover, in certain embodiments, micelles or nanoparticles provided herein selectively uptake small hydrophobic molecules, such as hydrophobic small molecule compounds (e.g., hydrophobic small molecule drugs) into the hydrophobic core of the particle. In certain embodiments, the micelle or nanoparticle provided herein comprises a therapeutic agent conjugated by way of linkers and/or tethers to one or more components of the micelle or nanoparticle. In certain embodiments, the therapeutic agents can comprise an analgesic agent, an anti-cancer agent, an anti-viral agent, an anti-bacterial agent, or an anti-inflammatory agent. In one embodiment, the therapeutic agent is a CC chemokine receptor (CCR) inhibitor. In one embodiment, the therapeutic agent is BX471. In another embodiment, the therapeutic agent is maraviroc.

In certain embodiments, the bone-homed particle comprises a polymeric composition comprising the therapeutic-tethered macromer described herein. For example, in certain embodiments, the bone-homed particle comprises a polymer complex comprising the therapeutic agent. In one embodiment, the particle comprises a polymer complex comprising a GSK3β inhibitor.

In certain embodiments, the bone-homed particle of the invention comprises a polymer of 1, 2, 5, 10, or more different types of monomers. The polymer can be manufactured to have a variety of different polymer architectures that allow the particle to have improved stability. In one embodiment, the particle comprises a homopolymer comprising the therapeutic agent. In another embodiment, the particle comprises a copolymer comprising the therapeutic agent. Copolymers can have a variety of different architectures that, in certain embodiments, may be preferred to allow for 1) targeting of the particle, 2) controlled release of the therapeutic, and/or 3) stability of the particle. Exemplary architectures of copolymers, include, but are not limited to, diblock copolymers, random copolymers, statistical copolymers, gradient copolymers, graft copolymers, and dendrimer copolymers. Exemplary polymers that may be used in the copolymer include, but are not limited to, PEG, PLGA, PEG methacrylate, polystyrene, polymethacrylate, polyacrylamide, PSMA-b-PS methacrylate, and the like.

In a particular embodiment, the bone-homed particle of the invention comprises a graft polymer comprising a backbone and at least one side chain. A graft polymer refers to a polymer molecule that has additional moieties attached as pendent groups along a polymer backbone. In certain embodiments, a graft polymer is a graft copolymer, wherein the backbone and side chains are comprised of different polymers. Graft polymers can be formed by graft polymerization in which a side chain is grafted onto a polymer chain, in which the side chain consists of one or several other monomers. The properties of the graft copolymer obtained such as, for example, solubility, melting point, water absorption, wettability, mechanical properties, adsorption behavior, etc., deviate more or less sharply from those of the initial polymer as a function of the type and amount of the grafted monomers. The term "grafting ratio," as used herein, means the weight percent of the amount of the monomers grafted based on the weight of the polymer. In one embodiment, the bone-homed particle comprises a graft polymer, wherein the side chains of the graft polymer comprise the therapeutic-tethered macromer.

In one embodiment, the targeting peptide of the bone-homed particle, as described herein are attached, in various embodiments, to either end of a polymer (e.g., block copolymer), or to a side chain or a pendant group of a monomeric unit, or to the end of a backbone polymer, or incorporated into a polymer. In some instances, the targeting peptide is covalently coupled to the polymer of the therapeutic-tethered macromer at the opposite end from the therapeutic agent.

In certain embodiments, a monomer comprising a targeting domain residue (e.g., a polymerizable derivative of a targeting domain such as an (alkyl)acrylic acid derivative of a peptide) is co-polymerized to form a copolymer. In certain embodiments, one or more targeting domains are coupled to a polymer provided herein through a linker. In some embodiments, the linker coupling the targeting ligand to a polymer is a cleavable linker (e.g., comprises a cleavable bond).

In some embodiments, the targeting domain is a proteinaceous targeting domain (e.g., a peptide, and antibody, an antibody fragment). In some specific embodiments, a plurality of therapeutic-tethered macromers are coupled to a polymer that is covalently coupled to the targeting domain. For example, in one embodiment, the bone-homed particle comprises a graft polymer comprising a backbone covalently attached to the targeting peptide, and a plurality of side chains comprising the therapeutic-tethered macromer. In some instances, a single targeting domain is used to deliver one or more therapeutic agents to a site in need of bone formation or bone treatment. In some instances, the bone-homed particle comprises at least 2, at least 5, or at least 10 targeting domains.

Attachment of the targeting peptide to the polymer is achieved in any suitable manner, e.g., by any one of a number of conjugation chemistry approaches including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In specific embodiments, "click" chemistry is used to attach the targeting ligand to the polymers of the polymer bioconjugates provided herein (for example of "click" reactions, see Wu, P.; Fokin, V. V. Catalytic Azide-Alkyne Cycloaddition: Reactivity and Applications. Aldrichim. Acta 2007, 40, 7-17). A large variety of conjugation chemistries are optionally utilized (see, for example, Bioconjugation, Aslam and Dent, Eds, Macmillan, 1998 and chapters therein). In some embodiments, targeting peptide are attached to a monomer and the resulting compound is then used in the polymerization synthesis of a polymer (e.g., copolymer).

In certain embodiments, the bone homed particle described herein is a brush polymer comprising the therapeutic-tethered macromer described herein. In some embodiments, the polymer comprises at least one bone targeting monomer (e.g., phosphate-containing monomer and/or acidic amino acid mimetic monomer). In certain embodiments, the brush polymer is a copolymer comprising the bone targeting monomers described herein and the therapeutic-tethered macromer of the invention. The architecture of the polymer can be varied to provide efficient targeting and release of the therapeutic agent. For example, in one embodiment, the brush polymer is a block copolymer. In another embodiment, the brush polymer is a statistical copolymer. Further, the polymer may be adjusted to vary the amount of either the bone targeting monomer and/or the amount of therapeutic-tethered macromer. In some embodiments, the polymer comprises about 0.1-10 wt % of bone targeting monomer. Further, the molecular weight of the polymer may be controlled to provide effective delivery and clearance of the polymer. For example, in one embodiment, the molecular weight of bone-homed particle of the invention is about 1-100 kDa. In another embodiment, the bone-homed particle of the invention is about 10-50 kDa.

The bone-homed particle of the invention may be formed by any suitable method known in the art or hereafter developed. In certain embodiments, polymers comprised in the bone-homed particle of the invention are synthesized using reversible addition-fragmentation chain transfer (RAFT). This technique uses a chain transfer agent (CTA) capable of maintaining the radical state of the propagating species or reinitiating polymerization and yields polymers with a low polydispersity index (PDI), indicative of uniform polymers. RAFT is a chain polymerization that introduces a CTA that modulates the rate of reaction thus forming polymers with well-controlled molecular weight and polydispersities, polymer chain ends with different functionalities, and a multitude of possible architectures. These characteristics are inherently important for reproducible therapeutic manufacturing, while the large variety in possible architectures enables design-on-demand methods to address the requirements of the delivery system. For example, dendrimers or brush architectures, as well as the end-functional nature of these polymers, impart the ability to mix-and-match drugs, targeting, or other functional moieties. This provides easy incorporation of both multivalent targeting and drug delivery chemistries into polymer architectures for tissue-specific delivery. In addition, RAFT polymers improve stability of therapeutic molecules, reduce immunogenicity, enhance solubility, and increase blood circulation times to achieve high doses of therapeutic at the right time, at the right place, and at the right concentrations. However, the polymers of the invention are not limited to polymers synthesized by RAFT. Other suitable methods include, but are not limited to emulsion polymerizations, atom-transfer radical polymerization (ATRP), traditional chain polymerization, and step polymerization. Exemplary methods of polymerization, and copolymerization are well known in the art such as those discussed in De Souza Gomes (2012, Polymerization, InTech).

In specific embodiments, the compositions provided herein, including the therapeutic-tethered macromer, hydrogel composition, and bone-homed particle, are biocompatible, as defined elsewhere herein. With regard to salts, it is presently preferred that both the cationic and the anionic species be biocompatible or "physiologically acceptable," which is interchangeable with biocompatible herein. In some instances, the polymer bioconjugates and polymers used herein (e.g., copolymers) exhibit low toxicity compared to cationic lipids.

Therapeutic Methods

The present invention provides a method for promoting or inducing bone formation. The method may be used, for example, as a therapy in treating diseases and disorders characterized by bone loss. In one embodiment, the method is used to treat a subject having osteoporosis. In another embodiment, the method is used to treat a subject at risk for having osteoporosis. In another embodiment, the method is used to treat a subject with bone cancer. In yet another embodiment, the method is used to treat a subject with a fractured bone. The method of the invention provides local delivery of a therapeutic agent to a site in need of bone formation or bone treatment. Thus, the method of the invention should not be construed to be limited solely to treat osteoporosis, but rather should be construed to include any disease or disorder where bone formation is desired and beneficial for the subject, including for example, osteonecrosis, osteomyelitis, osteoarthritis, Paget's disease, bone allograft rejection, bone autograft rejection, wear-debris induced osteolysis, bone cancer, or bone fracture.

In one embodiment, the method comprises forming a therapeutic-tethered macromer described herein. For example, the method comprises attaching a therapeutic agent described herein (e.g., BIO, GSK3β inhibitor XXVII) to a polymer to form a therapeutic-tethered macromer. In a particular embodiment, the method comprises forming a therapeutic-tethered macromer with at least one degradable bond between the therapeutic agent and the polymer. The at least one degradable bond allows for the controlled release of the therapeutic agent at the site in need of bone formation or bone treatment. The therapeutic agent may be attached to a polymer to form the therapeutic-tethered macromer by any suitable method known in the art, as described elsewhere herein.

In one embodiment, the method of the invention comprises administering the hydrogel to a site in need of bone formation or bone treatment. In one embodiment, the method comprises forming a suitable hydrogel ex vivo and then administering the hydrogel to a desired location in a patient or subject in need. In another embodiment, the method comprises administering a hydrogel solution to a location within the patient or subject, followed by inducing the polymerization of the hydrogel in vivo.

In certain embodiments, the hydrogel composition is administered to a site in the vicinity of a site in need of bone formation or bone treatment. As described elsewhere herein, the therapeutic agent (e.g., BIO, GSK3β inhibitor XXVII) is released from the hydrogel and is thereby able to promote bone formation at the site. In some instances, the hydrogel may also be embedded with one or more additional factors that are released from the hydrogel upon either hydrogel degradation or degradation of a linkage. Such factors include, but are not limited to, growth factors, hormones, immunosuppressive agents, antibiotics, bacteriocides, fungicides, proteins (e.g., BMPs), and the like. In some embodiments, the hydrogel is embedded with cells, including for example, osteoblasts, osteoprogenitor cells, stem cells, chondrocytes, and the like, that would aid promoting bone formation at the site.

The hydrogel may be administered in a variety of ways to a patient or subject in need. Modes of administration include intravenous, intravascular, intramuscular, subcutaneous, intracerebral, intraperitoneal, soft tissue injection, surgical placement, arthroscopic placement, and percutaneous insertion, e.g. direct injection, cannulation or catheterization. The methods described herein result in localized administration of the therapeutic agent comprising hydrogel to the site or sites in need of bone formation or bone treatment. Any administration may be a single application of a composition of invention or multiple applications. Administrations may be to a single site or to more than one site in the individual to be treated. Multiple administrations may occur essentially at the same time or separated in time.

In another embodiment, the method of the invention comprises promoting or inducing bone formation in a subject in need by administering an effective amount of a bone-homed particle, such as a micelle or nanoparticle, as described elsewhere herein. The bone-homed particle of the invention comprises a targeting domain that targets the particle to a site in need of bone formation or bone treatment. As described elsewhere herein, in one embodiment, the targeting domain comprises a domain that specifically binds to TRAP. For example, in one embodiment, the targeting domain comprises a peptide that specifically binds to TRAP. Thus, the method of the invention provides localized delivery of the therapeutic agent precisely at a site or sites in need of bone formation or bone treatment. In certain embodiments, the method comprises a systemic delivery (e.g. enteral or parenteral) of the bone-homed particle to provide localized release of the therapeutic agent.

In certain embodiments, the method comprises administering a pharmaceutical composition comprising the bone-homed particle. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical Compositions and Administration

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents include growth factors, hormones, anti-inflammatories including corticosteroids, and immunosuppressants, proteins (eg., BMPs), and the like.

Controlled- or sustained-release formulations of a pharmaceutical composition of the invention may be made using conventional technology.

For oral application, particularly suitable are tablets, dragees, liquids, drops, or capsules, caplets and gelcaps. Other formulations suitable for oral administration include, but are not limited to, a powdered or granular formulation, an aqueous or oily suspension, an aqueous or oily solution, a paste, a gel, a toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated, or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents, fillers, lubricants, disintegrates, or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose, or hydrogenated edible fats); emulsifying agent (e.g., lecithin or acacia); non-aqueous vehicles (e.g., almond oil, oily esters, or ethyl alcohol); and preservatives (e.g., methyl or propyl p-hydroxy benzoates or sorbic acid). Liquid formulations of a pharmaceutical composition of the invention that are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists of the use of materials that are solid or semi-solid at room temperature (i.e., having a relatively low softening or melting point range) to promote granulation of powdered or other materials, essentially in the absence of added water or other liquid solvents. The low-melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

Tablets may comprise multi-layer tablets comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles that comprise the active ingredient and that have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

It will be appreciated that a composition of the invention may be administered to a subject either alone, or in conjunction with another therapeutic agent.

The therapeutic and prophylactic methods of the invention thus encompass the use of pharmaceutical compositions comprising a therapeutic agent that induces or promotes bone formation to practice the methods of the invention. The pharmaceutical compositions useful for practicing the invention may be administered to deliver a dose of from ng/kg/day and 100 mg/kg/day. In one embodiment, the invention envisions administration of a dose that results in a concentration of the compound of the present invention between 0.1 µM and 10 µM in a mammal.

Typically, dosages which may be administered in a method of the invention to a mammal, preferably a human, range in amount from 0.5 µg to about 50 mg per kilogram of body weight of the mammal, while the precise dosage administered will vary depending upon any number of factors, including but not limited to, the type of mammal and type of disease state being treated, the age of the mammal and the route of administration. Preferably, the dosage of the compound will vary from about 1 µg to about 10 mg per kilogram of body weight of the mammal. More preferably, the dosage will vary from about 3 µg to about 1 mg per kilogram of body weight of the mammal.

The composition may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations that become evident as a result of the teaching provided herein.

Without further description, it is believed that one of ordinary skill in the art can, using the preceding description and the following illustrative examples, make and utilize the compounds of the present invention and practice the claimed methods. Therefore, the following working examples, specifically point out the preferred embodiments of the present invention, and are not to be construed as limiting in any way the remainder of the disclosure.

Example 1

Phage Display of TRAP-binding Peptide

Figure 1:
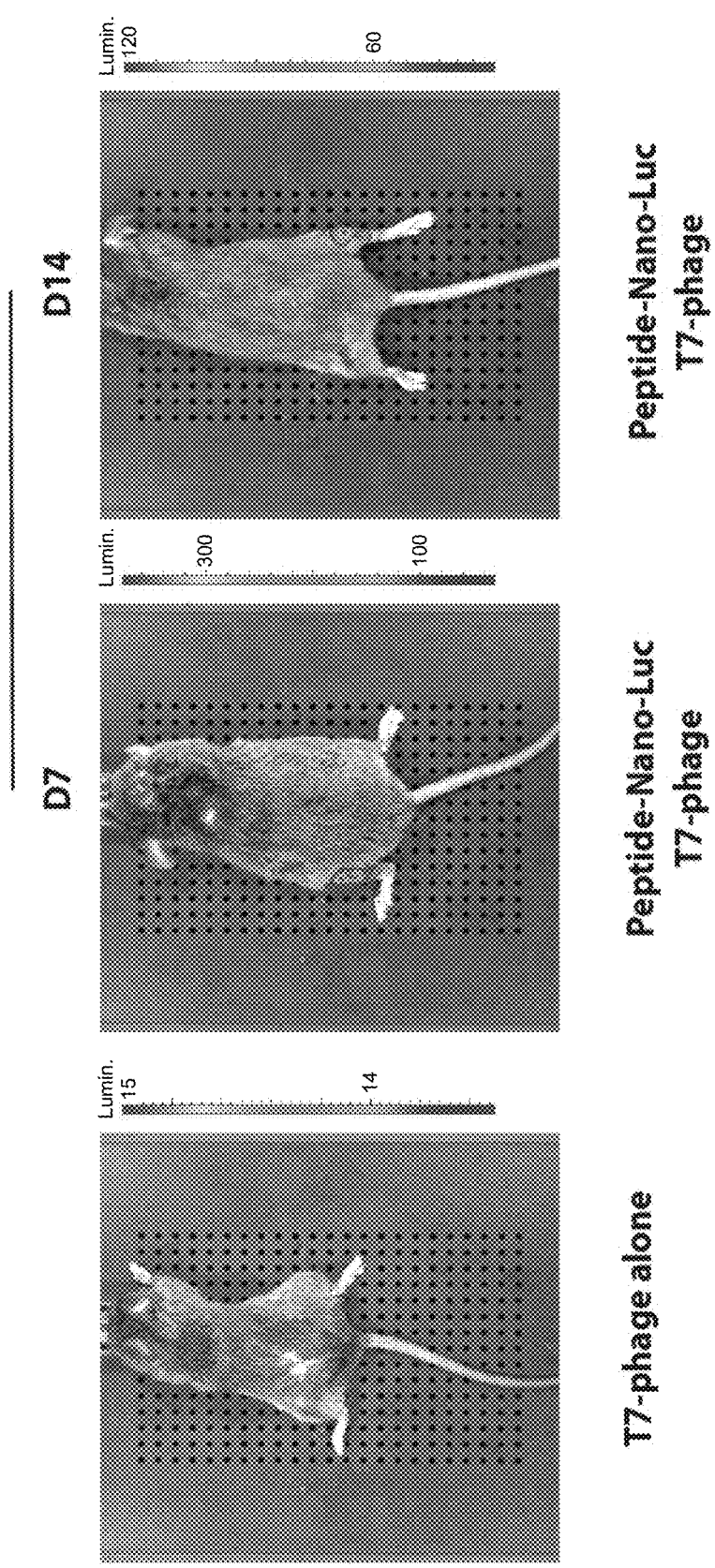
FIG. 1 is a set of images depicting the results of experiments using phage display of tartrate-resistant acid phosphatase (TRAP)-binding peptide to target sites of bone fracture. Peptide was presented via T7 phage and injected into mice at 7 days (center) and 14 days (right) post-tibia fracture ($10^{10}$/100 μl/mouse). Control phage not presenting the TRAP binding peptide is shown on the left. Imaging via IVIS shows luciferase expression of phage accumulating at fracture sites 1 hour after injection.

Experiments were conducted to evaluate the ability of tartrate-resistant acid phosphatase (TRAP)-binding peptide to home to sites of bone fracture using phage display of the peptide. TRAP-binding peptide (TPLSYLKGLVTV (SEQ ID NO: 3) was presented via T7 phage and injected into mice at 7 or 14 days post-tibia fracture ($10^{10}$/100 µl/mouse) (Sheu and Puzas, 2002, Bone Miner Res, 17(5): 915-22). Imaging via IVIS shows luciferase expression of phage accumulating at fracture sites 1 hour after injection (FIG. 1). Phage that do not present targeting peptide do not accumulate at fracture sites (day 7 is shown but day 14 was negative also). This data demonstrates that compositions comprising the TBP described herein can quickly and effectively target the composition to an active site of bone remodeling.

Example 2

Quantification of TRAP-binding Peptide Affinity to TRAP

The peptide TPLSYLKGLVTVG (SEQ ID NO: 1) was recently found to bind with high affinity (subnanomolar dissociation constant (KO) to the protein type V tartrate-resistant acid phosphatase (TRAP), which is deposited by osteoclasts during the resorption phase of bone remodeling. To exploit this peptide as a targeting mechanism for bone-homing particle described elsewhere herein, the following experiments were conducted.

The materials and methods employed in these experiments are now described.

Peptide and Peptide Monomer Synthesis

The TRAP-binding peptide sequence TPLSYLKGLVTV (SEQ ID NO: 3), discovered previously as having high nanomolar affinity for TRAP in phage form (Sheu and Puzas, 2002, Bone Miner Res, 17(5): 915-22), and a scrambled control VPVGTLSYLKLT (SEQ ID NO: 4), were synthesized at a 0.5 mmol scale on 0.7-meq $g^{-1}$-substituted fluorenylmethyloxycarbonyl (Fmoc)-Gly-Wang resin using microwave-assisted solid phase peptide synthesis and ultraviolet detection monitoring to yield peptide sequences of TRAP-binding peptide (TBP) (TPLSYLK-GLVTVG (SEQ ID NO: 1)) and scrambled control peptide (SCP) (VPVFTLSYLKLTG (SEQ ID NO: 2)). A peptide synthesizer with a microwave unit and ultraviolet detection monitoring is used for microwave-assisted solid phase peptide synthesis. Fmoc-protected amino acids are prepared at 0.2 M in N-methylpyrrolidone (NMP) and deprotected with 5% piperazine in in N,N-dimethylformamide (DMF). Amino acid decoupling is achieved with 0.5 M O-Benzo-triazole-N,N,N',N'-tetramethyl-uronium-hexafluoro-phosphate (HBTU) in DMF (activator) and 2 M N,N-diisopropylethylamine (DIEA) in NMP (activator base). A final deprotect cycle removes the Fmoc group from the final amino acid.

Peptides are cleaved and deprotected in a solution (20 mL per 0.5 mmol) of 92.5% trifluoroacetic acid (TFA), 2.5% distilled deionized water (ddH$_2$O), 2.5% triisopropylsilane (TIPS) and 2.5% 3,6-dioxa-1,8-octanedithiol (DODT) by rotating the mixture at room temperature for 2 hours on a mechanical rotator. The solutions are filtered to remove resin and precipitated into ice-cold diethyl ether. Precipitated peptides are collected via centrifugation (4000 rpm for 10 minutes), washed thrice with diethyl ether, and dried under vacuum overnight.

Figure 2:
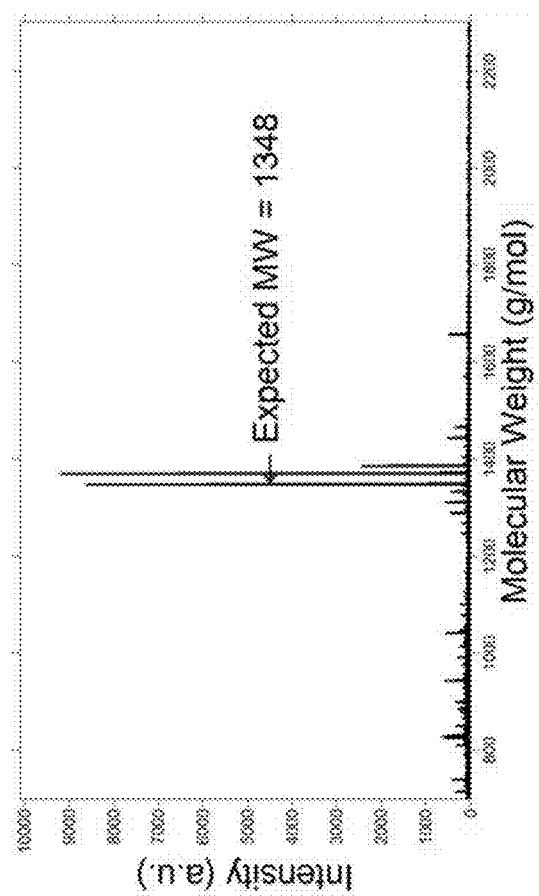
FIG. 2 depicts the MALDI-TOF spectra of correct peptide synthesis where high-intensity peaks beyond the molecular weight (MW) are peptides with electrostatically-bound sodium (23 Da) and potassium (39 Da) ions.

After cleavage and precipitation, correct synthesis and functionalization are validated using matrix assisted laser desorption/ionization time of flight (MALD-TOF) with α-cyano-4-hydroxycinnamic acid (CHCA) as the matrix. CHCA is dissolved in MALDI solvent (1:1 acetonitrile:ddH$_2$O with 0.1% TFA) at 10 mg mL$^{-1}$ and combined 1:1 with 1 mM peptides dissolved in MALDI solvent. Samples are spotted at 1 µL per spot on a MSP 96 target ground steel plate, dried, respotted, and dried before analysis. Calibration is performed using aliquotted peptide calibration standards spotted once at 1 μL per spot. MALDI identifies successful synthesis of TBP and SCP (FIG. 2).

Fluorescent Labeling of Peptides

Peptide is combined with N-hydroxysuccinimide (NHS), N,N-dicyclohexylcarbodiimide (DCC) and fluorescent cadaverine in a 1:2:2:2 ratio and dissolved in dimethyl sulfoxide (DMSO), and two drops of (DIEA) is added. The reaction vessel is stirred overnight. Dialysis against $dH_2O$ (1,000 g/mol cutoff) and lyophilization produces a fluorescently-labeled peptide.

Bone Resorption Pit Binding

Figure 3:
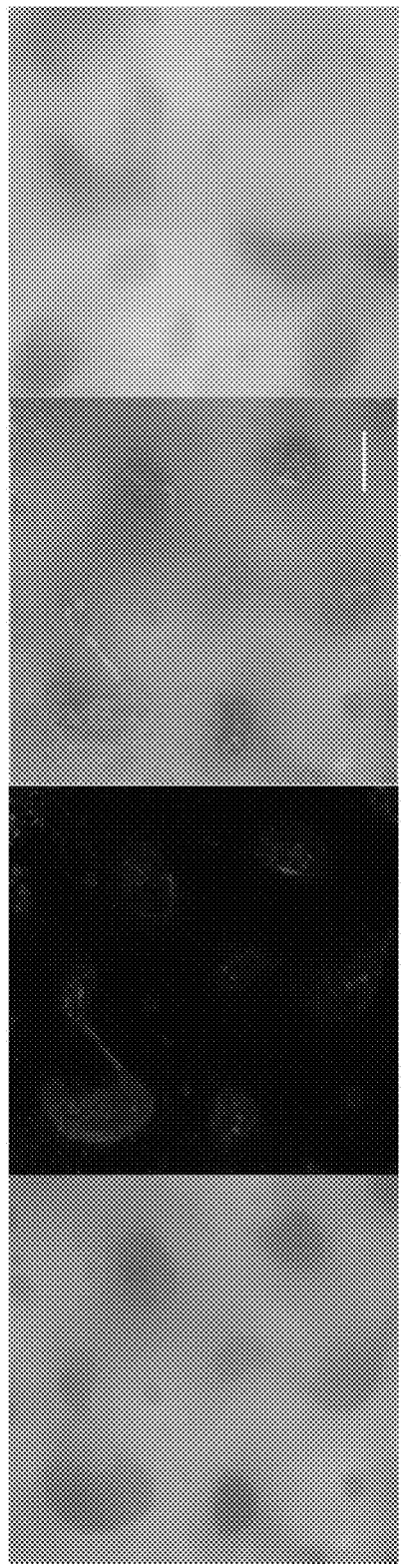
FIG. 3A, FIG. 3B, FIG. 3C, and FIG. 3D are images demonstrating that fluorescently-labeled TRAP-binding peptide specifically binds to bone resorption pits, which are dark regions in FIG. 3A and FIG. 3D (DIC, differential interference contrast, fluorescent (FIG. 3B, and merged DIC and fluorescent (FIG. 3C) confocal image). Control (SCP) merged DIC/fluorescent image is shown in (FIG. 3D). bar=200 μm.

Equal concentrations of fluorescently labeled TBP and SCP are prepared in 1× phosphate-buffered saline (PBS). Bone wafers are cut from cortical bone obtained from the femur of a human donor cadaver and incubated in peptide solutions overnight, washed twice with 1×PBS, and then visualized via confocal imaging. Stacked sections are compressed into 2D images to allow for qualitative analysis as in FIG. 3A through FIG. 3D. Applying fluorescently labeled peptides to bone wafers decorated with TRAP deposited during previous osteoclast activity results in specific binding of TBP to resorption pits (FIG. 3A to FIG. 3C). Qualitatively, no binding of SCP is detected (FIG. 3D).

Measurement of Peptide Affinity for TRAP Protein

Surface plasmon resonance (SPR) is used to assess the affinity of peptides for TRAP. Series S Sensor CM5 Chips are functionalized with TRAP via 1-ethyl-3-(3-dimethylaminopropyl) carbodiimide (EDC)/N-hydroxysuccinimide (NHS) chemistry. Briefly, the chips, which have a carboxymethylated dextran functionality, are activated through the introduction of NHS and EDC. After activation, TRAP protein, at 30 μg/mL in sodium acetate (pH=5), is introduced to the surface. Ethanolamine-hydrochloric acid is used to quench unreacted carboxysuccinimide groups. Peptides are dissolved in running buffer of PBS with 0.005% Tween20. Peptides are analyzed in duplicate at different concentrations. Surface regeneration is achieved using a combination of 1 and 2 M NaCl and 1-50 mM NaOH solutions as necessary. An unfunctionalized surface is used as a reference to eliminate signal due to nonspecific binding.

Figure 4:
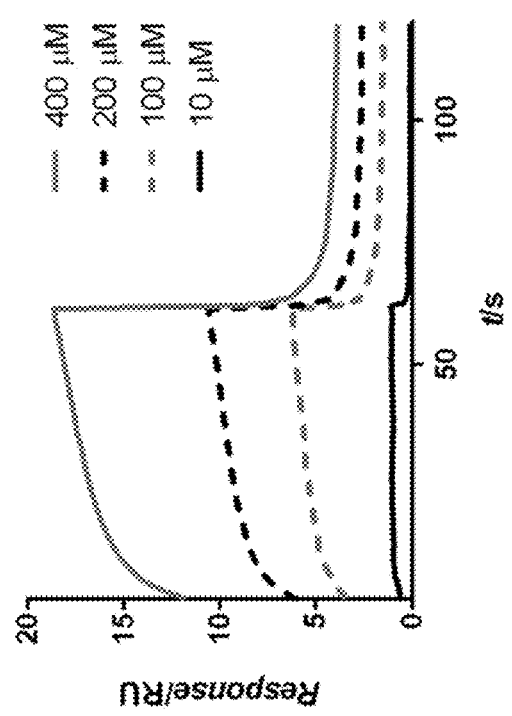
FIG. 4 depicts representative surface plasmon resonance (SPR) binding and dissociation curves for TBP. Injection of ligand begins at time zero seconds and lasts for one minute. The association of the sample during ligand injection is followed by a disassociation period of buffer injection. A positive relationship is observed between the response and concentration.

In SPR, the binding of any molecules to the surface of the sensor chips results in a change in the angle of incident light reflection, allowing highly-sensitive detection of miniscule amounts of ligand binding to the surface. Target affinity can be determined by introducing increasing concentrations of the ligand to the surface. Higher concentrations of samples elicited larger responses. The binding response was measured and plotted against concentration (FIG. 4), allowing for a fitting of the data by a binding curve. From this fitting, values such as $K_D$ can be determined. Through this technique, the affinity of TBP and SCP was analyzed. TBP showed affinity for TRAP ($K_D$~200 μM), while SCP resulted in responses that did not enable fitting of a binding curve or calculations of affinity. Despite the good affinity of TBP, it was lower (higher $K_D$) that expect from literature values ($K_D$~110 pM) (Sheu et al., 2002, Journal of Bone and Mineral Research, 17(5):915-922). While not wishing to be bound by any particular theory, a possible, but improbable, cause for difference in affinity is the inclusion of the glycine residue on the carboxylic end of the synthesized peptide used herein. Despite this addition, the order of the original sequence is preserved, and glycine is a small, uncharged and nonpolar amino acid. While not wishing to be bound by any particular theory, another more probable cause is the difference between a phage displayed peptide sequence and a lone peptide. In prior studies using phage display, five copies of the peptide are present and exposed (Sheu et al., 2002, Journal of Bone and Mineral Research, 17(5):915-922). Therefore, part of the higher affinity seen in the phage display experiments could be due to the multivalent nature of the peptide on the phage.

Cytocompatibility of Peptide-Functionalized Polymers

Mouse osteoblasts (MC3T3E1) were maintained in alpha minimum essential media (α-MEM, Gibco), containing 10% fetal bovine serum (FBS, Invitrogen) and 1% penicillin-streptomycin-fungizone at 37° C. and 5% $CO_2$. Cells were utilized at passage 5. To assess the cytocompatibility of peptide-functionalized polymers, cells were seeded in a 48 well plates at 10,000 cells/well and allowed to adhere overnight. Cells were treated with media alone or with peptide or peptide-functionalized polymers (0.1 mM and 10 mM) for 7 days, with media exchanges every two days. These concentrations employed are far higher than expected to be necessary for future uses and allowed for isolation of the maximum tolerated doses in vitro. After seven days of exposure, cells were washed, lysed by sonication, and analyzed for DNA concentration using the Picogreen Assay (Invitrogen). Results were normalized to cells treated with media alone.

Statistical Methods

Chi-squared values were used to determine the quality of fitting of binding curves. ANOVA was used to analyze for significance within cytotoxicity measurements.

The results of the experiments are now described

The TRAP binding peptide, TPLSYLKGLVTVG (SEQ ID NO: 1), and a scrambled control, VPVGTLSYLKLTG (SEQ ID NO: 2), were successfully synthesized and introduction of a methacrylamide group on the amine end was accomplished (FIG. 37A and FIG. 37B). Evaluation via spectroscopy revealed that the amount of peptide incorporated into polymers can be controlled through varying the initial monomer feed (Table 1). The affinity of the peptide-functionalized polymers for TRAP was measured with SPR, which revealed a higher affinity than the peptide alone, $2.17 \times 10^{-5}$ to $7.5 \times 10^{-6}$ M compared to $7.95 \times 10^{-4}$ M (FIG. 38A and FIG. 38B, Table 1). Furthermore the scrambled control peptide showed no affinity while the 0% peptide-functionalized polymer had an affinity order of magnitude lower, $2.5 \times 10^{-2}$. Peptide-functionalized polymers were determined to have minimal cytotoxic effects, with the 10% peptide-functionalized polymers being the most detrimental at both testing concentrations (FIG. 39A and FIG. 39B).

Peptides and peptide monomers were analyzed with respect to molecular weight by mass spectrometry as shown in FIG. 37A and FIG. 36B, with the expected increase in molecular weight with the addition of the methacrylamide group.

Synthesized polymers were characterized with respect to molecular weight and polydispersity index (PDI). As expected with RAFT polymerization, the PDIs of synthesized polymers was low, however the range of polymer molecular weights was larger than expected for a controlled polymerization. While not wishing to be bound by any particular theory, the variability in size of polymers could be due to insufficient purging with $N_2$, with the presence of oxygen retarding the polymerization process or the size of the peptide monomers could produce some steric hindrance. An observed trend of decreasing molecular weight with increasing amounts of peptide supports this theory. Absorbance spectroscopy was used to calculate the amount of peptide incorporation achieved in the polymer formulations with different ratios of initial monomers. As the ratio of peptide:PEG monomers in the polymer precursor solution was increased the expected increase in levels of peptide incorporation was also seen in the final polymers.

Quantitative analyses of peptide and polymer affinities were performed using SPR. TRAP-functionalized surfaces were formed and the binding affinity for peptides and polymers were tested, using an unfunctionalized surface as a reference to eliminate signal due to nonspecific binding. The binding of any molecules to the surface of the sensor chips results in a change in the angle of incident light reflection, allowing highly-sensitive detection of miniscule amounts of ligand binding to the surface. Target affinity can be determined by introduction of increasing concentrations of the molecule to the surface (FIG. 38A and FIG. 38B). Typically higher concentrations of samples elicited larger responses, with a larger response from polymers at lower concentrations in comparison to the TBP alone. In addition to their greater response a slower disassociation was seen in the peptide-functionalized polymers, compared to the abrupt return to the baseline in peptide samples. Furthermore, polymer samples required the application of regeneration buffers, ranging from a mild buffer of 500 mM NaCl to a harsher buffer of 5 mM NaOH, to return the signal to previous levels. The binding response is measured and plotted against concentration, allowing for a fitting of the data by a binding curve. From this fitting, values such as the dissociation constant ($K_D$) value can be determined. Through this technique, the affinity of peptides and peptide-functionalized polymers were analyzed. TBP showed affinity for TRAP ($K_D$~700 µM), while the scrambled peptide resulted in responses that did not enable fitting of a binding curve or calculations of affinity. Control polymer, e.g., those that included no peptide functionalities, exhibited low, albeit detectable affinities for TRAP ($K_D$~2 mM). While not wishing to be bound by any particular theory, these observed affinities may be due to non-specific binding resulting from the hydrophobic poly(methacrylate) backbone within PEGMMA polymers, despite PEG's inert and hydrophilic nature. However, inclusion of peptide functionalities results in substantial increases in TRAP affinities ($K_D$~7.1-21 µM). Despite the good affinity of TBP alone, it was lower than expected from literature values ($K_D$~110 pM) (Sheu et al., 2002, Journal of Bone and Mineral Research, 17(5): 915-922). While not wishing to be bound by any particular theory, a possible, but improbable, cause for difference in affinity is the inclusion of the glycine residue on the carboxylic end of the synthesized peptide used herein. Despite this addition the order of the original sequence is preserved and glycine is a small, uncharged and nonpolar amino acid. While not wishing to be bound by any particular theory, another, more probable cause is the difference between a phage displayed peptide sequence and a lone peptide. In prior studies using phage display, five copies of the peptide are present and exposed (Sheu et al., 2002, Journal of Bone and Mineral Research, 17(5): 915-922). Therefore part of the higher affinity seen in the phage display experiments could be due to the multivalent nature of the peptide on the phage.

TABLE 1

Molecular weights, peptide incorporation and TRAP affinities for TRAP of different initial monomer concentrations (n = 2, Ave. ± StDev).

| % Peptide Monomer | Mn (Da) | % Peptide Incorporated | $K_D$ (M) |
|---|---|---|---|
| TBP | 1348 | N/A | $7.95 \times 10^{-4} \pm 2.33 \times 10^{-4}$ |
| Scrambled | 1348 | N/A | N/A |
| 0 | 34200 ± 5200 | 0.2 ± 0.3 | $2.5 \times 10^{-2} \pm 3.25 \times 10^{-2}$ |
| 5 | 103900 ± 3000 | 3.9 ± 2.5 | $2.17 \times 10^{-5} \pm 2.21 \times 10^{-5}$ |
| 10 | 69000 ± 38800 | 7.5 ± 1.3 | $1.27 \times 10^{-5} \pm 1.79 \times 10^{-5}$ |
| 20 | 26700 ± 4200 | 17.1 ± 8.3 | $7.5 \times 10^{-6} \pm 3.47 \times 10^{-6}$ |

In addition to successful targeting of drugs to specific tissue therapeutic, polymers should be cytocompatible. To evaluate the cytocompatibility of these peptide-functionalized polymer mouse osteoblasts (MC3T3E1) were used due their proximity to the target area and being the eventual treated cell type. Peptide-functionalized polymers reduced viability to some extent but at very high concentrations (FIG. 39A and FIG. 39B). Peptides can induce cell death by increasing the permeability of the cell membrane, which can result in cell lysis (Johnstone et al., 2000 Anti-Cancer Drug Des 15(2): 151-160).

For example, peptide-functionalized polymers reduced cell viability to a similar extent, ~75% of controls, at the highest concentrations tested but only very modestly (~90%) at the 0.1 mM concentrations. Interestingly, % peptide incorporation did not correlate with viability, as the 10% peptide-functionalized polymer exhibited the worst cytocompatibility of all polymers tested, however this could be due to the larger 10% polymers containing more peptides per polymer despite their lower percentage. In this case, while the polymer concentrations are equal the peptide concentration is actually higher in the 10% polymer.

The studies presented herein demonstrate the feasibility of targeting TRAP protein via synthesis of peptide-PEG copolymers. Methacrylamide functionalized peptides were successfully introduced to PEG polymers, via addition as monomers during the polymerization process, at different percentages of the total polymer. Variation in peptide incorporation levels with change in initial monomer ratios was measured by absorption and showed the expected trend of increasing peptide incorporation with an increase in initial peptide:PEG monomer ratio. TBP demonstrated measurable affinity for TRAP and improved when incorporated into polymers in a multivalent fashion. Peptide-functionalized polymers demonstrated low cytotoxicity, compared to untreated cells, at high concentrations.

Example 3

Figure 5B:
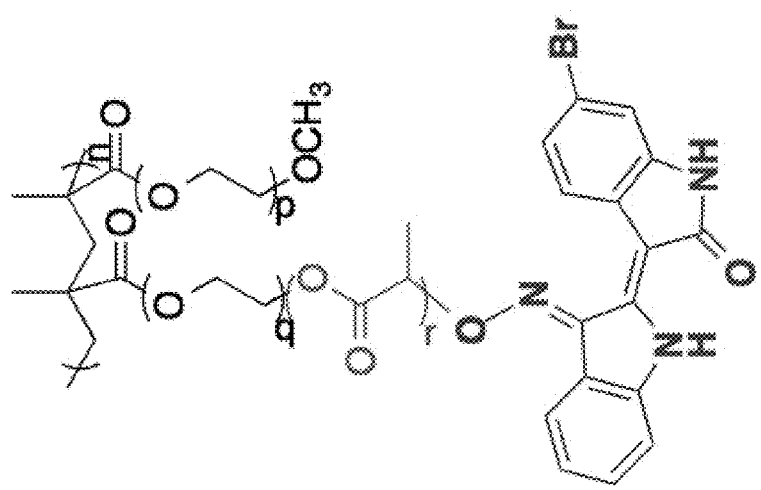
FIG. 5A and FIG. 5B depict exemplary therapeutic-tethered macromers of the invention. Depicted is bromoindirubin-3'-oxime (BIO), a specific inhibitor of glycogen synthase kinase 3 beta (GSK3β) (FIG. 5A) and a BIO-releasing macromer (FIG. 5B). BIO (blue) is attached to poly(ethylene glycol) methacrylate by hydrolytically degradable ester bonds residing within a lactide (lactic acid) tether (red). n, p/q, and r represent units of polymer repeats, PEG repeats, and lactide repeats, respectively.
Figure 5A:
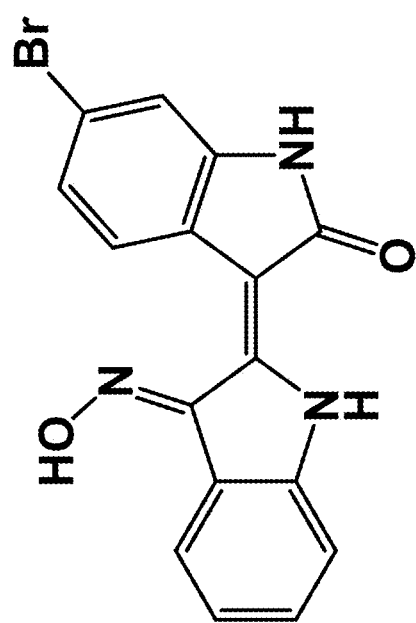

Development of a Polymer Therapeutic Targeted to Bone Resorption Sites 6-bromoindirubin-3'-oxime (BIO) (FIG. 5A) is a small molecule that enhances bone production by osteoblasts through selective inhibition of glycogen synthase kinase 3 beta (GSK3β), which is an inhibitor of the Wnt/β-catenin pathway (Wang, 2009, Life Sciences, 85(19-20): 685-692). BIO has the potential to overcome osteoporosis regardless of the initiating biological event (environmental toxin exposure, disuse, menopause) through rescue of the Wnt/β-catenin pathway. However, delivery of BIO and other small molecule drugs to bone is very difficult due to significant delivery barriers. For example, systemic availability of small molecule drugs after oral administration is very low (<1%) (Garrett and Mundy, 2002, Arthritis Res 4(4):237-40; Grey, 2007, Expert Opin Emerg Dr 12(3):493-508; Mundy, 2001, Bone 29(6):495-7), particularly in bone tissue, due to rapid degradation in the liver and renal clearance. In addition, BIO has poor water solubility due to its hydrophobicity, making it difficult to achieve therapeutic levels within the body (Vougogiannopoulou et al., 2008, Journal of Medicinal Chemistry, 51(20): 6421-6431). Moreover, a lack of bone specificity and biodistribution lowers the clinical potential of therapeutic agents that modulate Wnt/β-catenin signaling and can lead to serious complications due to off-target effects. There is abundant literature linking Wnt signaling to a variety of tumors (Clevers, 2006, Cell 127(3):469-80;

Kansara et al., 2009, J Clin Invest 119(4):837-51). However, concerns are somewhat mitigated as Wnt agonism using long-term lithium chloride treatment, which acts similarly to BIO in Wnt signaling and has been employed to treat neurological diseases, is not associated with an increase in cancer prevalence (Gong et al., 2001, Cell 107(4):513-23; Little et al., 2002, Am J Hum Genet 70(1):11-9; Loots et al., 2005, Genome Res 15(7):928-35).

Figure 6:
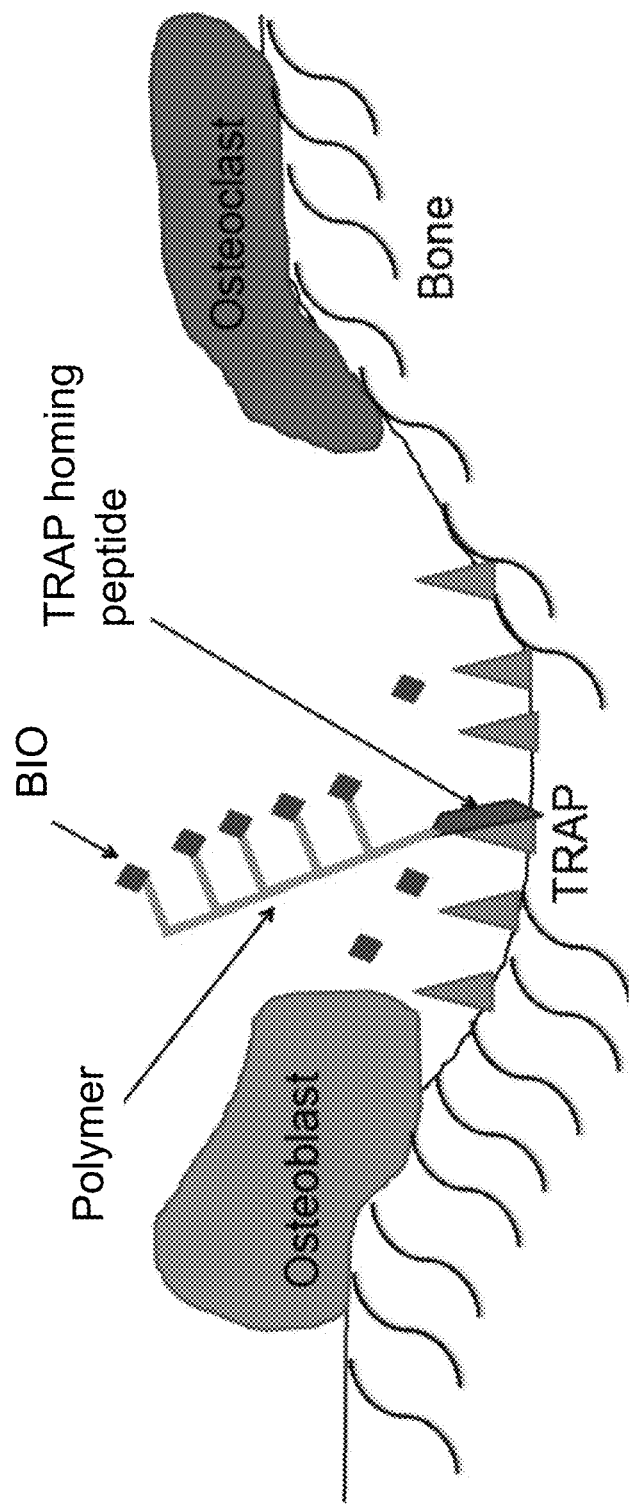
FIG. 6 is an illustration depicting a resorption pit with polymer therapeutic homing to TRAP molecule deposited by osteoclasts.

A major opportunity exists to develop an appropriate delivery system for BIO to gain access to this important class of osteoporosis therapeutics. The present invention includes the development of a novel polymer therapeutic (FIG. 6) to deliver the drug specifically to the site of resorption to selectively enhance osteoblast activity, resulting in greater bone production. Polymer therapeutics possess a plethora of advantages. In addition to increasing the solubility of drug being delivered, they also protect the molecule from degradation, increase circulation time and achieve higher concentrations at target sites (Zalipsky, 1995, Advanced Drug Delivery Reviews, 16(2-3): 157-182). BIO (FIG. 5A) can be covalently tethered to poly(ethylene glycol) (PEG) methacrylate through hydrolytically degradable bonds (FIG. 5B) and exploited as a monomer for subsequent polymerizations. PEG is used to increase the solubility and circulation time of BIO. The overall dose and release rate of BIO can be tuned based on conjugate chemistry and feed ratio in polymerizations (Benoit et al., 2006, Biomaterials, 27(36): 6102-6110). To target BIO delivery, the presence of tartrate-resistant acid phosphatase (TRAP), a protein left behind by osteoclasts in resorption sites (Matsuo and Irie, 2008, Archives of Biochemistry and Biophysics, 473(2): 201-209), is exploited. A peptide that homes to TRAP (Sheu et al., 2002, J Bone Miner Res, 17(5): 915-922) is incorporated into the delivery system. This results in concentration of the drug at resorption pits to enhance osteoblast bone production.

Targeted, highly controlled polymer delivery systems for BIO are herein described, providing bone specificity at the exact sites of bone resorption. By incorporating bone-homing mechanisms to drugs, pharmacokinetic profiles can be dramatically altered to favor skeletal delivery as exemplified by bisphosphonate drugs, which specifically bind to calcium present within bone hydroxyapatite. Moreover, the delivery of BIO is tightly controlled through degradable chemistries, enabling optimization of dose and treatment duration to restore β-catenin signaling, providing bone anabolic effects but not overshooting osteoblast activation, which may result in hyperossification.

Through design and implementation of polymer therapeutics, the delivery hurdles of BIO are overcome. As every known bone disease causes local inflammation, resulting in an increase of vasculature and blood exposure, drug homing to bone can be enhanced due to the 'Enhanced Permeation and Retention' (EPR) effect (Duncan et al., 2006, J Drug Target 14(6):337-41; Vicent et al., 2008, Expert Opin Drug Del 5(5):593-614). The EPR effect describes how polymer therapeutics, due to their molecular weight, passively accumulate at sites of leaky vasculature—e.g., at sites of inflammation, making polymer therapeutics an exciting option for selective delivery of drugs to bone. Polymer therapeutics also result in higher plasma drug concentrations, lower renal clearance, longer circulation half-lives, higher (up to 50-fold) concentrations within target tissues than small molecule drugs (Duncan, 2003, Nat Rev Drug Discov 2(5): 347-60; Kiick, 2007, Science 317(5842):1182-3; Setton, 2008, Nat Mater 7(3):172-4; Vicent et al., 2008, Expert Opin Drug Del 5(5):593-614), enhance the stability of therapeutic molecules, reduce immunogenicity, and improve drug solubility properties. Wang et al. studied bone EPR using N-(2-hydroxypropy) methacrylamide (HPMA)-based polymers (Wang et al., 2006, Mol Pharmaceut 3(6):717-25). HPMA, a hydrophilic polymer, enhanced circulation time and bone accumulation of a model small molecule drug. In comparing a range of polymer molecular weights (24-96 kDa), the greatest delivery advantages was observed using a 24 kDa polymer, which provided the greatest selectivity towards bone, with the highest bone to reticuloendothelial system (RES) accumulation ratio. Numerous other polymer-drug conjugates have been applied clinically to exploit the EPR effect to target sites of inflammation, most commonly in the context of cancer. These conjugates include poly(ethylene glycol) (PEG)-modified adenosine deaminase, L-asparaginase, camptothecin and HPMA conjugates with doxorubicin and camptothecin (Vicent et al., 2008, Expert Opin Drug Del 5(5):593-614). In experiments described herein, PEG is used as a polymer to develop a specific, controlled BIO-delivery system. PEG has been routinely used in vivo pharmacologically (e.g., interferon gamma, PEGASYS (Roche)) and it is well established that PEG is excreted renally if it is under the molecular weight of 100 kDa. The present studies use 24 kDa PEG. Moreover, the drug delivery degradation products, which include just PEG alone or lactic acid or lactic acid oligomers have been proven safe as poly(lactic acid), which degrades into the same monomers, has been FDA approved for >20 years use in humans as a suture material.

The experiments described herein utilize a controlled living polymerization strategy known as reversible-addition fragmentation chain transfer (RAFT) for developing polymers with well-controlled molecular weight and polydispersities, polymer chain ends with different end functionalities, and a multitude of architectures. These characteristics are of great importance to the development of polymer therapeutics. Precise definition of molecular weight and structure is inherently important for reproducible therapeutic manufacturing and FDA approval while the large variety in architectures enables design-on-demand, depending on the distinct requirements of the delivery system. For example, dendrimers or brush architectures and also the end-functional nature of these polymers impart the ability to mix-and-match drugs, targeting, or other functional moieties, building a drug with specific characteristics. In addition, the flexible design capabilities of RAFT polymers improve stability of therapeutic molecules, reduce immunogenicity, enhance solubility, and increase blood circulation times to achieve high doses of therapeutic at the right time, at the right place, and at the right concentrations.

The studies described herein demonstrate the development of targeted polymeric drug delivery systems to enable targeted delivery of anabolic agents to treat osteoporosis. The developed technology is described as follows. The polymeric delivery system provides therapeutic efficacy to potent bone anabolic drugs not currently used due to rapid clearance and low bone tissue concentrations by exploiting polymer-mediated delivery through EPR. Further, the system enables localized drug delivery specifically at bone resorption pits to enhance osteoblast bone production, through simple incorporation of targeting peptides. Further, the system affords control over drug dose and duration of delivery using established, controlled release chemistries. The described systems are assembled using robust, versatile chemistry for broader applications (e.g., delivery of other drugs for osteoporosis or other skeletal diseases).

The materials and methods used in these experiments are described.

Peptide Synthesis and Purification

A peptide shown to home to TRAP (Sheu et al., 2002, J Bone Miner Res, 17(5): 915-922) elsewhere herein, TPL-SYLKGLVTVG (SEQ ID NO: 1) (TBP), was synthesized using solid phase peptide synthesis and cleaved from the resin as described in Example 2. Purification of the TBP was achieved through the use of high performance liquid chromatography (HPLC). Initially, tests were run on an analytical column to identify the peak containing the TBP. A binary gradient was run with water and acetonitrile, both containing 0.1% trifluroacetic acid (TFA), with acetonitrile starting at 5% and ending at 95%. The acetonitrile and TFA were removed by dialysis (1,000 g/mol cutoff) against $dH_2O$. Water was removed via lyophilization. The presence and purity of the peptide was determined through the use of matrix assisted laser desorption/ionization (MALDI), as described in Example 2. Once the peak containing the peptide had been identified, the HPLC method was scaled up to implement the use of a semi-preparative column and increase rate of collection. MALDI (similar to FIG. 33) indicated peptide purification was achieved using HPLC; however yield was very low due to limitations in the amount of peptide loading.

Synthesis and Characterization of RAFT-mediated PEG Polymers

Figure 7:
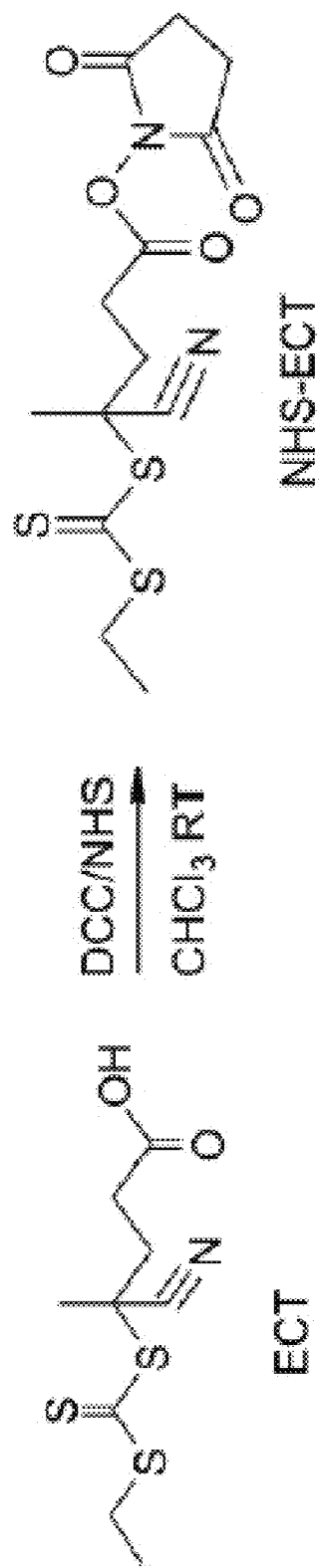
FIG. 7 is a schematic depicting the chemical scheme for synthesis of peptide-conjugated ECT.

Polymers were synthesized using the controlled, living polymerization technique known as reversible addition-fragmentation chain transfer (RAFT) (Table 2). This technique uses a chain transfer agent (CTA) that is capable of maintaining the radical state of the propagating species or reinitiating polymerization and yields polymers with low polydispersity index (PDI), indicative of uniform polymers. Furthermore, the presence of functional groups of the CTA on either end of the growing polymer chain allows for facile end-functionalization of the polymer (Barner-Kowollikm, 2008, Handbook of RAFT Polymerization, Wiley-VCH). The CTA, 4-cyano-4-(ethylsulfanylthiocarbonyl) sulfanyl pentanoic acid (ECT), was synthesized by a procedure adapted from previously reported methods (Moad et al., 2005, Polymer, 46(19): 8458-8468). In order to incorporate the TBP into the polymer, the CTA was conjugated to an appropriate leaving group, in this case N-Hydroxysuccinimide (NHS) to enable it to react with the amine terminus of the TBP (FIG. 7). Briefly, ECT (1.05 g, 4 mmol) in chloroform ($CHCl_3$) was combined with NHS (460 mg, 4 mmol) and dicyclohexylcarbodiimide (865 mg, 4.2 mmol). The reaction proceeded for 1 hour at 0° C. then at room temperature for another 22 hours (Benoit et al., 2011, Biomacromolecules, 12(7): 2708-2714). It was filtered and washed with $CHCl_3$ and concentrated using rotary evaporation. The final product was placed under vacuum. Conjugation was verified with 1H-NMR ($CDCl_3$) (data not shown).

TABLE 2

BIO-tethered polymers made with RAFT polymerization
BIO-tethered Polymers

| % BIO conjugated | MW (g/mol) | PDI |
|---|---|---|
| 5 | 36,600 | 1.12 |
| 10 | 42,000 | 1.17 |

Figure 8:
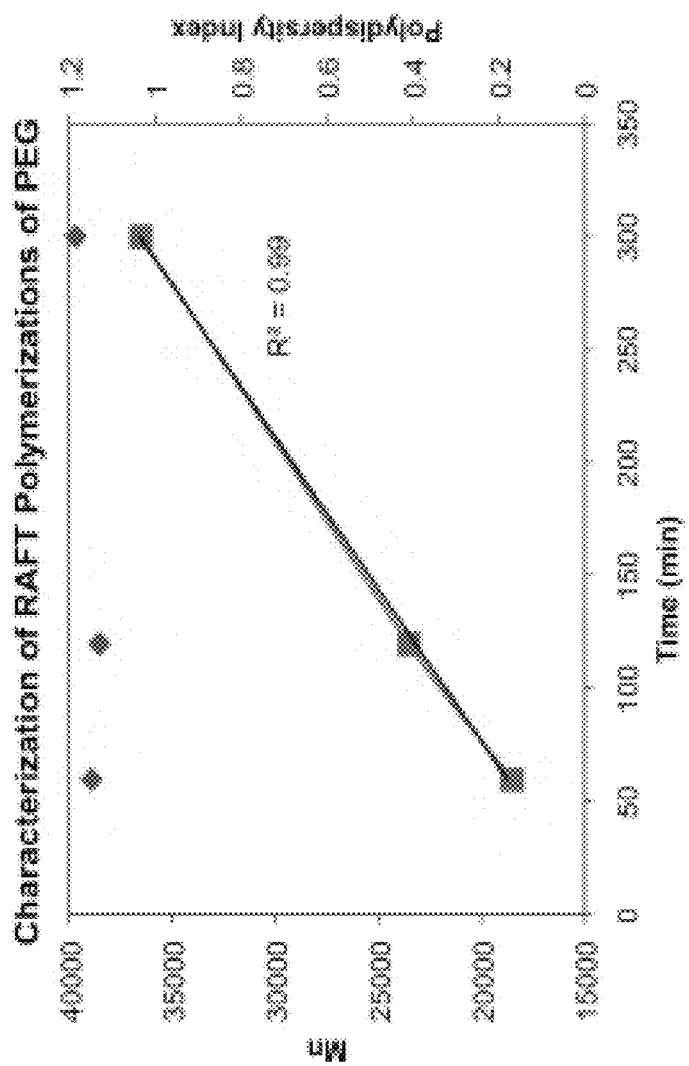
FIG. 8 is a graph depicting the results of experiments demonstrating that RAFT polymers formed of poly(ethylene glycol) monomethylether methacrylate show characteristics of living, controlled polymerizations. Specifically, observed polydispersity index is below 1.2 for all time points. In addition, the relationship between time and molecular weight (Mn) is linear, indicating there is good control.

The polymer was synthesized first with ECT (no targeting peptide) to determine appropriate RAFT conditions. Poly (ethylene glycol) monomethylether methacrylate (2 g, 6 mmol) was combined with ECT CTA (11.06 mg, 40 µmol), azobisisobutyronitrile (AIBN) (0.73 mg, 40 µmol) as an initiator, and dimethylformamide (2 g). Samples were purged with $N_2$ gas to remove oxygen and then suspended in a 60° C. oil bath. Polymerization was terminated at different time points by removing a sample from the oil bath and exposing the sample to air. Resultant polymers were analyzed with gel permeation chromatography (GPC) as shown in FIG. 8.

Confirm and Compare Binding of TBP and TBP-functionalized Polymer Therapeutics

Qualitatively, bone binding of fluorescently-labeled polymers is investigated using confocal microscopy as in Example 2. Briefly, TBP-conjugated and control (PEG only and SCP-conjugated) polymers are solubilized at 1 mg/ml in 1xPBS and incubated at 37° C. overnight on cortical bone wafers. Wafers are then washed in 1xPBS and imaged via confocal microscopy. Stacked sections are compressed into 2D images to allow for qualitative analysis as in FIG. 3A through FIG. 3D. Binding affinity of the peptide, peptide conjugates (TBP and control), and PEG alone are also analyzed quantitatively using a binding assay as described previously (Rodan and Fleisch, 1996, J Clin Invest 97(12): 2692-6) using TRAP-coated plates. This is used to quantitatively compare between binding constants ($K_D$) of the targeting group compared with the targeted polymer and ensure controls are proper (e.g., do not home to TRAP). Though it is appreciated that this is a very favorable assessment of $K_D$ compared with in vivo, it is necessary to ensure that the polymer does not interfere with TRAP-homing of the peptide appreciably. In instances where homing is disrupted by greater than 10% differences in $K_D$ values, this reduction in affinity may be overcome by using spacers between the peptide and polymer and/or incorporate multiple peptides/polymer chain to recoup affinity established by the peptide alone.

Characterize Anabolic Agent (BIO) Release from Polymer Therapeutics.

Figure 9:
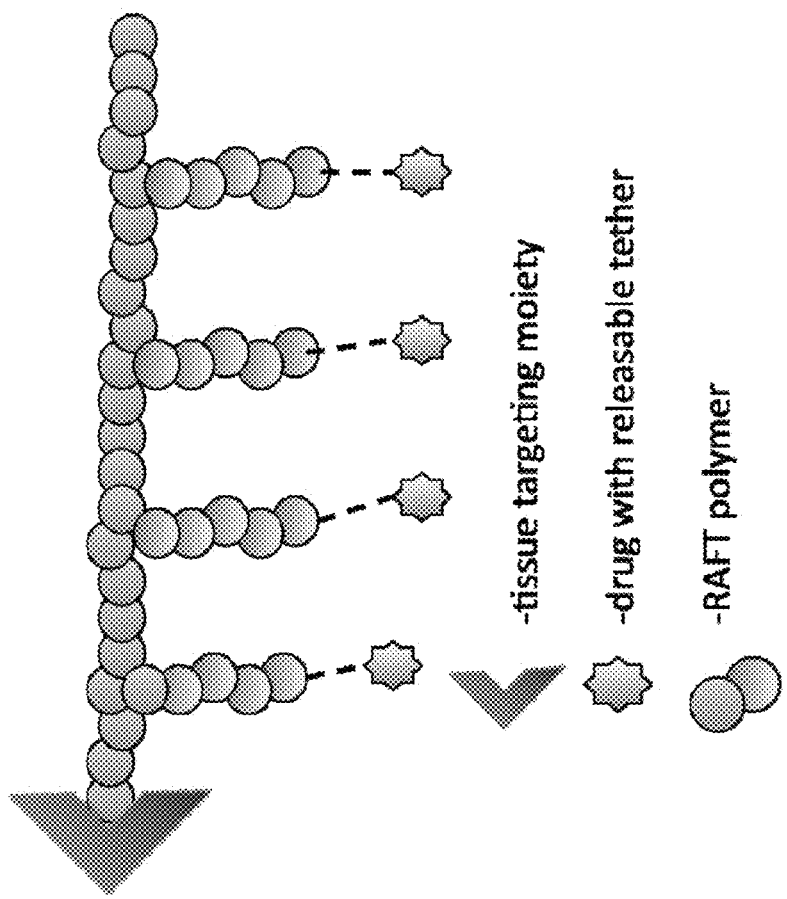
FIG. 9 is an illustration of an exemplary composition of the invention. Use of high-density architectures, such as brush architectures, enable delivery of high concentrations of drug with tissue specificity through targeting moieties.
Figure 10C:
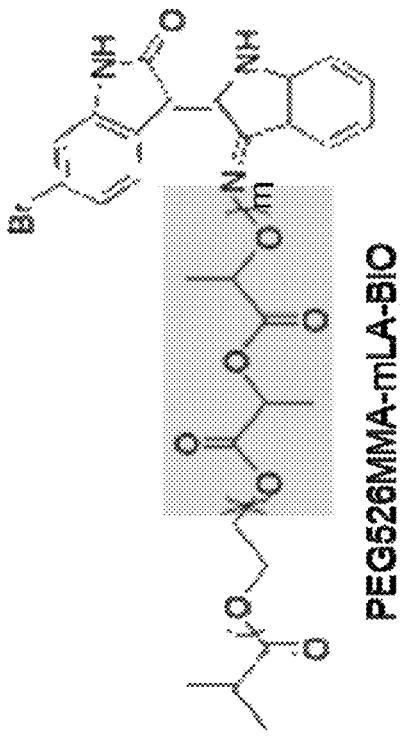
FIG. 10A, FIG. 10B, FIG. 10C, and FIG. 10D depict a set of structures depicting various components of an exemplary composition of the invention.
Figure 10D:
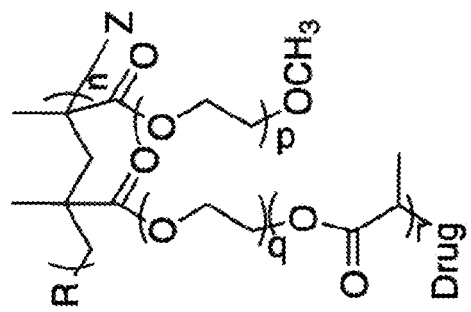
Figure 10A:
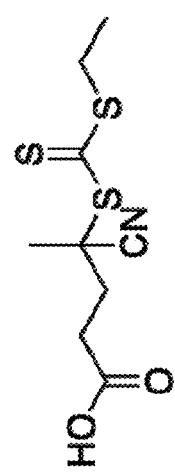
Figure 10B:
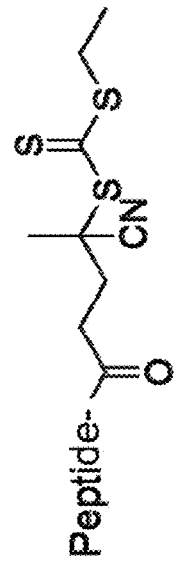
Figure 11:
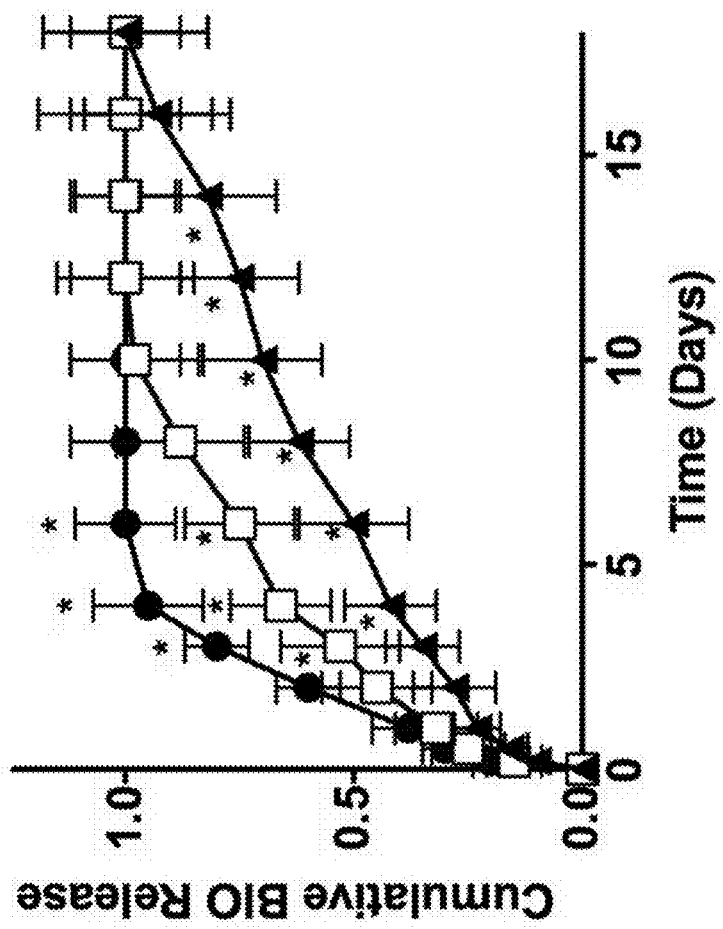
FIG. 11 is a graph demonstrating the controlled release of BIO, in the context of polymers described in FIG. 10D.

To produce high-density incorporation of drug-releasable tethers into polymers, brush polymers (FIG. 9) were synthesized using RAFT polymerization. RAFT has been used as an effective strategy to synthesize controlled molecular weight polymers with functional end groups for targeting (Benoit et al., 2009, J Control Release 133(3):221-9; Duvall et al., 2010, Mol Pharmaceut 7(2):468-76; Henry et al., 2009, Bioconjugate Chem 20(6):1122-8). These copolymers are composed of poly(ethylene glycol) and poly(ethylene glycol)-based BIO-releasable tethers (see FIG. 10C). The BIO-releasing tether are synthesized as performed previously (Benoit et al., 2006, Biomaterials 27(36):6102-10; Nuttelman et al., 2006, Biomaterials 27(8):1377-86; Nuttelman et al., 2006, J Biomed Mater Res A 76(1):183-95) where the mechanism for BIO release is through hydrolytic degradation of ester bonds of the lactic acid units. Similar release systems have been previously utilized to control the release of other small molecule drugs, dexamethasone and fluvastatin. As shown in FIG. 11, there was a sustained delivery of active BIO from polymers over ~18 days; the overall dose is controlled by tethered drug concentration whereas the release rate is controlled by the chemistry and length of the degradable lactide linker (Benoit et al., 2006, Biomaterials 27(36):6102-10; Nuttelman et al., 2006, Biomaterials 27(8):1377-86; Nuttelman et al., 2006, J Biomed Mater Res A 76(1):183-95). The choice of PEG as the material for these polymer-drug conjugates is based on its ability to impart favorable properties to drug-conjugates, as it is hydrophilic and inert and prevents non-specific accumulation of drug in off-target tissues. In addition, it is employed in a number of FDA-approved drugs. Drug conjugates with molecular weights of ~24 kDa were targeted. However, a broader range (10-50 kDa) was tested depending upon achieved circulation time and biodistribution of the 24 kDa conjugates (goal is increasing BIO circulation time from <2 min to >1 hour and achieving a bone to RES accumulation ratio of 10 or greater). 24 kDa molecular weights have been previously shown to provide favorable pharmacokinetic properties (increased blood circulation time and target tissue accumulation) while still allowing for renal excretion of the polymer once it has delivered its drug payload, thus minimizing side effects from the polymer itself (Lipton et al., 2007, Leuk Lymphoma 48(3):497-505; Reddy et al., 2009, J Viral Hepat 16(10):724-31; Talpaz et al., 2005, Clin Cancer Res 11(17):6247-55; Zeuzem et al., 2008, J Hepatol 49(2):157-9; Zeuzem et al., 2004, Gastroenterology 127(6):1724-32). These polymers were verified to be on target with respect to molecular weight (~24 kDa) and also characterized for polydispersity. The incorporation and release of BIO over time is analyzed using a combination of nuclear magnetic resonance spectroscopy (NMR), size exclusion chromatography (SEC), mass spectrometry, and high performance liquid chromatography (HPLC) (FIG. 12). Further, aspects of polymer architecture are systematically varied to enable tuning of characteristics such as drug release rate, concentration, and longevity of drug release. These characteristics include: (a) overall amount of drug incorporation and (b) length of degradable tether.

Example 4

Multivalent Peptide-Targeted Drug Delivery Systems

Tartrate-resistant acid phosphatase (TRAP)-binding peptide (TBP) alone falls short of the subnanomolar affinity of TRAP-binding peptide-functionalized phage ($K_D$~200 µM vs. $K_D$~110 pM). While not wishing to be bound by any particular theory, it is possible the multivalency of phage imparts greater TRAP affinity. The studies described herein demonstrate the development of multivalent, targeted polymeric drug delivery systems to increase the affinity of targeted anabolic agents to treat osteoporosis.

Peptide Monomer Synthesis and Cleavage

The TRAP-binding peptide sequence TPLSYLKGLVTV (SEQ ID NO: 3), discovered previously identified as having nanomolar affinity for TRAP in phage form (Sheu and Puzas, 2002, Bone Miner Res, 17(5): 915-22), and a scrambled control peptide (SCP), VPVGTLSYLKLT (SEQ ID NO: 4), are synthesized at a 0.5 mmol scale on 0.7-meq $g^{-1}$-substituted fluorenylmethyloxycarbonyl (Fmoc)-Gly-Wang resin using microwave-assisted solid phase peptide synthesis and ultraviolet detection monitoring to yield peptide sequences of TRAP-binding peptide (TBP) (TPLSYLKGLVTVG (SEQ ID NO: 1)) and scrambled control peptide (SCP) (VPVFTLSYLKLTG (SEQ ID NO: 2)). A peptide synthesizer with a microwave unit and ultraviolet detection monitoring is used for microwave-assisted solid phase peptide synthesis. Fmoc-protected amino acids are prepared at 0.2 M in N-methyl-2-pyrrolidone (NMP) and deprotected with 5% piperazine in N,N-dimethylformamide (DMF). Amino acid coupling is achieved with 0.5 M O-Benzotriazole-N,N,N',N'-tetramethyl-uronium-hexafluoro-phosphate (HBTU) in DMF (activator) and 2 M N,N-diisopropylethylamine (DIEA) in NMP (activator base). A final deprotect cycle removes the Fmoc group from the final amino acid to expose a primary amine for further functionalization (FIG. 13). On-resin peptides with the final Fmoc removed but protecting groups remaining are submerged in methacrylic anhydride in a 20-mL scintillation vial and microwaved at full power for 3 minutes, vortexing every 45 seconds. Once cooled, on-resin peptides were washed with DMF and filtered.

Peptide monomers are cleaved and deprotected in a solution (20 mL per 0.5 mmol) of 92.5% trifluoroacetic acid (TFA), 2.5% distilled deionized water (ddH$_2$O), 2.5% triisopropylsilane (TIPS) and 2.5% 3,6-dioxa-1,8-octanedithiol (DODT) by rotating the mixture at room temperature for 2 hours on a mechanical rotator. The solutions are filtered to remove resin and precipitated into ice-cold diethyl ether. Precipitated peptides are collected via centrifugation (4000 rpm for 10 minutes), washed thrice with diethyl ether, and dried under vacuum overnight.

After cleavage and precipitation, correct synthesis and functionalization are validated using matrix assisted laser desorption/ionization time of flight (MALD-TOF) with α-cyano-4-hydroxycinnamic acid (CHCA) as the matrix. CHCA is dissolved in MALDI solvent (1:1 acetonitrile: ddH$_2$O with 0.1% TFA) at 10 mg mL$^{-1}$ and combined 1:1 with 1 mM peptides dissolved in MALDI solvent. Samples are spotted at 1 µL per spot on a MSP 96 target ground steel plate, dried, respotted, and dried before analysis. Calibration is performed using aliquotted peptide calibration standards spotted once at 1 µL per spot. MALDI identifies complete and successful functionalization of TBP and SCP (FIG. 14).

Peptide-Functionalized Poly(Ethylene Glycol) Copolymers Synthesis

Reversible addition-fragmentation chain transfer (RAFT) polymerization is used to synthesize peptide-functionalized PEG-based copolymers. Methacrylamide-functionalized TBP or SCP are combined with PEG methyl ether methacrylate (300 Da) at a 50 wt % monomer concentration in N,N-dimethylformamide (DMF) in an 8-mL septa-sealed reaction vessel. Peptide monomer and BIO-releasing monomer feed is varied. 4-cyano-4-(ethyl sulfanylthiocarbonyl) sulfanyl pentanoic acid (ECT, synthesized as previously described in Moad et al., 2005, Polymer 46:8458) and azobisisobutyronitrile (AIBN, Sigma Aldrich, recrystallized in methanol) are added as the RAFT chain transfer agent (CTA) and initiator, respectively, with a monomer:CTA: initiator ratio of 150:1:0.1. Alternatively, peptide-conjugated ECT is used as the CTA. Vials are purged with nitrogen for 15 minutes and placed in a 60° C. oil bath for 24 hours. Reactions are then opened to atmosphere, precipitated in 70:30 pentane:diethyl ether, and collected via centrifugation (1500 rpm for 10 minutes). Polymers (FIG. 15) are dissolved in acetone and reprecipitated thrice, then dried under vacuum. A sample of polymer is characterized with gel permeation chromatography (GPC) for molecular weight and polydispersity using a TSK gel super HM-N column and a mobile phase of 0.05 M lithium chloride (LiCl) in DMF at a flow rate of 0.35 mL min$^{-1}$. Samples are dissolved in DMF with 0.05 M LiCl at 5 mg mL$^{-1}$, filtered with PTFE 0.2 µm syringe filters before injection, and analyzed using a refractive index detector. Molecular weights are calculated using a light scattering detector and a do dc$^{-1}$ value determined through prior experimentation. Unreacted monomer is removed by dissolving polymers in distilled deionized water (ddH$_2$O) and dialyzing against ddH$_2$O (6-8 kg/mol cutoff) overnight. Polymers are lyophilized, then characterized with absorbance spectrophotometry for peptide incorporation (Stoscheck, 1990, Methods in Enzymology 182:50; Anthis and Clore, 2013, Protein Sci 22:851). Polymers are dissolved in ddH$_2$O at a concentration of 3 mg mL$^{-1}$ (~100 µM) and measured for absorbance at 280 nm, where there is a peak in absorbance due to the tyrosine ring (FIG. 16). Concentration of peptide is calculated using an extinction coefficient of 1490 $M^{-1}$ $cm^{-1}$ and compared to the overall concentration of polymer to determine the mol % peptide incorporation (p).

Converting peptide directly into a polymerizable moiety has both advantages and disadvantages as discussed by Johnson et al, though their use of a linker between the peptide and either the methacrylamide or acrylamide group reduces the effects of sterics (Johnson et al., 2010, Biomacromolecules, 11(11): 3007-13). Advantages include the ability to easily tune the amount of peptide incorporated into polymers, instead of limited to only one peptide per polymer, and decrease the effects on the polymerization process due to changing one of the side groups of the CTA. Furthermore the introduction of a polymerizable methacrylamide group into the peptide eliminates the need for complicated chemistry steps that allow for conjugation to the CTA agent or post-polymerization attachment. As monomers, the peptides can be randomly dispersed throughout the entire polymer or can be constrained to certain section through the creation of block polymers, resulting in two or more distinct sections (Ten Cate et al., 2007, Macromol Chem Physic, 208(13): 1437-46).

Peptide-functionalized Polymer Therapeutics Bone Targeting Studies

Bovine cortical bone is cut into 5-mm square, 0.5-mm thick wafers using a low speed saw with a diamond wafering blade. Bone wafers are boiled in $ddH_2O$ for 15 minutes, placed in 96-well plates, sterilized in 70% ethanol for half an hour on each side, washed thrice in 1×PBS, and incubated in alpha minimum essential medium (α-MEM) for at least 1 hour at 37° C. before cell seeding.

Monocytes are freshly isolated from the spleens of mice, filtered twice with a 40 μm cell strainer, collected via centrifugation (5 minutes, 1000 rpm), and re-suspended in sterile filtered mouse red blood cell lysis buffer for 10 minutes at room temperature. After neutralizing lysis buffer with 1×PBS, monocytes are collected via centrifugation and washed in α-MEM containing 10% fetal bovine serum, 1% penicillin-streptomycin-fungizone, 1% GlutaMAX, and 1% non-essential amino acids before re-suspension in medium containing 100 ng $mL^{-1}$ M-CSF conditioned medium (Takeshita et al., 2000, J Bone Miner Res 15:1477). Monocytes are seeded in 96-well plates on the tissue culture surface or on prepared bovine cortical bone wafers at $2 \times 10^5$ cells $well^{-1}$ ($1 \times 10^6$ cells $mL^{-1}$). After 3 days of incubation at 37° C. and 5% $CO_2$, medium is supplemented with 1 ng $mL^{-1}$ receptor activator of nuclear factor κB ligand (RANKL) to induce osteoclast differentiation. Osteoclast differentiation is confirmed via TRAP staining (FIG. 17) and resorption pit formation (FIG. 18, Table 3) after 10 days.

The method of inducing osteoclastogenesis via M-CSF and RANKL, discussed herein, is effective for both spleen-derived monocytes and bone marrow cells, as evidenced by positive TRAP staining (FIG. 17) and resorption pit excavation (FIG. 18, Table 3). This is a well-established method (Shevde et al., 2000, Proc Natl Acad Sci, 97(14): 7829-7834; Galvin et al., 1999, Biochem Bioph Res Co, 265; 233-239) and contrasts the use of other factors, such as parathyroid hormone, that influence osteoclastogenesis by acting on osteoblastic stromal cells rather than the osteoclast precursor cells themselves (Fuller et al., 1998, J Endorcrinol, 158: 341-350; Nishikawa et al., 1998, J Bone Miner Res, 13(6): 986-995). This enables a simple means for generating resorption pits without the need for a defined co-culture system. It is necessary to establish a uniform platform to interpret without bias the binding of peptide-functionalized polymer therapeutics to TRAP deposited by osteoclasts, and uniformity is determined by quantifying TRAP and resorption pit area. While another group developed a more thorough method to characterize resorption pits by measuring pit depth (Walsh et al, 1991, J Bone Miner Res, 6(7): 661-671), in this work it is only necessary to quantify TRAP deposition. After 10 days of osteoclast precursor culture, differentiated osteoclasts consistently modify half the area of bone wafers with TRAP and begin to excavate resorption pits (FIG. 18, Table 3).

Peptide-functionalized polymer therapeutics are fluorescently labeled, as in Example 2. In contrast to PEG alone (FIG. 19A), TBP-functionalized polymer therapeutics localize to resorption pits excavated by osteoclasts, evidenced by overlapping fluorescent signal and dark stain (FIG. 19B). No affinity for untreated bone is seen for either PEG (FIG. 19C) or TBP-functionalized polymer therapeutics (FIG. 19D). Notably, accumulation of TBP-functionalized polymer therapeutics is achieved without blocking non-specific binding, indicating high affinity and specificity for TRAP.

Biological Effects of Released Anabolic Agent (BIO)

The chemistry employed to functionalize the chain transfer agent with peptide to form polymers with bone-homing capabilities is well-established. However, in instances where the described functionalization results in less than 80% conjugated CTA, alternative conjugation chemistries including chain-extension methods, thiol-maleimide conjugations, and/or 'click' chemistries may be (Henry et al., 2009, Bioconjugate Chem 20(6):1122-8) employed. The data presented herein indicates the TRAP-binding peptides selected herein efficiently home to bone resorption sites (FIG. 3A through FIG. 3D). However, in instances where TRAP-binding peptides do not result in successful bone homing, any of a multitude of other known peptide and small molecule drugs that home to osseous tissues, including phosphate functionalities and cationic peptides may be used (Nuttelman et al., 2006, Biomaterials 27(8):1377-86; Nuttelman et al., 2006, J Biomed Mater Res A 76(1):183-95;

TABLE 3

TRAP/toludine blue-stained bone wafers were quantified for TRAP and resorption pit area. Numbers are reported as mean ± standard deviation. Statistics were based on One-Way ANOVA with α = 0.05, n = 3.

| | Bone Marrow | | Spleen | | |
| --- | --- | --- | --- | --- | --- |
| | Cell-Laden | Scraped | Cell-Laden | Scraped | P-Value |
| TRAP Area (%) | 45.4 ± 3.9 | 50.1 ± 14.0 | 46.2 ± 4.7 | 53.0 ± 9.0 | 0.6694 |
| Pit Area (%) | 18.8 ± 6.5 | 4.4 ± 1.9 | 10.7 ± 6.6 | 12.3 ± 4.8 | 0.0965 |

Segvich et al., 2009, Biomaterials 30(7):1287-98; Weiger et al., 2010, Biomaterials 31(11):2955-63).

The biological activity of the released BIO is tested by measuring its effect on osteoblasts in culture. These experiments define the delivery parameters (drug release rate, concentration, and longevity of drug release) for further studies to rescue osteoblast function and bone production.

Osteoclast pits are prepared and treated with peptide-homing BIO delivery systems. Osteoblasts, isolated from neonatal mice calvaria, are then added to the pits, and overall enhancement of bone formation through drug delivery is assessed using Orange G staining method and histology to distinguish old and new bone area to assess the overall enhancement of bone formation rate by controlled BIO delivery. Gene expression by the osteoblasts is also analyzed to ensure the efficacy of BIO delivery to enhance β-catenin, alkaline phosphatase, osteocalcin, and Runx2 and enabling selection of appropriate polymer therapeutics that result in similar levels of these bone-associated factors to normal osteoblasts. By varying the kinetics of BIO release, concentration of BIO, and longevity of release (up to two weeks, as shown in FIG. 11), different quantitative amounts/rates of bone formation are obtained, and quality of bone produced is assessed.

Several BIO-releasing polymers that are the correct molecular weight to enhance circulation time and avoid renal clearance have been successfully synthesized. Further, these polymers exhibit different release kinetics and doses of BIO in order to match bone formation requirements. Finally, released BIO biological activity is confirmed versus the free, unconjugated molecule and rescue of β-catenin signaling in osteoblasts is verified. As shown in FIG. 33, lead treatment suppresses β-catenin and osteogenic gene expression after 10 days, and is therefore a good model for osteoporotic-like bone disease. FIG. 20 demonstrates the biological activity of BIO, showing that BIO treatment increases β-catenin (black) levels and ALP production (white).

Homing and Efficacy of Peptide-targeted Polymer Therapeutics In Vitro.

Peptides that specifically home to bone resorption pits have recently been identified (Sheu et al., 2002, J Bone Miner Res 17(5):915-22). Specifically, the peptide TPLSYLKGLVTV (SEQ ID NO: 3) binds with high affinity (subnanomolar Kd) to the molecule type V tartrate resistant acid phosphatase (TRAP) that is left by osteoclasts during resorption phase of bone remodeling. To take advantage of this peptide to home BIO to bone resorption pits, the end functional nature of the RAFT polymers developed above are utilized. First, the RAFT agent R-group is functionalized (CTA, see FIG. 10A through FIG. 10D) to enable facile conjugation of the amino terminus of the peptide (Benoit et al., 2011, Biomacromolecules 12(7):2708-14; Duvall et al., 2010, Mol Pharmaceut 7(2):468-76). The peptide-RAFT agent is purified and characterized (column chromatography, NMR, Mass Spectrometry) and utilized to synthesize polymers to release the right concentrations of BIO with kinetics leading to rescue of bone production capacity by lead treated osteoblasts and appropriate circulation times. Polymer conjugates are also prepared including a small amount of fluorescent monomer to enable visualization via confocal microscopy (see FIG. 3A through FIG. 3D) and resorption-site-targeted BIO release is assessed for enhancing bone production by osteoblasts.

Polymers were synthesized with increasing amounts of TRAP binding peptide (TBP). After polymers were purified final peptide incorporation was evaluated through the absorption spectra of the polymers, specifically at 280 nm (FIG. 34).

A polymerization with a PEGMMA:TBP ratio of 95:5 was carried out over the course of 24 hours, with multiple time points being taken and analyzed via GPC to determine the linearity and thus control of the polymerization process (FIG. 35).

In Vivo Evaluation of Successful Osteoporotic Bone Homing of Polymer Therapeutics.

Successful bone homing is first evaluated using both normal and lead-induced models of osteoporosis. To achieve this, experiments were designed using a combination of microCT-detectable polymers (detectable through incorporation of iodine monomers) (Jayakrishnan and Thanoo, 1992, J Appl Polym Sci 44(4):743-8), fluorescent polymer), and the tritiated polymers. First, osteoporosis is induced using lead treatments as described elsewhere herein. Although this is a well-established model (Carmouche et al., 2005, Environ Health Perspect 113(6):749-55; Hicks et al., 1996, Toxicol Appl Pharmacol 140(1):164-72), initiation of osteoporosis is verified through typical analysis of bone volume and quality, as shown in FIG. 36A through FIG. 36B. Briefly, after induction of osteoporosis using 50 ppm Pb in drinking water, a dose that results in blood lead levels comparable to humans suffering from lead toxicity (Cory-Slechta et al., 2010, Toxicol Sci 117(2):427-38), the middle trabecular region of the third lumbar vertebrae (FIG. 36A), the distal trabecular femur region (FIG. 36B) and proximal trabecular tibia region (FIG. 36C) of rats were analyzed for bone properties using microCT. Significant reductions in bone volume normalized to total volume (BV/TV) and trabecular number (1/mm) were observed in Pb-treated groups and these trends are similar to that observed with other animal models of osteoporosis (e.g., ovariectomized mice). Once osteoporosis is verified similarly, mice are treated (tail vein injections) with TRAP-homing and control peptide-modified BIO delivery systems and the accumulation of polymer in both control and lead-induced osteoporotic mice is longitudinally (over 5 days) evaluated. The pharmacokinetics is verified as described elsewhere herein, paying particular attention to any changes due to targeting. Moreover, 24 hours after injection, mice are sacrificed and microCT and scintillography performed on isolated bones to assess the relative accumulation of polymer therapeutic within bone. In addition, histology is used (using the fluorescent polymers) to verify colocalization of polymer accumulation at sites of TRAP staining (e.g., osteoclast resorption pits).

Example 5

Peptide-Functionalized Therapeutics for Targeted Drug Delivery to Actively Remodeling Bone Administering bone anabolic therapeutic agents to mice systemically poses the risk of off-target effects. Although the invention described herein is targeted to bone in need of formation (i.e., to resorption pits), polymer therapeutics will distribute to other tissues. In the present study, a novel tartrate-resistant acid phosphatase (TRAP)-binding peptide (TBP)-based poly(ethylene glycol) (PEG) therapeutic is developed to bind specifically to actively remodeling bone surfaces in a mouse model of osteoporosis. Towards the goal of designing polymer therapeutics with a biodistribution profile that favors accumulation of drugs specifically in actively remodeling bone, polymer molecular weight and targeting moiety are considered.

Peptide-functionalized Poly(Ethylene Glycol) Copolymers Synthesis

Reversible addition-fragmentation chain transfer (RAFT) polymerization is used to synthesize peptide-functionalized PEG-based copolymers. Methacrylamide-functionalized TBP or SCP, synthesized as described in Example 4, are combined with PEG methyl ether methacrylate (300 Da) at a 0.5 M concentration in N,N-dimethylformamide (DMF) in an 8-mL septa-sealed reaction vessel (FIG. 21). Peptide monomer and BIO-releasing monomer feed is varied. 4-cyano-4-(ethylsulfanylthiocarbonyl) sulfanyl pentanoic acid (ECT, synthesized as previously described in Moad et al., 2005, Polymer 46:8458) and azobisisobutyronitrile (AIBN, Sigma Aldrich, recrystallized in methanol) are added as the RAFT chain transfer agent (CTA) and initiator, respectively, with a monomer:CTA:initiator ratio indicated in Table 4. Vials are purged with nitrogen for 15 minutes and placed in a 60° C. oil bath for 24 hours. Reactions are then opened to atmosphere, precipitated in 70:30 pentane:diethyl ether, and collected via centrifugation (1500 rpm for 10 minutes). Polymers (FIG. 15) are dissolved in acetone and reprecipitated thrice, then dried under vacuum. A sample of polymer is characterized with gel permeation chromatography (GPC) for molecular weight and polydispersity using a TSK gel super HM-N column and a mobile phase of 0.05 M lithium chloride (LiCl) in DMF at a flow rate of 0.35 mL min$^{-1}$. Samples are dissolved in DMF with 0.05 M LiCl at 5 mg mL$^{-1}$, filtered with PTFE 0.2 µm syringe filters before injection, and analyzed using a refractive index detector. Molecular weights are calculated using a light scattering detector and a do dc$^{-1}$ value determined through prior experimentation. Unreacted monomer is removed by dissolving polymers in distilled deionized water (ddH$_2$O) and dialyzing against ddH$_2$O (6-8 kg/mol cutoff) overnight. Polymers are lyophilized, then characterized with absorbance spectrophotometry for peptide incorporation (Stoscheck, 1990, Methods in Enzymology 182:50; Anthis and Clore, 2013, Protein Sci 22:851). Polymers are dissolved in ddH$_2$O at a concentration of 3 mg mL$^{-1}$ (~100 µM) and measured for absorbance at 280 nm, where there is a peak in absorbance due to the tyrosine ring (FIG. 16). Concentration of peptide is calculated using an extinction coefficient of 1490 M$^{-1}$ cm$^{-1}$ and compared to the overall concentration of polymer to determine the mol % peptide incorporation (p).

Measurement of Peptide-functionalized Polymer Affinity for TRAP Protein

Surface plasmon resonance (SPR) is used to assess the affinity of peptide-functionalized polymers for TRAP. Series S Sensor CM5 Chips are functionalized with TRAP via 1-ethyl-3-(3-dimethylaminopropyl) carbodiimide (EDC)/N-hydroxysuccinimide (NHS) chemistry. Briefly, the chips, which have a carboxymethylated dextran functionality, are activated through the introduction of NHS and EDC. After activation, TRAP protein, at 30 µg/mL in sodium acetate (pH=5), is introduced to the surface. Ethanolamine-hydrochloric acid is used to quench unreacted carboxysuccinimide groups. Polymers are dissolved in running buffer of PBS with 0.005% Tween20. Polymers are analyzed in duplicate at different concentrations. Surface regeneration is achieved using 1-10 mM NaOH solutions as necessary. An unfunctionalized surface is used as a reference to eliminate signal due to nonspecific binding. Sensorgram data (FIG. 22) are exported from the SPR evaluation software after smoothing data of injection events and analyzed. Response units (RU) are converted into concentrations for rate analysis using the equation:

$$S_{[M]} = RU/60000 \, MW$$

Where S is the concentration of polymer bound to the TRAP-functionalized surface and MW is the molecular weight of the polymer. The binding rates of polymers to TRAP are determined in the initial linear portion of association, within two seconds of the start of injection. The reciprocals of binding rates are plotted against the reciprocals of polymer concentrations to obtain a linear relationship, generalized in the equation:

$$V_i^{-1} = K_D S_i^{-1} V_m^{-1} V_m^{-1}$$

Where $V_i$ is the binding rate for each i concentration of polymer and $V_m$ is the maximum binding rate of polymer to TRAP. This relationship identifies the $K_D$ for each polymer (Table 4). Only TBP-functionalized polymers show affinity for TRAP (FIG. 22), as control (SCP-functionalized and PEG) polymer show no positive binding response (FIG. 23A through FIG. 23C).

TABLE 4

| Peptide Feed | M:CTA:I$^{a)}$ | p (# per chain)$^{b)}$ | $M_n^{c)}$ [kDa] | PDI$^{c)}$ | $K_D^{d)}$ [µM] |
|---|---|---|---|---|---|
| 0% TBP$^{e)}$ | 100:1:0.1 | 0% (0) | 42.0 | 1.1 | ND$^{f)}$ |
| 5% TBP | 125:1:0.1 | 7% (3) | 17.1 | 1.1 | 70 |
| 5% TBP | 250:1:0.1 | 4% (5) | 42.3 | 1.1 | 80 |
| 5% TBP | 600:1:0.1 | 4% (11) | 98.2 | 1.1 | 140 |
| 10% TBP$^{e)}$ | 300:1:0.1 | 9% (9) | 40.1 | 1.1 | 60 |
| 20% TBP | 500:1:0.1 | 19% (12) | 32.7 | 1.1 | 70 |
| 10% SCP$^{e)}$ | 500:1:0.1 | 9% (10) | 44.7 | 1.1 | ND |
| 20% SCP | 500:1:0.1 | 19% (9) | 24.3 | 1.1 | ND |

$^{a)}$The ratio of monomer (M), chain transfer agent (CTA), and initiator (I) was modified to achieve a desired molecular weight.
$^{b)}$The peptide incorporation (p) into polymers was calculated from UV-vis spectra.
$^{c)}$Molecular weight ($M_n$) and polydispersity index (PDI) were determined through gel permeation chromatography (GPC).
$^{d)}$Dissociation constant ($K_D$) was calculated from initial rate analysis of surface plasmon resonance (SPR) sensorgrams.
$^{e)}$Unfunctionalized polymer (PEG), 10% TBP-functionalized polymer (pTBP), and 10% SCP-functionalized polymer (pSCP) were used for in vitro and in vivo bone-targeting studies.
$^{f)}$Not detectable.

Assessment of Cytocompatibility of Peptide-functionalized Copolymers

Mesenchymal stem cells (MSCs) are treated with medium alone or with medium supplemented with TBP, SCP, PEG, TBP-functionalized PEG polymer (pTBP), or SCP-functionalized PEG polymer (pSCP), as indicated in Table 4, at concentrations of 0.1, 0.5, 1.0, 5.0, and 10.0 µM. A solution of 1% Triton X-100 is used as a negative control. After 24 hours of treatment, media are removed and replaced with 10% alamarBlue solution in MSC maintenance medium, and MSCs are returned to the incubator for 4 hours. In triplicate, a 100-µL sample of medium is taken from each well and added to a black well plate. Relative metabolic activity is assessed by measuring fluorescent signal (excitation=545 nm, emission=590 nm) of samples and subtracting fluorescent signal of alamarBlue solution, then normalizing to untreated MSCs.

Osteoclasts are treated similarly with peptides and polymers following 14 days of differentiation in a tissue-culture plastic 96-well plate. Osteoclasts are TRAP-stained, and the entire well is imaged using light microscopy. Blinded viable cell counts are obtained for each well, with each normalized to untreated osteoclasts. Regardless of dose, no statistically significant differences are detected among treatments or between any treatment and untreated cells for osteoclasts (FIG. 24). A small but significant difference is detected among treatments for MSCs (FIG. 24). All treatments for both cell types resulted in greater than 70% cell viability, the accepted value for cytotoxicity of biomaterials (I. O. f Standardization, in Tests for in vitro cytotoxicity, Switzerland 2009, 42).

Co-localization of Polymers to Actively Remodeling Bone In Vivo

A thinned-skull cranial window is produced in mice as previously described (Yang et al., 2010, Nat Protoc 5:201). Briefly, a 500-μm diameter defect is made in the skull of mice and covered with a glass coverslip. The night before imaging, mice are injected intraperitoneal with 100 μL reconstituted cathepsin K probe in 1×PBS, prepared according to the manufacturer's protocol. At times of 3 and 8 days post-procedure, 5 mg kg$^{-1}$ of fluorescently-labeled pTBP, pSCP, or PEG in saline is injected intraperitoneal and imaged thirty minutes later using two-photon microscopy (Olympus Fluoview). Cathepsin K, a cysteine protease, is secreted by osteoclasts; therefore, TRAP is expected to be present in areas with cathepsin K activity. Accumulation of TBP-functionalized polymers colocalize to areas with cathepsin K and osteoclast activity (FIG. 26). Bone drilling defects have been used previously to investigate osteoclast activity, with osteoclast accumulation at the defect evident from positive TRAP staining (Tanaka et al., 2010, J Biomed Mater Res, 93A(2): 469-474). This further suggests that the calvarial edge surrounding the defect in the model contains areas of TRAP deposited by osteoclasts. Longitudinal studies are conducted that ensure TBP-functionalized polymer therapeutics do not interfere with bone deposition, and a secondary imaging channel is used to show TRAP/polymer overlap. Other live imaging modalities and sections of sacrificed mice are used to track biodistribution to other organs. Since the amino acid sequence of human, mouse, and rat TRAP is 89-94% homologous (Lamp and Drexler, 2000, Leukemia Lymphoma, 39(5-6): 477-484), it is probable that TBP-functionalized polymer therapeutic affinity to TRAP in mice can be translated into humans.

Polymer Biodistribution in Ovariectomized Mice

Polymer therapeutics (~10 mg) are dissolved in 10 mL dimethylsulfoxide (DMSO). One drop of N,N-diisopropylethylamine (DIEA) and 330 μL of N-succinimidyl propionate, N-[propionate-2,3-$^3$H(N)] are added with stirring at room temperature. After 3 days, reactions are diluted with ddH$_2$O and dialyzed against ddH$_2$O for 2 days (6-8 kg/mol cutoff). Polymers are collected through lyophilization and then reconstituted at 100 μg μL$^{-1}$ in DMSO. Cold polymers at 100 μg μL$^{-1}$ in DMSO are mixed into the hot polymers to equalize radioactivity across polymers.

Forty mice are anesthetized with intraperitoneal injections of 60 mg kg$^{-1}$ of ketamine and 4 mg kg$^{-1}$ of xylazine, injected subcutaneously with 3.25 mg kg$^{-1}$ of extended release buprenorphine, and ovariectomized (OVX) from a dorsal approach. Eight additional mice serve as controls. Eight weeks after OVX, bone mineral density is assessed via dual-energy X-ray absorptiometry (DXA).

Mice are injected with 50 mg kg$^{-1}$ (~10$^6$) of radiolabeled polymer diluted in saline, or with saline vehicle. After 24, 48, 72, 96, and 120 hours, the brain, lungs, liver, spleen, intestines, kidneys, heart, femurs, and tibias of each mouse are harvested, rinsed in saline, and weighed. Bone tissue is minced with scissors and incubated in 300 μL each of 70% perchloric acid (J. T. Baker) and 70% nitric acid (Macron) and 2.4 mL of hydrogen peroxide (H$_2$O$_2$) per 200 mg of tissue in a 60° C. oven for 1.5 hours. Samples are then removed, and 600 μL of 200 mM ethylenediaminetetraacetic acid (EDTA, J. T. Baker) are added per 200 mg of tissue before incubation overnight at room temperature. A 180-μL sample is added to a scintillation vial along with 180 μL of ddH$_2$O and 10 mL of scintillation cocktail fluid and lightly shaken to mix. Soft tissue is processed as previously described (Crownover et al., J Control Release 155:167). Soft tissue is minced with scissors and homogenized in 10 mL of ddH$_2$O per 1 g of tissue, and 200 μL of homogenate are combined with 500 μL of Solvable in a scintillation vial. Samples are incubated in a 60° C. oven for 2 hours until completely dissolved. After removing samples, 50 μL of 200 mM EDTA and 200 μL of 30% H$_2$O$_2$ are added and allowed to incubate overnight at room temperature. After incubation, 25 μL of 10 N hydrochloric acid and 10 mL of scintillation cocktail fluid are added, and samples are lightly shaken to mix. All samples are allowed to light-adapt for at least twelve hours before counting in an liquid scintillation counter to calculate % injected dose of polymer per gram of tissue. Significantly more TBP-functionalized polymer accumulates in the hind limbs than control polymers, indicating targeting is specific to TBP (FIG. 27). In addition, histology is used (using fluorescently labeled polymers rather than tritiated polymers) to verify colocalization of polymer accumulation at sites of TRAP staining (e.g., osteoclast resorption pits) at 24 hours.

Verification of Enhanced Pharmacokinetics of BIO Polymer Therapeutic Versus Free BIO Enhanced pharmacokinetics is verified. PEG monomers are tritiated as described (Diamond et al., 1986, European Polymer Journal 22(8):601-9) and incorporated into a subset of BIO-containing polymers. Similarly, BIO alone is tritiated. The pharmacokinetics of the various tritium-labeled polymers and free BIO are evaluated by administering tail vein injections in mice (C57Bl/6). The aim of these studies is to examine whether the polymer conjugates enhance circulation time of BIO. At 2 min, 15 min, 30 min, 60 min, 240 min, and 1440 min, n=10 blood samples are isolated in each test group and tested. Scintillation counter data are used to calculate the % injected dose per gram of each blood sample. Pharmacokinetic parameters are determined based on noncompartmental models (Berezhkovskiy, 2011, J Pharm Sci 100(6):2482-97; Looby and Weiss, 1995, J Pharmacokinet Biopharm 23(6):635-49; Wilson et al., 1985, Am J Vet Res 46(6):1316-8). Moreover, 24 h after injection (1440 min), mice are sacrificed and scintillography performed on isolated organs and bones to assess the relative accumulation of polymer therapeutic within bone. Mice receiving vehicle only (PBS or corn oil, as BIO is poorly soluble in aqueous solution) injections serve as controls for background tissue autofluorescence and radiation.

Many of the studies supporting PEG's enhancement of circulation time utilize linear PEG molecules of about 24 kDa. Here, monomers of PEG (repeat units of 8) were utilized and polymerized into 'brush' architectures. Thus, it is aimed to enhance circulation time of BIO from the expected value of <2 min to >1 hour, which is typical for PEGylated pharmaceuticals (Lipton et al., 2007, Leuk Lymphoma 48(3):497-505; Talpaz et al., 2005, Clin Cancer Res 11(17):6247-55; Zeuzem et al., 2004, Gastroenterology 127 (6):1724-32). The molecular weight dependence of circulation time for this architecture of PEG polymers is examined. It is observed that BIO affects β-catenin signaling within osteoblasts, rescuing their bone producing capacities. However, in certain situations BIO delivery may not be potent enough to rescue the phenotype completely. In that case, other osteogenic signals can be incorporated into the polymer therapeutic. These include steroids such as dexamethasone or statins such as fluvastatin, both of which have been shown to enhance bone production by osteogenic cells (Benoit et al., 2007, Adv Funct Mater 17(13):2085-93;

Benoit et al., 2006, Biomaterials 27(36):6102-10; Nuttelman et al., 2006, Biomaterials 27(8):1377-86; Nuttelman et al., 2006, J Biomed Mater Res A 76(1):183-95).

Assessing Efficacy of Developed Bone Therapeutic

Both normal and osteoporotic mice are treated with the peptide-homing BIO and its effects long-term are assessed. Peptide-homing BIO and free BIO (as a control) are injected via tail vein at two normalized BIO doses (1 and 20 mg/kg, (Curry, 2004, Invest New Drugs 22(3):299-305)) using the following dosing regimes: 1×, 1×/day for 7 days, and 1×/day for 14 days. Overall bone mineral density increases and/or visualization of enhanced bone formation (DXA, microCT, histology of dynamic parameters of bone formation through injections of calcein (4 mg/kg) and xylenol orange (100 mg/kg) 4 and 2 days before sacrifice, respectively) are performed 14 days following the initiation of treatment which provide evidence of enhanced bone formation. Six and 9 weeks after treatments are administered, biomechanics are assessed to compare treated, osteoporotic animals to untreated control animals and untreated osteoporotic animals. Briefly, the ends of the femurs isolated from animals are cemented into a custom jig using PMMA to ensure axial alignment. Specimens are bathed in PBS at room temperature for at least 2 hours after potting to allow for rehydration of the tissue and hardening of the PMMA. Specimens are mounted on an EnduraTec TestBench™ system (200 N.mm torque cell; Bose Corporation, Minnetonka, Minn.) and tested in torsion until failure (Brodt et al., 1999). The torque data is plotted against the rotational deformation to determine the Ultimate Torque (TUlt), yield torque, torsional rigidity and fracture energy. After testing to failure, samples are X-rayed to examine failure modes (Reynolds et al., 2007, J Biomech 40(14):3178-86). The presence of adverse systemic side effects (e.g., assessment of safety and efficacy) of administration is evaluated by examining liver toxicity through analysis of blood serum liver enzymes aspartate aminotransferase (AST) and alanine aminotransferase (ALT). Rats are employed as a second animal model to ensure efficacy across species.

The experiments detailed herein obtain the required preclinical evidence of the enhancement of bone formation by targeted, BIO-releasing polymer therapeutics within the context of OVX-induced osteoporosis.

In instances where TRAP-binding peptides do result in successful bone homing in vivo, any of a multitude of other known peptide and small molecule drugs that home to osseous tissues, including phosphate functionalities and cationic peptides may be utilized (Nuttelman et al., 2006, Biomaterials 27(8):1377-86; Nuttelman et al., 2006, J Biomed Mater Res A 76(1):183-95; Segvich et al., 2009, Biomaterials 30(7):1287-98; Weiger et al., 2010, Biomaterials 31(11):2955-63). In instances where the overall enhancement of bone production is less than desired, the overall dose may be increased or the therapeutic delivery window is increased to enhance BIO's effects on bone formation. Moreover, the approach may be enhanced using drug delivery systems designed to reduce osteoclast resorption (e.g., bisphosphonates) as the intended targets are different. Thus, significant advantages may be reaped using both therapies at once.

Experimental Details of Statistics:

Three statistical tests are utilized during the analysis of these experiments: the two sample, two-way t-test and the one- and two-way ANOVA. As these tests require that the data be normally distributed, data is first tested for normality using the D'Agostino and Pearson omnibus test for normality. The data is then tested for homoscedasticity (equality of variance) using Levene's test (if the data is normally distributed) or Levene's Improved test (if the data is not normally distributed), to determine if homoscedasticity can be assumed in subsequent testing. Finally, difference in mean values between experimental groups is assessed using either the two-way t-test (unless the data is non-normal, in which case the nonparametric Mann-Whitney U test is used), or the one- or two-way ANOVA (unless the data is non-normal in which case the nonparametric Kruskal-Wallis test is used). Should ANOVA testing show that there is significant difference between groups, post-hoc testing is performed to identify between which groups the difference originates. If all pair-wise comparisons must be performed to identify the source of significance, Tukey's HSD post-hoc test is used; if, however, only select comparisons need to be performed, the Bonferroni-Dunn post-hoc test is used, unless comparisons are pre-planned, then the Dunnett post-hoc test is used.

Example 6

Phosphate and Acidic Amino Acid-mimetics Bone Homing

Bisphosphonates and phosphonate-mimetics (e.g., phosphates) and peptides typically bearing multiple acidic groups (e.g., poly(Asp)) show great promise for drug targeting to bone. These functionalities can target bone (phosphate) or more specifically target bone resorption surfaces (acidic amino acids), respectively, where incorporation of multiple targeting moieties or multivalency results in far superior targeting efficiency. While introduction of singular targeting groups is a significant challenge, as conjugation chemistries between drug and targeting modality must be compatible and not reduce drug efficacy, synthesis of multifunctional phosphonates and polypeptides presents an even greater obstacle, with time-consuming synthesis generating low yields and irreproducible results. Thus, the experiments presented herein utilize phosphate- and acidic amino acid-mimicking monomers to synthesize multivalent, highly controlled polymer architectures that home to bone with high affinity. These polymer-targeting modalities (FIG. 28A and FIG. 28B) are synthesized using reversible-addition chain transfer (RAFT) polymerization to allow for reproducible, easy, and scalable syntheses. Data presented herein supports controlled synthesis of multivalent phosphates and peptides that result in high affinity to bone and simple and reproducible incorporation and controlled release of small molecule drugs from similarly-structured polymers have been previously described (Benoit et al., 2007, Adv Funct Mater, 17(13): 2085-93; Benoit et al., 2009, J Control Release, 133(3): 221-9; Benoit et al., 2006, Biomaterials, 27(36): 6102-10; Duvall et al., 2010, Mol Pharm., 7(2): 468-76). The experiments presented herein examine whether polymers that include phosphate or acidic amino acid-mimetics can be reproducibly and simply synthesized to provide bone-homing capabilities in vivo to drugs.

Various attempts to target drugs to the skeleton can be categorized into phosphate-based and peptide approaches. Bisphosphonate conjugates demonstrate excellent bone targeting in vivo (Franc et al., 2009, Eur J Org Chem, 25: 2490-9; Ross and Roeder, 2011, J Biomed Mater Res A, 99(1): 58-66). For example, bisphosphonate-conjugated osteoprotegrin (OPG) resulted in 100% greater bone accumulation versus untargeted OPG (Doschak et al., 2009, 6(2): 637-40). Interestingly, though, no bone accumulation differences in vivo were observed between bisphosphonate-functionalized fetuin (a model protein) and native fetuin. Only when fetuin was modified with multivalent bisphosphonates, specifically those that present two additional phosphates, was successful bone targeting observed in vivo (Gittens et al., 2005, Mol Pharm., 2(5): 392-406). Acidic peptides that mimic the strong affinity of osteopontin (bone sialoprotein) to bone have also been demonstrated to have excellent targeting in vivo (Sekido et al., 2001, 9(2): 111-21). Similar to phosphonates, Ouyang et al. demonstrated that multiple acidic peptide sequences are required for bone binding: two chains of $Asp_6$ doubled bone-binding affinity of polymers versus one peptide chain (Ouyang et al., 2009, Lett Org Chem., 6(4): 272-7).

The studies described herein develop a platform technology based on RAFT polymerizations to overcome synthetic hurdles currently precluding development of multivalent phosphate/acidic amino acid bone-homing therapeutics. Specific bone homing using the simple approach described herein has not previously been demonstrated. The approach described herein utilizes phosphate and acidic amino acid monomers that are synthesized and utilized to make polymers that will further benefit from EPR for successful bone homing. Several groups have successfully demonstrated bisphosphonate- or peptide-mediated homing of small molecule and macromolecular drugs. However, it is clear that multivalent targeting groups enhance bone accumulation, especially as carriers become larger, as in polymer therapeutics (Gittens et al., 2005, Mol Pharm., 2(5): 392-406; Ouyang et al., 2009, Lett Org Chem., 6(4): 272-7; Low and Kopeck, 2012, Adv, Drug Deliv Rev., 64(12): 1189-204), to ensure at least one targeting group is exposed to specifically interact with the bone surface. Current synthesis of multifunctional phosphonates and polypeptides is challenging, with low yields and time-consuming, irreproducible results. Moreover, conjugation between drug and targeting moieties are difficult as they must be compatible and not disrupt drug efficacy. The approach exploits synthetically simple, biocompatible monomers that present phosphates or acidic amino acids identified above to create novel, multivalent bone-targeting polymers. These polymers are synthesized via RAFT polymerization, a technique that results in polymers with highly controlled molecular weights and architectures, low polydispersity/variability, and that can easily be scaled up for preclinical and clinical use. Bone homing is demonstrated based on specificity of targeting moiety employed (phosphate and acidic amino acid monomers). These polymers are readily adaptable for incorporation and release of large repertoires of drugs.

Synthesize and Characterize Phosphate- and Acidic Amino Acid-mimicking Bone-homing Polymer Therapeutics.

Phosphate-containing monomers (6-methacryloylxyhexyl dihydrogen phosphate, FIG. 29A) have recently been synthesized. Subsequent RAFT polymerization using this monomer yielded multivalent phosphate-containing oligomers (repeats of ~5-15 of the phosphate monomers, Mw~2-5 kDa, PDI<1.2, FIG. 29A). These oligomers home to bone specifically, as highlighted in FIG. 29B-FIG. 29D. Cortical bone wafers incubated with control polymers (fluorescein-labeled PEG, FIG. 29B) show no evidence of fluorescence using confocal microscopy. However, upon incubation with phosphate polymers that were copolymerized with fluorescein methacrylate, bone wafers have clear, uniform, green fluorescence (FIG. 29C and FIG. 29D) indicating specific bone accumulation. Moreover, cortical bone wafer binding experiments were performed using these same fluorescein-labeled phosphate-functionalized oligomers. The binding isotherm obtained is shown in FIG. 30 along with the calculated disassociation constant of ~80 µM which is well within the range of other successful bone-homing modalities (Low and Kopeck, 2012, Adv, Drug Deliv Rev., 64(12): 1189-204).

Synthesize Multivalent Phosphate-functionalized Polymers.

Experiments are designed to identify important attributes of phosphates that provide bone specificity. Interesting ranges of phosphate functionalization that mediate bone homing have been identified. Poly (ethylene glycol) (PEG)-based polymers are used for these studies. PEG imparts favorable properties to drug-conjugates, as it is hydrophilic and inert and prevents non-specific accumulation of drug in off-target tissues. For PEG, 40 kDa has been shown to provide favorable pharmacokinetic properties (increased blood circulation time and target tissue accumulation) while still allowing for renal excretion of the polymer once it has delivered its drug payload, thus minimizing side effects from the polymer itself (Lipton et al., 2007, Leuk Lymphoma 48(3): 497-505; Reddy et al., 2009, J Viral Hepat, 16(10): 724-31; Talpaz et al., 2005, Clin Cancer Res, 11(17): 6247-55; Zeuzem, 2008, J Hepatol, 49(2): 157-9; Zeuzem et al., 2004, Gastroenterology, 127(6): 1724-32). However, both lower and higher molecular weights of PEG are tested (range 20-60 kDa). The overall % of phosphate functionalities is also modulated to control bone homing. As previously identified, 1.5 wt % alendronate (a bisphosphonate) randomly incorporated into HPMA polymers was found to have the greatest bone affinity compared with 0.5 wt % and 8.5 wt % functionalization (Wang et al., 2006, Mol Pharm, 3(6): 717-25). Thus, a range of 1-8.5 wt % is utilized herein, and, due to the unique attributes of RAFT, phosphates are incorporated as both block and statistical copolymers with PEG (FIG. 28A and FIG. 28B). Specifically, both of these architectures are synthesized of 6-methacryloyloxyhexyl dihydrogen phosphate (1.5-8.5 wt %) and poly(ethylene glycol) monomethyl ether to yield polymers with overall molecular weights of 20-60 kDa (this results in 18 polymers synthesized; 20, 40, 60 kDa each with 1.5, 5, 8.5% functionalization in both block and statistical copolymers, with 3 controls of 20, 40, 60 kDa PEG (0 wt % phosphate)). Small amounts of fluorescein methacrylate is also included to provide a means to image and quantify binding of polymers to cortical bone wafers. Polymers mimic drug-loaded architectures, where some PEG would theoretically include poly (ethylene glycol)-based drug-releasable tethers (FIG. 31A), which have been previously synthesized and characterized for a variety of small molecule drugs (Benoit et al., 2007, Adv Funct Mater, 17(13): 2085-93; Benoit et al., 2006, Biomaterials, 27(36): 6102-10; Nuttelman et al., 2006, J Biomed Mater Res A, 76(1): 783-95). As highlighted in FIG. 31B, a sustained delivery of active fluvastatin is achieved from polymers over ~18 days; the overall dose is controlled by tethered drug concentration, while the release rate is controlled by the chemistry and length of the degradable lactide linker (Benoit et al., 2007, Adv Funct Mater, 17(13): 2085-93; Benoit et al., 2006, Biomaterials, 27(36): 6102-10; Nuttelman et al., 2006, J Biomed Mater Res A, 76(1): 783-95). Phosphate-PEG polymers are verified to have target molecular weight and low polydispersity using gel permeation chromatography and a phosphate quantification assay is used to verify % phosphate incorporation.

Test Bone Binding Characteristics of Multivalent Polymers.

Qualitatively, bone binding of polymers is investigated using confocal microscopy as in FIG. 29A through FIG. 29D. Briefly, phosphate and control (PEG only) polymers are solubilized at 1 mg/ml in PBS and incubated at 37° C. overnight with 0.5 cm×0.5 cm×1 mm human cortical bone wafers. Wafers are washed in PBS and imaged via confocal microscopy. Stacked sections are compressed into 2D images to allow for qualitative analysis as in FIG. 29A through FIG. 29D. Binding affinity is analyzed quantitatively using a binding assay as described previously (Rodan and Fleisch, 1996, J Clin Invest 97(12):2692-6) and utilized to obtain the data shown in FIG. 30. Fluorescent alendronate serves as positive control and negative controls consist of untargeted polymers.

Synthesize and Test Bone-binding Characteristics of Amino-acid-mimetics Functionalized Polymers.

Acidic amino acid-based monomers are synthesized; functionalized polymers are developed from these moieties; and they are tested for their ability to home to bone resorption sites, mimicking osteopontin's repeats of aspartic and glutamic acid. Peptide-mediated targeting of bone resorption sites have been previously explored, identifying a peptide that homes to these sites with subnanomolar affinity (Sheu et al., 2002). Specific homing of rhodamine (red fluorescence)-labeled peptide to pits is demonstrated in FIG. 3A through FIG. 3D using cortical bone wafers. This peptide is examined for in vivo bone homing, as described elsewhere herein. Described herein is the simplified synthesis using amino acid mimetics. Living polymerization of amino acid or peptide monomers has been demonstrated by a number of polymerization techniques including RAFT (Ayers et al., 2005, Biomacromolecules, 6(2): 825-31; Ayers et al., 2003, Macromolecules, 36(16): 8967-73; Fernandez-Trillo et al., 2007, Macromolecules, 40(17): 6094-9; Maynard et al., 2001, J Am Chem Soc, 123(7): 1275-9). Synthetic procedures are adapted to formulate monomers based on aspartic and glutamic acid. Briefly, the amine group of the amino acid is conjugated to methacryloyl chloride, resulting in methacrylated amino acids (glutamic acid or aspartic acid), which are simply incorporated into RAFT polymers. Similar to phosphates, polymers consist of statistical or block copolymers of PEG and amino acid. Block and statistical copolymers of only one variety: 40 kDa, aspartic acid monomers, and 5 wt % aspartic acid (equivalent to 10 Asp repeats) are first examined. Analysis of these polymers is done exactly as described elsewhere herein except the positive control is a traditional peptide based on aspartic acid (10-mer). Polymers formed of methacrylic acid (presenting similar carboxylic acids along backbone) are also included to assess whether amino acids are necessary for recognition/binding to bone. Depending upon the initial outcomes of screening, additional polymers are also synthesized and tested with similar molecular weights, architectures, and % functionalization as described for phosphate-containing polymers.

The experiments presented herein identify phosphate or amino acid polymer compositions that home to bone similar to or better than positive controls through comparisons of disassociation constants ($K_D$). These polymers are used to analyze in vivo biodistribution and accumulation in bone, pharmacokinetics, and biocompatibility.

In instances where poor binding/specificity of these approaches is observed, alternative approaches are utilized. First, poor binding/specificity may be due to steric hindrance precluding binding of the acidic group of the amino acid mimetics to bone. To overcome steric hindrance, a linker may be incorporated between the acidic group and polymerizable methacrylate group (aminohexyl linker). If lack of specificity/binding still persists, it is possible that the peptide bond itself is important for recognition. Thus, peptide-based monomers may be synthesized as in (Johnson et al., 2010) using poly(Asp), poly(Glu), or novel resorption pit-homing peptide sequence (FIG. 21) and incorporate multiple monomers of whole peptides into RAFT polymers. A variety of different polymer architectures (branched or dendrimer) may be used in either phosphate- or acidic amino acid-functionalization approaches to improve specificity/affinity of bone binding.

Characterize Specific Bone Distribution and Pharmacokinetics of Bone-homing Polymer Therapeutics In Vivo.

The experiments presented herein examine whether safe, effective, bone-specific delivery of polymer therapeutics can be achieved in vivo. It is examined whether polymers accumulate either generally in bone tissue (phosphate targeted) or localize in bone resorption sites (acidic amino acid mimics. Thus, a combination of normal mice and osteoporotic mice are used to show preferential accumulations. Typical dosing regimens expected for polymers with drug delivery mechanisms included are implemented and safety of these regimens are analyzed by examining liver function.

Verification of Homing Specificity, Biodistribution, and Pharmacokinetics of Bone-homing Polymer Therapeutics.

Experiments presented herein assess whether the bone-targeting mechanisms enhance bone homing generally, as expected for the phosphate-functionalized polymer therapeutics, or more specifically to resorption surfaces, as expected for the acidic amino acid mimetic functionalized carriers. Biodistribution of bone-targeted polymers is initially evaluated longitudinally using fluorescent polymers. Amino acid- and phosphate-targeted polymers are utilized based on favorable binding properties. Controls consist of polymers that include no homing functionality, alendronate, and poly(Asp) (10-mers). Mice (wildtype and osteoporotic (ovariectomized)) are treated (tail vein injections, 2 mg/100 µl (Pan et al., 2008, Mol Pharm, 5(4): 548-58)) with fluorescent delivery systems and evaluated for accumulation of polymer in both normal (where low accumulation of acidic amino acid and PEG polymers and high accumulation of phosphate polymers is expected) and osteoporotic mice (where low accumulation of PEG polymers, moderate accumulation of phosphate polymers, and accumulation of acidic amino acid polymers localized to bone resorption sites is expected). After 24 hours, bone accumulation is analyzed longitudinally using the Xenogen IVIS 100 imaging system. Briefly, mice are anesthetized with 2.5% isoflurane and polymer fluorescent signals are quantified using living Image software (Xenogen) both before (baseline) and after treatment. Tissue (kidney, liver, lung, spleen, bone) is isolated from animals treated with fluorescent polymers and histology is used to qualitatively evaluate polymer accumulation for all treatments, paying particular attention to osteoporotic bone where colocalization of fluorescent polymer and tartrate resistant acid phosphatase staining, a resorption surface marker, is carefully documented to assess success of polymer targeting strategies.

PEG monomers are tritiated as described (Diamond et al., 1986, European Polymer Journal, 22(8): 601-9) and incorporated into polymers that have promising homing capabilities. Mice are treated with polymer (tail vein injections). At 2 min, 15 min, 30 min, 60 min, 240 min, and 1440 min, n=10 blood samples are isolated in each experimental and control group and tested. Scintillation counter data are utilized to calculate the % injected dose per gram of each blood sample. Pharmacokinetic parameters are determined based on noncompartmental models (Berezhkovskiy, 2011, J Pharm Sci, 100(6): 2482-97; Looby and Weiss, 1995, 23(6): 635-49; Wilson et al., 1985, Am J Vet Res, 46(6): 1316-8). Moreover, 24 h after injection (1440 min), mice are sacrificed and scintillography is performed on isolated organs and bones to assess the relative accumulation of polymer therapeutic within bone. Similar positive and negative controls as above are used and mice receiving vehicle only (PBS) injections serve as controls for background tissue autofluorescence and radiation.

Characterize Biocompatibility of Polymer Therapeutics.

Adverse systemic side effects (e.g., assessment of safety) of administration of polymer therapeutics are tested by examining liver toxicity and overall animal health over several doses of polymer therapeutic. After injection of therapeutic, analysis of blood serum liver enzymes aspartate aminotransferase (AST) and alanine aminotransferase (ALT) are performed at 1 day, 7 days, and 14 days. mice are treated with 'boosters' of polymer therapeutic every two weeks for 6 months and AST and ALT are analyzed at the same time points. Mouse weight and general well-being is also monitored over treatment time. Two weeks was chosen for 'boosters' as it is anticipated that active drug from polymer therapeutics is able to be delivered for ~18 days based on previous data (FIG. 31B). Thus, treatment every two weeks emulates therapeutic delivery of drugs to bone. The experiments presented herein obtain required pre-clinical evidence of the enhancement of bone homing by targeted, polymer therapeutics.

In conditions where the overall enhancement of bone homing may be less than anticipated, it is also possible to increase the overall dose to enhance accumulation of polymer therapeutic or change molecular weights, architectures, or % targeting functionalization of polymers to improve homing.

Example 7

Peptide-functionalized Polymers Exhibit Excellent Colocalization with Osteoclasts and Remodeling Bone A 0.5-mm hole was drilled into the calvaria of a 3-month-old mouse. A glass window was sutured in place on the skull. Three days post-procedure, the mouse was given an intraperitoneal injection of 100 µl of 26.5-nM PEGMEMA-TBP dissolved in sterile saline (0.11 mg total, approximately 5.5 mg/kg) and returned to its cage. After 30 min, the mouse was anesthetized, and the edges of the defect were imaged through the calvarial window using an Olympus Fluoview multiphoton microscope with second harmonic generation at 25× magnification. Images were captured with and without the use of a Kalman filter to reduce the noise from breathing (FIG. 40).

Example 8

Mesenchymal Stem Cells in Non-union Fractures

In looking at the fracture healing mechanism, mesenchymal stem cells (MSCs) play an important and central role. After fracture occurs, MSCs are recruited to fracture sites, proliferate, and differentiate into osteoblasts to produce bone matrix. However, at the non-union fracture sites, MSCs are dysfunctional. As shown in FIG. 42, there is significant reduced osteogenic differentiation in non-union MSCs. Therefore, in order to treat non-union, strategies were developed to target MSC osteogenesis for better fracture healing.

Specifically, a strategy was developed to target the Wnt/β-catenin pathway, which has been shown to be essential for MSC osteogenesis and bone formation. Briefly, in the absence of Wnt signal, β-catenin are phosphorylated and degraded by the multiprotein complex consisting of Axin, Adenomatous Polyposis Coli (APC), and glycogen synthase kinase 3 beta (GSK3β) (FIG. 43A). As a result, Wnt target gene expression is repressed by transcriptional inhibitors. When WNT signaling is activated, GSK3β activity is inhibited. As a result, β-catenin accumulates and is translocated to the MSC nucleus, causing expression of Wnt targeted genes, including osteogenic related genes RUNX2 and COL1. Research showed that there is an increase in inactivated β-catenin at non-union fractures due to overexpression of GSK3β. To rescue Wnt/β-catenin signaling, GSK3β inhibitors can be employed. Here, a specific GSK3β inhibitor XXVII is used as the drug, which is shown to be a potent agonist of β-catenin (FIG. 43B).

However, systemic delivery of the small molecule drug is limited by low water-solubility and fast systemic clearance. To solve these problems, a nanoparticle (NP) delivery system using poly(styrene-alt-maleic anhydride) and poly(styrene) (PSMA-b-PS) was developed, which is highly stable and exhibits high drug loading capacities. The amphiphilic characteristic of the polymers allows hydrophobic drugs to be loaded into NP cores, which results in enhanced water solubility and in vivo half-life (FIG. 44A).

To investigate the intracellular accessibility of this NPs, polymers were labeled with fluorescein isothiocyanate (FITC) fluorophore and incubated with MSCs (FIG. 44B). Potent cellular uptake was observed (FIG. 45). To validate β-catenin agonism of NP delivered GSK3β inhibitor XXVII, cells were treated with free GSK3β inhibitor XXVII and NP delivered GSK3β inhibitor XXVII. The NP treatment showed even better β-catenin activation than free drug over 5 days of treatment (FIG. 45).

However, another potential problem with systemic use of GSK3β inhibitor XXVII for fracture healing is the generalized expression of the GSK3β enzyme and its versatile nature in many biological processes. Therefore, targeted inhibition of GSK3β would be advantageous. To make the NP deliver drug to the specific remodeling bone area at fracture, a targeting peptide that has specific affinity to Tartrate-resistant acid phosphate (TRAP) was employed. The idea is, after fracture occurs, osteoclasts deposit TRAP on resorption surfaces that then enhance recognition of the resorption surfaces by osteoblasts.

The peptide with high and specific affinity for TRAP was identified in previous studies. This peptide was then introduced to the NP corona to enhance fracture specificity (FIG. 46, FIG. 47). The release drug at the fracture site provides Wnt/β-catenin upregulation and enhanced bone formation.

To investigate the in vivo accumulation of systemically administered NPs, IVIS imaging was used to visually investigate the fracture-targeting effect of peptide-conjugated NPs. Briefly, mid-diaphyseal femur fractures were created on BALB/c mice. Three days after surgery, NP alone, scrambled control peptide-conjugated NPs (SC-NP), and TRAP-binding peptide-conjugated NPs (TBP-NP) were loaded with IR780 (a near-IR model drug for visualization) and injected retro-orbitally. Distribution of IR780 was tracked for 2 weeks after injection. In all groups tested, accumulation of drug peaked at ~24-48 hrs post-injection (FIG. 48). While untargeted NPs accumulated at fracture sites, likely due to enhanced permeation and retention, targeting via TBP showed 2-fold greater and faster accumulation over untargeted NPs. To take a closer look at the tissue distribution, the fluorescence intensity of IR780 was measured in different organs. Fluorescence signal intensity of TBP-NP-delivered IR780 in fractured bone was ~2 fold higher than normal NP or SC-conjugated NP (FIG. 49). The fluorescence signal was barely detectable in the heart, spleen, lungs and kidneys of the mice from all the treatment groups, except for a small signal that was present in the kidney of mice injected with TBP-NP-IR780.

To evaluate the targeted localized activation of β-catenin, β-galactosidase activity of fractured femur was investigated 14 days after GSK3β inhibitor XXVII treatments using LacZ reporter mice. These mice contain a lacZ gene inserted downstream of 7 consensus binding sites for the T-cell Factor/Lymphoid Enhancer Factor (TCF/LEF) family of transcription factors, which are activated specifically upon nuclear (activated) β-catenin binding. This allows β-galactosidase to be expressed when β-catenin/TCF/LEF-driven transcription is activated through canonical Wnt stimulation. Positive LacZ staining is shown in blue in FIG. 50. Stronger β-galactosidase activity was observed in callus and periosteum in fractures treated with targeted NPs than untreated controls and untargeted NPs, indicating potent local β-catenin activation at fracture site during the healing process.

Example 9

Targeting the Bone Marrow Microenvironment

Acute myelogenous leukemia (AML) is a disease of the bone marrow that is newly diagnosed in over 18,000 patients in the United States yearly with approximately 25% of patients surviving beyond 5 years. Morbidity and mortality in this disease are caused, in large part, by loss of normal blood cell development. Hematopoietic stem cells (HSCs) are responsible for the maintenance of the blood system over the life of an individual and rely on a niche of multiple cellular components within the bone marrow microenvironment (BMME) for regulation of cell fate (Yates et al., 1973, Cancer Chemother Rep, 57(4): 485-488). In murine models of AML, it was previously demonstrated that loss of critical HSC niche components correlated with HSC dysfunction, and the chemokine CCL3 (Mip1α) was found to be highly upregulated and necessary for BMME modulation and leukemia development (Calvi et al., 2015, Blood, 126(22): 2443-2451). Further, samples of human AML displayed elevated levels of CCL3 mRNA and protein. Several small molecule inhibitors of the CCL3 signaling pathway have been developed and completed phase 2 clinical trials demonstrating safety for use in humans. Upon treatment of the murine model AML with 2 of these inhibitors, bx471 and maraviroc, it was demonstrated that a reduction in leukemic burden and an improvement in HSC dysfunction occurred, however, these results failed to completely rescue HSC dysfunction. Subpar pharmacodynamics is likely due to inadequate inhibitor half-lives and poor retention within the BMME. It is expected that a targeted drug delivery approach for inhibitors of the CCL3 pathway to the bone marrow microenvironment improves pharmacodynamics, producing greater therapeutic efficacy. Using small molecules loaded into nanoparticles that target BMME, with a delayed release, it is expected to produce an improvement in retention time in the marrow and subsequent reduction in leukemic cell burden (Frisch et al., 2008, Curr Opin Support Palliat Care, 2(3): 211-217, Frisch et al., 2012, Blood, 119(2): 540-550).

It has been demonstrated that the bone marrow microenvironment plays a critical role in hematologic malignancy, however, the mechanisms of leukemia/microenvironmental interactions are largely unknown (Frisch et al., 2012, Blood, 119(2): 540-550). It has been recently demonstrated that CCL3, also known as macrophage inflammatory protein 1α (Mip1α), affects the mechanism of microenvironmental disruption in AML (Frisch et al., 2012, Blood, 119(2): 540-550). This mechanism demonstrated that CCL3 is critical for the maintenance of leukemia initiating cells in the bone marrow of a murine model of chronic myelogenous leukemia (CML) (Baba et al., 2013, J Exp Med, 210(12): 2661-2673). Additionally, it has been demonstrated that CCL3 is a mechanism of microenvironmental disruption in other hematologic malignancies such as myelodysplastic syndrome (MDS) and multiple myeloma, as well as solid tumors such as lung cancer (Balderman et al., 2015, Blood, 127(5): 616-625, Vallet et al., 2011, Leukemia, 25(7): 1174-1181, Wu, Y., et al., 2008, J Immunol, 181(9): 6384-6393). Therefore, targeting the CCL3 signaling pathway is beneficial in the treatment of multiple patient populations.

It has been demonstrated that functional osteoblastic cells are lost in a murine model of myelogenous leukemia (FIG. 51). CCL3 has also been demonstrated to inhibit osteoblastic cells in mice and humans through osteoblastic expression of the receptors CCR1 and CCR5 (Abbas et al., 2003, Cytokine, 22(1-2): 33-41, Yano et al., 2005, Endocrinology, 146(5): 2324-2335). The expression of CCL3, as measured by q-PCR in bone marrow mononuclear cells (BMMCs), was increased in cells from leukemic compared to naïve mice (Frisch et al., 2012, Blood, 119(2): 540-504). CCL3 protein levels were also increased in the marrow plasma and blood serum from leukemic animals compared to normal controls (Frisch et al., 2012, Blood, 119(2): 540-504, Schepers et al., 2013, Cell Stem Cell, 13(3): 285-299). Sorted leukemic cells, demonstrating the highest level of expression of CCL3 in the bone marrow, indicated that they were the source of excess CCL3 protein (Frisch, B. J., et al., 2012, Blood, 2012. 119(2): 540-504). CCL3 expression was also increased in marrow samples from AML patients and CCL3 protein levels were elevated in the marrow plasma from AML patients compared to normal controls.

This data is in agreement with the analysis of microarray data previously demonstrated by Bullinger et al., in which 58 of 75 AML samples had elevated levels of CCL3 (Bullinger et al., 2004, N Engl J Med, 350(16): 1605-1612). Further, the use of genetic models to knock out CCL3 in leukemic cells, demonstrated that the disease is no longer serially transplantable (FIG. 52A, FIG. 52B), indicating a critical role for CCL3 in the maintenance of a leukemia initiating cell population. In light of this, it was demonstrated that CCL3 is required for osteoblastic inhibition in AML. Small molecule inhibitors of the receptors for CCL3 were used to perform these studies. Maraviroc (Pfizer) is an FDA approved drug for the treatment of HIV and inhibits the CCL3 receptor CCR5, and BX471 (Berlex/Scherring AG) has gone through phase 2 clinical trials for the treatment of multiple sclerosis and inhibits the CCL3 receptor CCR1.

It has been demonstrated in vitro that in the murine model of myelogenous leukemia, osteoblastic inhibition is caused, at least in part, by signaling through the CCL3 receptors CCR1 and CCR5 as treatment with a combination of Maraviroc and BX471 rescues expression of the osteoblast specific gene osteocalcin (FIG. 53). However, when these drugs are used in vivo, it was demonstrated that in the murine model of myelogenous leukemia, hematopoietic stem cell dysfunction is only partially rescued, and disease progression is not altered (FIG. 54), despite the fact that without CCL3 expression the leukemic disease is significantly decreased in primary recipients, and is no longer serially transplantable.

This indicates incomplete inhibition of CCL3 signaling through the use of BX471 and Maraviroc. This is explained by poor pharmacodynamics. In mice, BX471 given at a dose of 20 mg/kg reaches peak serum concentrations of 9 μM 30 minutes following subcutaneous injection, and after 2 hours serum concentrations are reduced more than 20 fold to 0.4 μM (Anders et al., 2002, J Clin Invest, 109(2): 251-259). In rats, Maraviroc was demonstrated to have a half-life of 0.9 hours indicating rapid clearance (Dorr et al., 2005, Antimicrob Agents Chemother, 49(11): 4721-4732). Therefore, it is expected that targeted drug delivery approaches for inhibitors of the CCL3 pathway to the bone marrow microenvironment improves support for normal HSCs in the bone marrow microenvironment. As part of the investigations on new strategies to enhance drug circulation half-lives, sustain release kinetics, and enable bone targeting, polymeric nanoparticles (NPs) composed of poly(styrene-alt-maleic anhydride) and poly(styrene) (PSMA-b-PS; FIG. 55, FIG. 56) and functionalized with a TRAP-binding peptide (TBP), as carriers for drug delivery to the bone marrow were developed (Baranello et al., 2015, Cellular and Molecular Bioengineering, 8(3): 455-470, Baranello et al., 2014, Biomacromolecules, 15(7): 2629-2641). It has been demonstrated that TRAP (tartrateresistant acid phosphatase) is produced by osteoclasts during bone resorption, accumulates in the marrow compartment, and is present in the bone marrow of leukemic mice from the model. (FIG. 57). It has been demonstrated that NP carriers functionalized with a TRAP-binding peptide (TPLSYLKGLVTV; SEQ ID NO. 3) (Sheu et al., 2003, Journal of Biological Chemistry, 278(1): 438-443) can bind to TRAP with high affinity (KD~5 μM) and that such affinity can be modulated (KD : $10^{-6}$-$10^{-3}$M) by varying the peptide density on the NP (3-12% w/w) (Newman et al., 2014, Tissue Engineering Part A, 2014. 20: S111-S111).

In addition, after injection into mice, TBP functionalized NPs loaded with an infrared-active molecule (IR780) showed significantly higher (3-fold) accumulation in TRAP-positive fracture callus versus all other tissues, as demonstrated by timepoint-matched tissue biodistribution analysis (FIG. 58). In contrast, untargeted NPs that lack the TBP peptide or modified with a scrambled peptide (SCR-NP), exhibited similar accumulation across all tissues (FIG. 58). Thus, TBP-functionalized NPs represent excellent candidates for selective delivery of drugs to TRAP-positive marrow. In recent studies (Baranello et al., 2015, Cellular and Molecular Bioengineering, 2015. 8(3): 455-470), a variety of hydrophobic drugs were loaded into these micelles with high drug capacity (~5-15% wt drug/wt micelle).

Furthermore, drug release can be sustained over a wide range of time frames (3 days-2 weeks) depending upon drug and micelle physicochemical properties. It has been demonstrated that BX471 exhibits 6% wt/wt loading capacity with sustained, zero-order drug release for over 10 days (FIG. 59), thus demonstrating the feasibility of these carriers for the controlled release of BX470 and Maraviroc. Therefore, CCR1 and CCR5 inhibitors BX471 and Maraviroc loaded into TBP-functionalized NPs are expected to treat 2 separate murine models of myelogenous leukemia.

Model 1: A model of blast crisis CML (bcCML) previously published with in regards to CCL3-mediated osteoblastic disruption is used (Frisch et al., 2012, Blood, 119(2): 540-550). In this model, the translocation products BCR/ABL and Nup98/HoxA9 are coexpressed in hematopoietic progenitor cells through murine stem cell virus retroviral constructs. The retroviral constructs also express GFP and YFP respectively for identification of leukemic cells (FIG. 52A). Model 2: A murine model of AML in which the translocation product MLL/AF9 is expressed in hematopoietic progenitor cells through a murine stem cell virus retroviral construct (Somervaille et al., 2006, Cancer Cell, 10(4): 257-268). The construct also expresses GFP for identification of leukemic cells.

Following treatment with nanoparticle loaded inhibitors compared to free inhibitor controls, immunohistochemistry and flow cytometric analysis are utilized to demonstrate an improvement in critical HSC niche cellular components such as mesenchymal stem cells, osteoblastic cells, and endothelial cells. Leukemia is induced using both murine models, and the leukemic cells are allowed to engraft for 2 days prior to beginning treatment. Following successful engraftment, one daily treatment with 10 mg/kg BX471 and 20 mg/kg Maraviroc, both free and loaded into TBP-functionalized NPs, are carried out for 8 days. This timepoint is chosen based on previous data that demonstrates loss of functional osteoblastic cells 10 days following transplantation of leukemic cells (FIG. 51, FIG. 54). The following groups are included and 5 mice are used per treatment group, the experiment being repeated 3 times (Table 5).

TABLE 5

| Mouse Type | Treatment | Experimental Endpoints |
| --- | --- | --- |
| Normal mouse control | None | Immunohistochemical and Flow cytometric analysis for Osteoblastic Cells, Endothelial Cells and Mesenchymal Stem Cells |
| Leukemic mouse (bcCML and AML murine models) | Vehicle treated Free BX471 and Maraviroc treated TBP-functionalized NPs loaded BX471 and Maraviroc treated | |

Immunohistochemical analysis performed on 1 hind limb from each experimental mouse included identification of established targets, osteocalcin (osteoblast), and endomucin (endothelial) (Balderman et al., 2015, Blood, 127(5): 616-625). Flow cytometric analysis is used to quantify numbers of osteoblastic cells, endothelial cells, and mesenchymal stem cells (Table 6) (Balderman et al., 2015, Blood, 127(5): 616-625.

TABLE 6

| Osteoblastic Cells | CD45-, CD11b-, GR1-, Ter119-, b220-, CD31-, CD51+, sca1- |
| --- | --- |
| Endothelial Cells | CD45-, CD11b-, GR1-, Ter119-, b220-, CD31+, sca1+/- |
| Mesenchymal Stem Cells | CD45-, CD11b-, GR1-, Ter119-, b220-, CD31-, CD51+, sca1+ |

These three cellular populations are quantified from tissue obtained from the second hind limb of each experimental mouse, included the whole bone marrow, and bone associated cells that had been enzymatically digested from bone fragments.

As demonstrated previously, murine models of leukemic cells are allowed to engraft for 2 days prior to once a day treatment with 10 mg/kg BX471 and 20 mg/kg Maraviroc, both free and loaded into TBP-functionalized NPs for 8 days. This timepoint was chosen based on previous data demonstrating increased numbers of HSCs 10 days following transplantation of leukemic cells (FIG. 54). Hematopoietic stem and progenitor cell (HSPC) populations are quantified by flow cytometric analysis. Additionally, the Lineage-$Sca1^+ckit^+$ population of HSPCs are sorted by flow cytometry on a BD FACS aria II. Normal HSPCs are separated from leukemic cell populations based on their lack of GFP and YFP positivity. Sorted HSPCs are competitively transplanted into myelo-ablated recipient mice, and their repopulation of the hematopoietic system are tracked via analysis of peripheral blood (FIG. 60). 5 mice are used per treatment group, and the experiment is repeated 3 times.

It is expected that increased numbers of HSCs in the bone marrow of leukemic mice correlates with decreased HSC function. It has been previously demonstrated that treatment with BX471 and Maraviroc partially rescues HSC numbers, and it is expected that improved pharmacodynamics results in greater rescue in HSC numbers and therefore HSC function. This experiment provides data that reveals the specific mechanisms of microenvironmental support of HSCs that are lost in the leukemic microenvironment.

As described in the previous section, leukemic cells are allowed to engraft for 2 days prior to once daily treatment with 10 mg/kg BX471 and 20 mg/kg Maraviroc both free and loaded into TBP-functionalized NPs for 8 days. This timepoint is chosen based on data demonstrating increased numbers of HSCs 10 days following transplantation of leukemic cells (FIG. 54). 5 de-identified primary AML patient samples are selected for CCL3 expression and ability to engraft in sub-lethally irradiated NSG mice are analyzed. Leukemic cells are allowed to engraft for 2 weeks following transplantation. Following engraftment, xenografted mice are treated with 10 mg/kg BX471 and 20 mg/kg Maraviroc, both free and loaded into TBP-functionalized NPs for 8 days. For murine models, 5 mice are used per treatment group, and the experiment is repeated 3 times. For AML patient samples, 10 recipient mice are used per sample. The following experimental endpoints were included: immunohistochemical analysis demonstrating the presence and location of leukemic cells in the bone marrow; and flow cytometric analysis of bone marrow, spleen and peripheral blood for quantification of GFP and YFP cells demonstrating a reduction in leukemic burden in murine models, and human CD45 positive cells to demonstrate a reduction in leukemic burden in xenograft models.

Murine models of leukemia, primary samples of AML, and experimental groups are treated as described previously. Bone marrow cells from all models and treatment groups are retransplanted into secondary recipients demonstrating their ability to reinitiate leukemic disease following inhibition of the CCL3 signaling pathway.

Previously, the experimental results demonstrated that expression of CCR1 and CCR5 on both the BMME and leukemic cells is necessary for the maintenance of a leukemia initiating cell and leukemic progression in a murine model CIVIL (Baba et al., 2013, J Exp Med, 210(12): 2661-2673). Therefore, it is expected that bone marrow targeted pharmacologic inhibition with BX471 and Maraviroc reduces leukemic burden and numbers of function leukemia initiating cells in murine models of bcCML and AML, as well as primary human AML xenografts.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition for controlled local delivery of a therapeutic agent to bone, the composition comprising a therapeutic-tethered macromer comprising a targeting ligand and a therapeutic agent tethered to a polymer, wherein the therapeutic agent is 3-amino-6-{4-[(4-methyl-1-piperazinyl)sulfonyl]phenyl}-N-(3-pyridinyl)-2-pyrazinecarboxamide, and wherein the polymer is selected from the group consisting of poly(ethylene glycol) (PEG) methacrylate and poly(styrene-alt-maleic anhydride)-b-poly(styrene) (PSMA-b-PS).

2. The composition of claim 1, further comprising a C-C motif ligand 3(CCL3) pathway inhibitor.

3. The composition of claim 2, wherein the CCL3 pathway inhibitor is selected from the group consisting of BX471 and Maraviroc.

4. The composition of claim 1, wherein the targeting ligand is tethered to polymer micelles encapsulating the therapeutic agent.

5. The composition of claim 1, wherein the therapeutic agent is tethered to the polymer via at least one degradable tether.

6. The composition of claim 1, wherein the therapeutic-tethered macromer is contained within a hydrogel.

7. The composition of claim 1, wherein the composition comprises a bone-homed particle comprising the therapeutic-tethered macromer.

8. The composition of claim 7, wherein the bone-homed particle comprises at least one targeting domain that specifically binds to a target associated with a site in need of bone formation.

9. The composition of claim 8, wherein the at least one targeting domain comprises a targeting peptide that specifically binds to tartrate-resistant acid phosphatase (TRAP).

10. The composition of claim 7, wherein the bone-homed particle comprises at least one monomer that targets the particle to bone, to a resorptive pit, to a bone fracture, to bone marrow, or any combination thereof.

11. The composition of claim 10, wherein the monomer is a phosphate-containing monomer.

12. The composition of claim 10, wherein the monomer is selected from the group consisting of 6-methacryloyloxyhexyl dihydrogen phosphate, methacrylated glutamic acid, and methacrylated aspartic acid.

13. The composition of claim 7, wherein the particle comprises multivalent targeting.

14. The composition of claim 9, wherein the targeting peptide comprises the amino acid sequence of SEQ ID NO: 1.

15. The composition of claim 7, wherein the bone-homed particle is a micelle, a nanoparticle, or a polymer.

16. The composition of claim 15, wherein the polymer comprises one or more monomers that target the polymer to bone, to a resorptive pit, to a bone fracture, to bone marrow, or any combination thereof.

17. A composition for controlled local delivery of a therapeutic agent to bone, the composition comprising a therapeutic-tethered macromer comprising a targeting ligand and a therapeutic agent tethered to poly(styrene-alt-maleic anhydride)-b-poly(styrene) (PSMA-b-PS), wherein the therapeutic agent is an inhibitor of GSK3β.

18. The composition of claim 17, wherein the therapeutic agent is a C-C motif ligand 3(CCL3) pathway inhibitor.

19. The composition of claim 18, wherein the CCL3 pathway inhibitor is BX471, Maraviroc, or both.

20. The composition of claim 17, wherein the targeting ligand is tethered to polymer micelles encapsulating the therapeutic agent.

21. The composition of claim 17, wherein the therapeutic agent is selected from the group consisting of 6-bromoindirubin-3'-oxime (BIO) and 3-amino-6-{4-[(4-methyl-1-piperazinyl)sulfonyl]phenyl}-N-(3-pyridinyl)-2-pyrazinecarboxamide.

22. The composition of claim 17, wherein the therapeutic agent is tethered to the polymer via at least one degradable tether.

23. The composition of claim 17, wherein the composition comprises a bone-homed particle comprising the therapeutic-tethered macromer.

24. The composition of claim 23, wherein the bone-homed particle comprises at least one targeting domain that specifically binds to a target associated with a site in need of bone formation.

25. The composition of claim 24, wherein the at least one targeting domain is selected from the group consisting of a nucleic acid, peptide, antibody, antibody fragment, inorganic molecule, organic molecule, and combination thereof.

26. The composition of claim 25, wherein the at least one targeting domain comprises a targeting peptide that specifically binds to tartrate-resistant acid phosphatase (TRAP).

27. The composition of claim 23, wherein the bone-homed particle comprises at least one monomer that targets the particle to bone.

28. The composition of claim 23, wherein the bone-homed particle comprises at least one monomer that targets the particle to a resorptive pit, a bone fracture, bone marrow, or any combination thereof.

29. The composition of claim 28, wherein the monomer is a phosphate-containing monomer.

30. The composition of claim 28, wherein the monomer is selected from the group consisting of 6-methacryloyloxy-hexyl dihydrogen phosphate, methacrylated glutamic acid, and methacrylated aspartic acid.

31. The composition of claim 23, wherein the particle comprises multivalent targeting.

32. The composition of claim 26, wherein the targeting peptide comprises the amino acid sequence of SEQ ID NO: 1.

33. The composition of claim 23, wherein the bone-homed particle is a micelle, a nanoparticle, or a polymer.

34. The composition of claim 33, wherein the polymer comprises one or more monomers that target the polymer to bone, to a resorptive pit, to a bone fracture, to bone marrow, or any combination thereof.

35. A method of promoting bone formation at a site in need of bone formation in a subject comprising administering to the subject the composition of claim 1, wherein the composition promotes bone formation.

36. The method of claim 35, wherein the subject has a disease or disorder selected from the group consisting of osteoporosis, osteonecrosis, osteomyelitis, osteoarthritis, Paget's disease, bone cancer, bone allograft rejection, bone autograft rejection, wear-debris induced osteolysis, and bone fracture.

37. A method of promoting bone formation at a site in need of bone formation in a subject comprising administering to the subject the composition of claim 17, wherein the composition promotes bone formation.

38. The method of claim 37, wherein the subject has a disease or disorder selected from the group consisting of osteoporosis, osteonecrosis, osteomyelitis, osteoarthritis, Paget's disease, bone cancer, bone allograft rejection, bone autograft rejection, wear-debris induced osteolysis, and bone fracture.

* * * * *